US011421349B2

(12) United States Patent
Piergallini et al.

(10) Patent No.: US 11,421,349 B2
(45) Date of Patent: Aug. 23, 2022

(54) PHOTOACTIVATABLE FIBERS AND FABRIC MEDIA

(71) Applicant: KLOX TECHNOLOGIES INC., Laval (CA)

(72) Inventors: Remigio Piergallini, Grottammare (IT); Nikolaos Loupis, Athens (GR); David Ohayon, Quebec (CA)

(73) Assignee: KLOX TECHNOLOGIES INC., Laval (CA)

( * ) Notice: Subject to any disclaimer, the term of this patent is extended or adjusted under 35 U.S.C. 154(b) by 0 days.

(21) Appl. No.: 15/523,283

(22) PCT Filed: Oct. 30, 2015

(86) PCT No.: PCT/CA2015/051118
§ 371 (c)(1),
(2) Date: Apr. 28, 2017

(87) PCT Pub. No.: WO2016/065488
PCT Pub. Date: May 6, 2016

(65) Prior Publication Data
US 2017/0362744 A1 Dec. 21, 2017

Related U.S. Application Data

(60) Provisional application No. 62/073,795, filed on Oct. 31, 2014.

(51) Int. Cl.
*A61N 5/06* (2006.01)
*D01F 1/10* (2006.01)
(Continued)

(52) U.S. Cl.
CPC ............ *D01F 1/106* (2013.01); *A61N 5/062* (2013.01); *A61N 5/0616* (2013.01); *C09K 11/02* (2013.01);
(Continued)

(58) Field of Classification Search
CPC ....... D01F 1/106; A61N 5/0616; A61N 5/062; A61N 2005/063; A61N 2005/0645;
(Continued)

(56) References Cited

U.S. PATENT DOCUMENTS 2,877,221 A    3/1959  Lanbach
3,107,968 A *  10/1963 Pascal ................. D06P 3/522
                                                  8/654
(Continued)

FOREIGN PATENT DOCUMENTS

CA    2166527 A1    7/1996
CA    2222027 A1    6/1998
(Continued)

OTHER PUBLICATIONS

Alster, et al., "Photodynamic therapy: practical cosmetic applications," Journal of Drugs in Dermatology, 5(8):764-768 (2006).
(Continued)

*Primary Examiner* — Carl H Layno
*Assistant Examiner* — Michael J Lau
(74) *Attorney, Agent, or Firm* — BCF LLP

(57) ABSTRACT

In various aspects, the present disclosure relates to fibers and fabric media comprising photoactivatable agents and to fibers and fabric media that are photoactivatable by photoactivation of the photoactivatable agents. In some instances, the fibers and the fabric media have photoactivatable agents present on their surface (e.g., the fiber/fabric is coated or sprayed with the photoactivatable agents or the fiber/fabric is dipped into a composition or a formulation comprising the photoactivatable agent). In other instances, the photoactivatable agents are incorporated into the materials making the fibers (e.g., the photoactivatable agents are mixed/compounded with the materials making the fibers). The photoactivatable fibers of the present disclosure comprise at least
(Continued)

one thermoplastic polymer and at least photoactivatable agent that absorbs and emits light between about 400 nm and about 800 nm.

14 Claims, 13 Drawing Sheets

(51) Int. Cl.
<table>
<tr><td>D06P 1/00</td><td>(2006.01)</td></tr>
<tr><td>C09K 11/02</td><td>(2006.01)</td></tr>
<tr><td>C09K 11/06</td><td>(2006.01)</td></tr>
</table>

(52) U.S. Cl.
CPC ............ *C09K 11/06* (2013.01); *D06P 1/0012* (2013.01); *A61N 2005/063* (2013.01); *A61N 2005/0645* (2013.01); *A61N 2005/0651* (2013.01); *A61N 2005/0659* (2013.01); *A61N 2005/0662* (2013.01); *C09K 2211/1018* (2013.01)

(58) Field of Classification Search
CPC .... A61N 2005/0659; A61N 2005/0662; C09K 11/02; C09K 11/06; C09K 2211/1018; D06P 1/0012
USPC .............................................. 607/91; 602/48
See application file for complete search history.

(56) References Cited

U.S. PATENT DOCUMENTS

| | | | |
|---|---|---|---|
| 3,293,127 A | 12/1966 | Beck | |
| 3,309,274 A | 3/1967 | Brilliant | |
| 3,336,923 A * | 8/1967 | Devaud | A61F 13/022 604/374 |
| 3,372,125 A | 3/1968 | Hill | |
| 3,595,798 A | 7/1971 | Smith et al. | |
| 3,597,362 A | 8/1971 | Rauhut et al. | |
| 3,652,420 A | 3/1972 | Hill | |
| 3,671,450 A | 6/1972 | Rauhut et al. | |
| 3,728,446 A | 4/1973 | Roberts et al. | |
| 3,795,530 A * | 3/1974 | Gundlach | G03G 13/10 430/113 |
| 4,320,140 A | 3/1982 | Crounse et al. | |
| 4,574,097 A | 3/1986 | Honeycutt | |
| 4,891,211 A | 1/1990 | Winston | |
| 4,923,726 A | 5/1990 | Maruyama et al. | |
| 4,992,256 A | 2/1991 | Skaggs et al. | |
| 5,292,362 A | 3/1994 | Bass et al. | |
| 5,478,628 A * | 12/1995 | Billingsley | D06N 3/0065 442/132 |
| 5,516,227 A | 5/1996 | Kozak et al. | |
| 5,611,793 A | 3/1997 | Wilson et al. | |
| 5,658,148 A | 8/1997 | Neuberger et al. | |
| 5,677,028 A * | 10/1997 | Ravella | D04H 1/46 442/403 |
| 5,723,148 A | 3/1998 | Love | |
| 5,749,968 A | 5/1998 | Melanson et al. | |
| 5,785,527 A | 7/1998 | Jensen et al. | |
| 5,844,016 A | 12/1998 | Sawhney et al. | |
| 5,858,332 A | 1/1999 | Jensen et al. | |
| 5,885,557 A | 3/1999 | Lentini | |
| 5,914,076 A * | 6/1999 | Schloss | D01F 1/10 264/211 |
| 5,922,331 A | 7/1999 | Mausner | |
| 5,977,199 A | 11/1999 | Xie | |
| 6,030,222 A | 2/2000 | Tarver | |
| 6,036,493 A | 3/2000 | Sharma | |
| 6,056,548 A | 5/2000 | Neuberger et al. | |
| 6,084,005 A | 7/2000 | Fukunishi et al. | |
| 6,107,466 A | 8/2000 | Hasan et al. | |
| 6,121,341 A | 9/2000 | Sawhney et al. | |
| 6,149,895 A | 11/2000 | Kutsch | |
| 6,162,055 A | 12/2000 | Montgomery et al. | |
| 6,217,794 B1 * | 4/2001 | Neal | C08K 5/0091 428/670 |
| 6,254,388 B1 | 7/2001 | Yarborough | |
| 6,267,976 B1 | 7/2001 | Barnhart et al. | |
| 6,337,357 B1 | 1/2002 | Fukunishi et al. | |
| 6,343,933 B1 | 2/2002 | Montgomery et al. | |
| 6,365,134 B1 | 4/2002 | Orlowski et al. | |
| 6,387,353 B1 | 5/2002 | Jensen et al. | |
| 6,391,283 B1 | 5/2002 | Jensen et al. | |
| 6,420,455 B1 | 7/2002 | Landgrebe et al. | |
| 6,485,709 B2 | 11/2002 | Banerjee | |
| 6,541,460 B2 | 4/2003 | Petito | |
| 6,849,330 B1 * | 2/2005 | Morin | D01F 1/04 428/394 |
| 6,905,672 B2 | 6/2005 | Rajaiah et al. | |
| 7,066,941 B2 | 6/2006 | Perricone | |
| 7,081,128 B2 | 7/2006 | Hart et al. | |
| 7,314,470 B2 | 1/2008 | Malodobry | |
| 7,354,448 B2 | 4/2008 | Altshuler et al. | |
| 7,611,831 B2 * | 11/2009 | Hei | B01J 20/28085 530/413 |
| 8,075,875 B2 | 12/2011 | Piergallini et al. | |
| 8,182,473 B2 | 5/2012 | Altshuler et al. | |
| 8,632,822 B2 | 1/2014 | Piergallini et al. | |
| 8,637,086 B2 | 1/2014 | Piergallini et al. | |
| 8,658,219 B2 | 2/2014 | Piergallini et al. | |
| 8,685,466 B2 | 4/2014 | Piergallini et al. | |
| 8,911,791 B2 | 12/2014 | Piergallini et al. | |
| 8,974,833 B2 | 3/2015 | Piergallini et al. | |
| 8,986,719 B2 | 3/2015 | Piergallini et al. | |
| 8,986,745 B2 | 3/2015 | Piergallini et al. | |
| 8,986,746 B2 | 3/2015 | Piergallini et al. | |
| 9,375,446 B2 | 6/2016 | Piergallini et al. | |
| 2001/0022970 A1 | 9/2001 | Dees et al. | |
| 2001/0045677 A1 * | 11/2001 | Kang | D01F 1/10 264/28 |
| 2002/0157165 A1 * | 10/2002 | Kroll | G02C 5/00 2/102 |
| 2003/0085384 A1 * | 5/2003 | Burnell-Jones | C09K 11/02 252/301.36 |
| 2003/0157323 A1 * | 8/2003 | Khavkine | D02G 3/04 428/373 |
| 2003/0198605 A1 | 10/2003 | Montgomery | |
| 2004/0136971 A1 | 7/2004 | Scharp et al. | |
| 2004/0147508 A1 * | 7/2004 | Brown | A61P 17/06 514/217.05 |
| 2004/0191330 A1 | 9/2004 | Keefe et al. | |
| 2004/0262569 A1 | 12/2004 | Cho et al. | |
| 2005/0026298 A1 | 2/2005 | Bickett et al. | |
| 2005/0042428 A1 * | 2/2005 | Dean | C09K 11/06 283/92 |
| 2005/0042712 A1 | 2/2005 | Huth et al. | |
| 2005/0059731 A1 | 3/2005 | Albrecht et al. | |
| 2005/0098766 A1 | 5/2005 | Watson et al. | |
| 2005/0123588 A1 | 6/2005 | Zhu et al. | |
| 2005/0244455 A1 * | 11/2005 | Greenawalt | C08L 23/12 424/423 |
| 2005/0261750 A1 | 11/2005 | McDaniel | |
| 2006/0199242 A1 | 9/2006 | Cheung et al. | |
| 2006/0217690 A1 | 9/2006 | Bastin et al. | |
| 2006/0228320 A1 | 10/2006 | Minami et al. | |
| 2006/0251687 A1 | 11/2006 | Lapidot et al. | |
| 2007/0016173 A1 * | 1/2007 | Kreindel | H01Q 17/00 606/1 |
| 2007/0021807 A1 | 1/2007 | Kurtz | |
| 2007/0092469 A1 | 4/2007 | Jacobs | |
| 2007/0128132 A1 | 6/2007 | Piergallini et al. | |
| 2007/0142762 A1 * | 6/2007 | Kaplan | A61F 13/0203 602/43 |
| 2007/0149722 A1 * | 6/2007 | Fujiguchi | C08L 69/00 525/464 |
| 2007/0166369 A1 | 7/2007 | Neuberger et al. | |
| 2007/0191249 A1 | 8/2007 | Lant | |
| 2007/0244195 A1 | 10/2007 | Burkhart et al. | |
| 2007/0288071 A1 * | 12/2007 | Rogers | A61N 5/062 607/88 |
| 2007/0290172 A1 * | 12/2007 | Momose | G02B 5/223 252/301.16 |

(56) References Cited

U.S. PATENT DOCUMENTS

| | | | |
|---|---|---|---|
| 2008/0058689 A1 | 3/2008 | Holloway et al. | |
| 2008/0060148 A1* | 3/2008 | Pinyayev | A61B 5/0088 15/4 |
| 2008/0108681 A1 | 5/2008 | Scimeca et al. | |
| 2008/0113037 A1 | 5/2008 | Green et al. | |
| 2008/0118578 A1 | 5/2008 | Dees et al. | |
| 2008/0138289 A1 | 6/2008 | Goronkin et al. | |
| 2008/0206159 A1 | 8/2008 | Tamarkin et al. | |
| 2008/0255498 A1* | 10/2008 | Houle | A61C 17/0208 604/20 |
| 2008/0262154 A1* | 10/2008 | Behrens | C08F 2/44 524/801 |
| 2008/0305101 A1 | 12/2008 | Ruoslahti et al. | |
| 2009/0036593 A1* | 2/2009 | DeRudder | C08L 55/02 524/506 |
| 2009/0041984 A1* | 2/2009 | Mayers | G02B 3/0006 427/256 |
| 2009/0246251 A1* | 10/2009 | Orgambide | A61K 38/16 424/93.1 |
| 2010/0040809 A1* | 2/2010 | Muller | D01F 6/04 428/17 |
| 2010/0063467 A1* | 3/2010 | Addison | A61L 15/42 604/361 |
| 2010/0125963 A1* | 5/2010 | Kneidel | A46D 1/04 428/394 |
| 2010/0159769 A1* | 6/2010 | MacDonald | B32B 27/302 524/110 |
| 2010/0227799 A1 | 9/2010 | Trudel | |
| 2010/0255045 A1 | 10/2010 | Eymard Du Vernet | |
| 2010/0266989 A1 | 10/2010 | Piergallini et al. | |
| 2011/0143621 A1* | 6/2011 | MacDonald | A61L 29/141 128/207.14 |
| 2011/0171310 A1 | 7/2011 | Gousse et al. | |
| 2011/0245748 A1 | 10/2011 | Rinke | |
| 2011/0313407 A1* | 12/2011 | Rafailov | A61N 5/062 977/773 |
| 2012/0080613 A1* | 4/2012 | Kingsley | F21V 9/38 428/411.1 |
| 2012/0100039 A1* | 4/2012 | Appeaning | A61L 2/088 422/186.01 |
| 2012/0116391 A1* | 5/2012 | Houser | A61B 18/1442 606/1 |
| 2012/0157576 A1* | 6/2012 | Bassetti | C04B 16/0675 524/4 |
| 2012/0171641 A1 | 7/2012 | Piergallini et al. | |
| 2012/0283622 A1* | 11/2012 | Nath | A61K 31/409 604/20 |
| 2013/0060183 A1* | 3/2013 | Ramirez | A63B 71/14 428/80 |
| 2013/0115843 A1* | 5/2013 | Klaska | D06M 13/256 28/103 |
| 2013/0122467 A1 | 5/2013 | Piergallini et al. | |
| 2013/0281913 A1 | 10/2013 | Piergallini et al. | |
| 2014/0082859 A1* | 3/2014 | Morton | D06P 5/12 8/483 |
| 2014/0105832 A1* | 4/2014 | Loupis | A61Q 11/00 424/53 |
| 2014/0128943 A1* | 5/2014 | Rogers | A61N 5/0603 607/92 |
| 2014/0161850 A1 | 6/2014 | Bickford | |
| 2014/0260437 A1* | 9/2014 | Fleming, Jr. | D04B 21/205 66/81 |
| 2014/0276354 A1 | 9/2014 | Piergallini et al. | |
| 2014/0303547 A1 | 10/2014 | Loupis et al. | |
| 2014/0306869 A1* | 10/2014 | Fujita | C07F 15/0033 546/4 |
| 2014/0308867 A1* | 10/2014 | Van Emmerick | C23C 14/20 442/379 |
| 2014/0309717 A1* | 10/2014 | Gustavsson | A61N 5/0613 607/90 |
| 2015/0065453 A1 | 3/2015 | Piergallini et al. | |
| 2015/0119788 A1 | 4/2015 | Loupis et al. | |
| 2015/0246127 A1 | 9/2015 | Loupis et al. | |
| 2015/0290103 A1 | 10/2015 | Piergallini et al. | |
| 2015/0290320 A1 | 10/2015 | Piergallini et al. | |
| 2015/0306131 A1 | 10/2015 | Piergallini et al. | |
| 2015/0360047 A1 | 12/2015 | Loupis et al. | |
| 2016/0136075 A1 | 5/2016 | Loupis et al. | |
| 2016/0205925 A1* | 7/2016 | Nisnevitch | A61K 41/0057 |
| 2017/0209348 A1* | 7/2017 | Piergallini | A61P 17/16 |
| 2020/0063299 A1* | 2/2020 | Tanaka | D03D 15/533 |

FOREIGN PATENT DOCUMENTS

| | | | |
|---|---|---|---|
| CA | 2360202 A1 | 7/2000 | |
| CA | 2457590 A1 | 3/2003 | |
| CA | 2551613 A1 | 12/2005 | |
| CA | 2580381 A1 | 1/2006 | |
| CA | 2706808 A1 | 8/2009 | |
| CA | 2738035 A1 | 4/2010 | |
| CA | 2742942 A1 | 5/2010 | |
| CA | 2742943 A1 | 5/2010 | |
| CA | 2745059 A1 | 6/2010 | |
| CA | 2809405 A1 | 1/2012 | |
| CA | 2868893 A1 | 10/2013 | |
| CA | 2902363 A1 * | 9/2014 | A61K 8/0212 |
| CA | 2902363 A1 * | 9/2014 | A61K 41/0057 |
| CN | 102133208 A | 7/2011 | |
| CN | 102603232 A | 7/2012 | |
| DE | 2935450 A1 | 3/1981 | |
| EP | 0380157 A1 | 8/1990 | |
| EP | 0704539 A2 | 4/1996 | |
| EP | 1235543 A1 | 9/2002 | |
| EP | 1235544 A1 | 9/2002 | |
| EP | 1779891 A1 | 5/2007 | |
| EP | 1951184 A2 | 8/2008 | |
| EP | 2338465 A1 | 6/2011 | |
| GB | 2469219 A * | 10/2010 | A61K 31/765 |
| GB | 2469219 A * | 10/2010 | A61K 31/765 |
| JP | S60-199942 A | 10/1985 | |
| JP | H01-111075 A | 4/1989 | |
| JP | 01-279838 | 11/1989 | |
| JP | 03169805 | 7/1991 | |
| JP | 04-219756 | 8/1992 | |
| JP | 06049771 A * | 2/1994 | A41D 31/325 |
| JP | 06049771 A * | 2/1994 | A41D 13/01 |
| JP | H06-128807 A | 5/1994 | |
| JP | H08-127937 A | 5/1996 | |
| JP | H092925 A | 1/1997 | |
| JP | H10182390 A | 7/1998 | |
| JP | H10330235 A | 12/1998 | |
| JP | 2001-511137 A | 8/2001 | |
| JP | 2002-502864 A | 1/2002 | |
| JP | 2002-226349 A | 8/2002 | |
| JP | 2002-233612 A | 8/2002 | |
| JP | 2002-293747 A | 10/2002 | |
| JP | 2003-339875 A | 12/2003 | |
| JP | 2009-500135 A | 1/2009 | |
| JP | 2011-063889 A | 3/2011 | |
| JP | 2012512932 A | 6/2012 | |
| JP | 2015-510668 A | 4/2015 | |
| JP | 2015-528472 A | 9/2015 | |
| JP | 2016-505553 A | 2/2016 | |
| JP | 2016-514000 A | 5/2016 | |
| KR | 10-20070017292 | 2/2007 | |
| WO | WO-1981000513 A1 | 3/1981 | |
| WO | WO-1990009779 A1 | 9/1990 | |
| WO | WO-1991002530 A1 | 3/1991 | |
| WO | WO-1997021420 A1 | 6/1997 | |
| WO | WO-1998010738 A1 | 3/1998 | |
| WO | WO-1998011827 A1 | 3/1998 | |
| WO | WO-1998023219 A1 | 6/1998 | |
| WO | WO-1998030169 A1 | 7/1998 | |
| WO | WO-1998033761 A1 | 8/1998 | |
| WO | WO-1999039238 A1 | 8/1999 | |
| WO | WO-1999040870 A1 | 8/1999 | |
| WO | WO-1999049823 A1 | 10/1999 | |
| WO | WO-1999063900 A1 | 12/1999 | |
| WO | WO-2000040266 A2 | 7/2000 | |
| WO | WO-2001000190 A2 | 1/2001 | |
| WO | WO-2001012181 A1 | 2/2001 | |
| WO | WO-2002011539 A1 | 2/2002 | |

(56) References Cited

FOREIGN PATENT DOCUMENTS

| | | |
|---|---|---|
| WO | WO-2002022097 A1 | 3/2002 |
| WO | WO-2003000215 A1 | 1/2003 |
| WO | WO-2003017824 A2 | 3/2003 |
| WO | WO-2003061696 A2 | 7/2003 |
| WO | WO-2003086215 A1 | 10/2003 |
| WO | WO-2003099247 A1 | 12/2003 |
| WO | WO-2004028498 A1 | 4/2004 |
| WO | WO-2004081222 A2 | 9/2004 |
| WO | 2004/104277 A1 | 12/2004 |
| WO | WO-2005009604 A1 | 2/2005 |
| WO | WO-2005051305 A2 | 6/2005 |
| WO | WO-2006014597 A1 | 2/2006 |
| WO | WO-2006032847 A1 | 3/2006 |
| WO | WO-2006047868 A1 | 5/2006 |
| WO | WO-2006072243 A1 | 7/2006 |
| WO | WO-2006118835 A2 | 11/2006 |
| WO | WO-2006125650 A1 | 11/2006 |
| WO | WO-2006135344 A1 | 12/2006 |
| WO | WO-2007025244 A2 | 3/2007 |
| WO | WO-2007080453 A2 | 7/2007 |
| WO | WO-2007087259 A2 | 8/2007 |
| WO | WO-2007127172 A2 | 11/2007 |
| WO | WO-2008011707 A1 | 1/2008 |
| WO | WO-2008013962 A2 | 1/2008 |
| WO | WO-2008052081 A2 | 5/2008 |
| WO | WO-2009089346 A2 | 7/2009 |
| WO | WO-2010051636 A1 | 5/2010 |
| WO | WO-2010051641 A1 | 5/2010 |
| WO | WO-2010070292 A1 | 6/2010 |
| WO | WO-2010/0151563 A1 | 12/2010 |
| WO | WO-2011006263 A1 | 1/2011 |
| WO | WO-2011058448 A2 | 5/2011 |
| WO | WO-2011134087 A1 | 11/2011 |
| WO | WO-2012011875 A1 | 1/2012 |
| WO | WO-2012072980 A1 | 6/2012 |
| WO | WO2013113349 A1 | 8/2013 |
| WO | WO-2013155620 A1 | 10/2013 |
| WO | WO-2014040176 A1 | 3/2014 |
| WO | WO-2014040177 A1 | 3/2014 |
| WO | WO-2014138930 A1 | 9/2014 |
| WO | WO-2015000058 A1 | 1/2015 |
| WO | WO-2015184551 A1 | 12/2015 |
| WO | WO-2016065488 A1 | 5/2016 |
| WO | WO-2017201615 A1 | 11/2017 |

OTHER PUBLICATIONS

Antunes, et al., "Evaluation of the ciastogenicity and anticiastongenicity of the carotenoid bixin in human lymphocyte cultures," Mutation Research, 585(1-2):113-9 (2005).
Ariizumi et al., "Clinical evaluation of a topical applicant TSG-88 for periodontal disease," Dental Drug Therapy, 10(2):157-168 (1991) (English Abstract included).
Berneburg, et al., "Phototherapy with narrowband UVB," Acta Dermato-Venereologica, 85:1-11 (2005).
Chen et al., "Study of the chemiluminescent characteristics of some xanthone dyes," Analytica Chimica Acta, 292(1-2):159-167 (1994).
Clark, et al., "Eosin-Phloxine alcoholic solution," Mitt. Zool. Stat. Neapel, Jan. 1, 1981 (Jan. 1, 1981), pp. 170-186, XP055224968, Retrieved from the Internet: URL:http://tunic.ro/fise/tehnice/05-10020L.pdf * abstract * (1 page).
Colman, et al., "The healing of wounds in the skin of piglets treated with benzoyl peroxide," The Journal of Dermatologic Surgery and Oncology, 4(9):705-707 (1978).
Darzynkiewicz, et al., "Photosensitizing effects of the tricyclic heteroaromatic cationic dyes Pyronin Y and Toluidine Blue O (tolonium chloride)," Cancer Research, 48(5):1295-1299 (1988).
De, et al., "Environmental effects on the aggregation of some xanthene dyes used in lasers," Spectrochimica Acta Part A: Molecular and Biomolecular Spectroscopy, 61(8):1821-1833 (2005).
Decraene et al., "Cellulose acetate containing Toluidine Blue and Rose Bengal is an effective antimicrobial coating when exposed to white light," Applied and Env. Microbiology, 72:6(4436-4439) (Jun. 2006).
Dumortier, et al., "A Review of Poloxamer 407; Pharmaceutical and Pharmacological Characteristics",; Pharmaceutical Research, Kluwer Academic Publishersplenum Publishers. NL,; vol. 23, No. 12, 11, pp. 2709-2728, XP019453318, ISSN: 1573-904X, DOI: 1 0.1 007/811 095-006-91 04-4 (Nov. 2006).
Eurasian Search Report, Serial No. 201291068, dated May 29, 2013 with English translation (3 pages).
European Supplementary Search Report, Application No. EP09824320, dated Mar. 28, 2012 (12 pages).
FDA, Color Additive Status List, http://www.cfsanJda.gov/-dms/opa-appc.html, downloaded Jun. 18, 2008 (13 pages).
FDA, Product Classification Database Search, http://www.accessdata.fda.gov/scripts/cdrh/cfdocs/cfpcd/classificiation/c.f?ID-3964, Device: Eosin y: database, downloaded Jun. 18, 2008 (2 pages).
Fisher Scientific, "Material Safety Data Sheet: Sodium acetate buffer," https://fscimagef.fishersci.com/msds/91502.htm (ACC #91502) (Apr. 13, 2000) (5 pages).
Goldberg, "Photodynamic therapy in skin rejuvenation," Clinics in Dermatology, 26(6):608-613 (2008).
Gonzales et al., "Photodynamic inactivation of microorganisms as an innovative approach to kill mucocutaneous and skin microorganisms," Giornale Italiano Di Dermatologia e Venereologia, 145, pp. 477-489 (2010).
Jankowski, et al., "The action of photosensitizers and serum in a bactericidal process. II. The effects of dyes: Hypericin, Eosin Y and Saphranine O," Polish Journal of Microbiology, 54(4):323-330 (2005).
Kelly, et al., "Combined photodynamic and photothermal induced injury enhances damage to in vivo model blood vessels," Lasers in Surgery and Medicine, 34(5):407-413 (2004).
Korb, et al., "An evaluation of the efficacy of Fluorescein, Rose Bengal, Lissamine Green, and a new dye mixture for ocular surface staining," Eye Contact Lens, Jan. 2008;34(1) 61-64. Jan. 1, 2008 (Jan. 1, 2008), XP055224976, Retrieved from the Internet: URL:http://www.ncbi.nlm.nih.gov/pubmed/181 80687 [retrieved on Nov. 2, 2015] * abstract * (1 page).
Lins, et al., "Enhancement of Antimicrobial Action of Photodynamic Therapy in the Presence of Hydrogen Peroxide," in Microbial Pathogens and Strategies for Combating Them: Science, Technology and Education, Edition: Microbiology Book Series #4, Editor: A. Mendez-Vilas, pp. 367-371 (2013) (acquired from:; https://www.researchgate.net/publication/283644315_Enhancement_of_Antimicrobial_Action_of_Photodynamic_Therapy_in_the_Presence_of;Hydrogen_Peroxide).
McCullach, et al., "Photosensitized destruction of *Chtoreiia vulgaris* by Methylene Blue or Nuclear Fast Red combined with hydrogen peroxide under visible light irradiation," Environmental Science and Technology, 40(7):2421-2425 (2006).
Meisel, et al., "Photodynamic therapy for periodontal diseases: state of the art," Journal of Photochemistry and Photobiology B: Biology, 79:159-170 (2005).
Mintel, "Active Plus Deep Cleaning Tablets," Database GNPD [Online].; May 2007, XP002769877, Database accession No. 707-777 *Ingredients*.
Mintel, "Effervescent Tablets," Database GNPD [Online] ; May 2009, XP002769876, Database accession No. 1089966 *Ingredients*.
Mintel, "Gel Blush," http://gnpd.com; Jun. 2009 (4 pages).
Mintel, "Gold Bear Gums," http://gnpd.com, Feb. 2008 (3 pages).
Mintel, "Photo dynamic therapy SPF 30"XP002775115.; Database accession No. 1442681, pp. 1.2.3.5 (Nov. 30, 2010).
Mintel, "Teens Braces Cleaner," http://gnpd.com, Jan. 2004 (2 pages).
Mintel, "Velvet Gloss Lip Pencil," http://gnpd.com; Feb. 2011 (4 pages).
Montenegro, et al., "Model studies on the photosensitized isomerization of bixin," Journal of Agriculture and Food Chemistry, 52(2): 367-73 (2004).
Nolan et al., "The efficacy of topical hyaluronic acid in the management of oral lichen planus," Journal of Oral Pathology and Medicine, 38(3):299-303 (2006).

(56) References Cited

OTHER PUBLICATIONS

Olympus America Inc., "Special characteristics of common biological stains," http://micro.magnet.fsu.edu/primer/photomicrography/bwstainchart.html, Apr. 30, 2000 (3 pages).

PCT international Preliminary Report on Patentability and Written Opinion for international Application No. PCT/CA2013/000787, dated Nov. 27, 2013 (9 pages).

PCT International Search Report and Written Opinion for International Application No. PCT/CA2013/000786, dated Jan. 8, 2014 (16 pages).

PCT International Search Report and Written Opinion for International Application No. PCT/CA2015/000407, dated Sep. 23, 2015 (13 pages).

PCT International Search Report Corrected for international Application No. PCT/CA2014/000261, dated Jul. 23, 2014 (7 pages).

PCT International Search Report for International Application No. PCT/CA2009/001615, dated Feb. 9, 2010 (9 pages).

PCT International Search Report for International Application No. PCT/CA2010/001134, dated Oct. 8, 2010 (3 pages).

PCT International Search Report for International Application No. PCT/CA2013/000395, dated Jul. 15, 2013 (12 Pages).

PCT International Search Report for International Application No. PCT/CA2014/000536, dated Oct. 16, 2014 (7 pages).

Publication date of following document established by Internet Archive Wayback Machine (3 pages) <URL: <http://web.archive.Org/web/20090208211504/http://en.wikipedia.org/wiki/Eosin Aug. 2, 2009.

Resources: Fluorochrome absorption emission wavelengths, [Online] XP002449595 Retrieved from the Internet: URL: http://www.sciencegateway.org/resource s/fae1.htm> retrieved on Sep. 6, 2007] see p. 2: Rhodamine WT emission nm 555 p. 2 (12 pages).

Roy, et al., "Dermal wound healing is subject to redox control," Molecular Therapy, 13(1):211-220 (2006).

Sezer, et al., "Topical drug delivery using chitosan nano- and microparticles," Expert Opinion in Drug Delivery, Informa UK, 9(9):1129-1146 (2012).

Siyusareva, et al. "Spectral and Photophysical Properties of Flourone Dyes in Bio-Related Films and Methanol", Journal of Photochemistry and Photobiology A; Chemistry 208 (2009), pp. 131-140.

Steinberg, et al., "Genetic and physiological effects of noncoherent visible light combined with hydrogen peroxide on *Streptococcus mutans* in biofilm," Antimicrobial Agents and Chemotherapy, 52(7):2626-2631 (2008).

Subba, et al., "Photocataiytic transformation of dyes and by-products in the presence of hydrogen peroxide," Environmental Technology, 24(8):1025-1030 (2003).

Sun, "Lasers and light amplification in dentistry," retrieved online at http://www.sundds.comllaser/, downloaded Jun. 23, 2005 (14 pages).

Tao, et al., "Gastrointestinal Patch Systems for Oral Drug Delivery", Drug Discovery Today, vol. 10, No. 13, Jul. 2005, pp. 909-915.

Thompson, et al., "Fluorescence polarization standards for high-throughput screening and imaging," Bio Techniques, 32(2002) (5 pages).

Tsuboi et al., "Photoluminescence Properties of Fluorone Dyes in Bio-Related Films at Low Temperatures" Journal of Photochemistry and Photobiology A; Chemistry; 222 (2011) pp. 336-342.

Van Hemelrijck, et al., "Rheological characterization and permeation behavior of poloxamer 407-based systems containing 5-arinolevulinic acid for potential application in photodynamic therapy", International Journal of Pharmaceutics,: vol. 437, No. 1-2, Nov. 1, 2012 (Nov. 1, 2012), pp. 120-129,; XP055419977, Amsterdam,NL ISSN: 0378-5173, DOI: 10.1016/j.ijpharm.2012.07.048.

Supplementary European Search Report of European Patent Application No. 15855982.3, dated Apr. 3, 2018; Munich, Anna Kajzar.

English abstract provided for CN 102603232 A.

Mao, Kailiang, "Listen to Chemical Anecdotes", Distant Press, p. 219, paragraph 1 and p. 220, paragraph 3, Aug. 2007.

\* cited by examiner

FIG. 9A 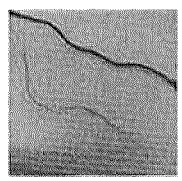 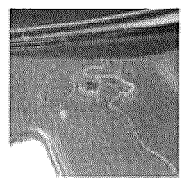 FIG. 9B
FIG. 9C 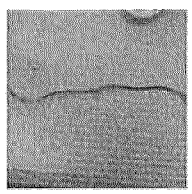 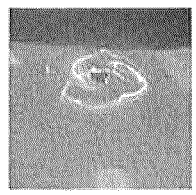 FIG. 9D
FIG. 9E 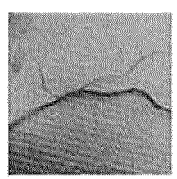 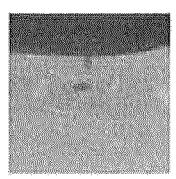 FIG. 9F
FIG. 9G 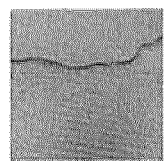  FIG. 9H
FIG. 9I 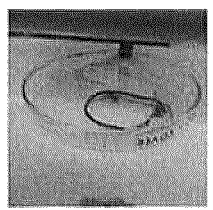 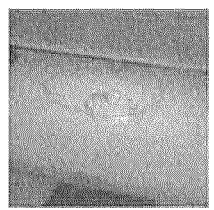 FIG. 9J FIG. 9K 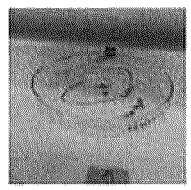 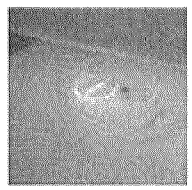 FIG. 9L
FIG. 9M 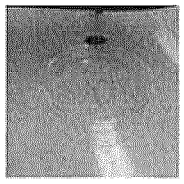 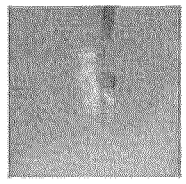 FIG. 9N
FIG. 9O 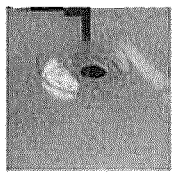 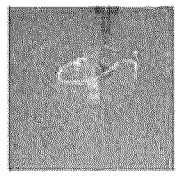 FIG. 9P

PHOTOACTIVATABLE FIBERS AND FABRIC MEDIA

CROSS-REFERENCE TO RELATED APPLICATIONS

This application is a national stage filing under 35 U.S.C. § 371 of International Application No. PCT/CA2015/051118, filed on Oct. 30, 2015, which claims the benefit of and priority to U.S. provisional patent application No. 62/073,795; filed Oct. 31, 2014. The entire contents of each of the foregoing applications are hereby incorporated by reference in their entirety. International Application No. PCT/CA2015/051118 was published under PCT Article 21(2) in English.

FIELD OF TECHNOLOGY

The present disclosure generally relates to photoactivatable fibers and fabric media comprising photoactivable agents, to methods of forming such photoactivatable fibers and fabric media, and to potential uses thereof.

BACKGROUND INFORMATION

Phototherapy has been recognized as having a wide range of applications in both the medical and cosmetic fields including use in surgery, therapy and diagnostics. For example, phototherapy has been used to treat cancers and tumors with lessened invasiveness, to disinfect target sites as an antimicrobial treatment, to treat skin conditions and to promote wound healing.

For these applications, phototherapy has typically been achieved using photoactivatable formulations and/or composition comprising photoactivatable agents capable of absorbing and/or emitting light. These photoactivatable formulations and/or compositions have typically been prepared and/or used as liquids or semi-liquids (e.g., gels, pastes, creams and the like). Due to their liquid and/or semi-liquid texture, some of these photoactivatable formulations and/or compositions exhibit leaching of the photoactivating agents out of the formulations and/or compositions. Also, these formulations and/or compositions require a support/surface onto which they can be are applied. Because they tend to spread and/or dilute in contact with fluids, some liquid and semi-liquid photoactivatable formulations and/or compositions require multiple applications onto the surface to achieve the desired effect. Therefore, the present disclosure relates to photoactivatable formulations having features that may present additional advantages over the photoactivatable formulations known to date. Such features may be useful in phototherapy and may contribute to a wider industrial applicability of the photoactivatable formulations.

SUMMARY OF DISCLOSURE

According to various aspects, the present disclosure relates to a photoactivatable fiber comprising: at least one thermoplastic polymer, and at least one photoactivatable agent; wherein the at least one photoactivatable agent absorbs and emits light between about 400 nm and about 800 nm.

According to various aspects, the present disclosure relates to a photoactivatable fabric comprising a plurality of fibers composed of at least one thermoplastic polymer; and at least one photoactivatable agent, wherein the at least one photoactivatable agent absorbs and emits light between about 400 nm and about 800 nm.

According to various aspects, the present disclosure relates to an article of manufacture comprising a photoactivatable fabric, wherein the photoactivatable fabric comprises: a) a plurality of fibers composed of at least one thermoplastic polymer; and b) at least one photoactivatable agent, wherein the at least one photoactivatable agent absorbs and emits light between about 400 nm and about 800 nm.

According to various aspects, the present disclosure relates to a method for effecting phototherapy on a subject, the method comprising applying a photoactivatable fiber as defined herein onto the subject; and illuminating the photoactivatable fiber with light having a wavelength that overlaps with an absorption spectrum of the photoactivatable agent.

According to various aspects, the present disclosure relates to a method for effecting phototherapy on a subject, the method comprising applying a photoactivatable fabric as defined herein onto the subject; and illuminating the photoactivatable fabric with light having a wavelength that overlaps with an absorption spectrum of the photoactivatable agent.

According to various aspects, the present disclosure relates to a method for effecting phototherapy on a subject, the method comprising applying an article of manufacture as defined herein onto the subject; and illuminating the article of manufacture with light having a wavelength that overlaps with an absorption spectrum of the photoactivatable agent.

According to various aspects, the present disclosure relates to the use of a photoactivatable fiber as defined herein for effecting phototherapy to a subject.

According to various aspects, the present disclosure relates to the use of a photoactivatable fabric as defined herein for effecting phototherapy to a subject.

According to various aspects, the present disclosure relates to the use of an article of manufacture as defined herein for effecting phototherapy to a subject.

According to various aspects, the present disclosure relates to an article of manufacture comprising a first photoactivatable fabric; and a second photoactivatable fabric; wherein the first and second photoactivatable fabrics are associated with one another and comprise at least one photoactivatable agent that absorbs and emits light between about 400 nm and about 800 nm.

BRIEF DESCRIPTION OF FIGURES

FIG. 1A illustrates a schematic representation of an extruder process used in the preparation of the photoactivatable fibers of the present disclosure. FIG. 1B illustrates a picture of a cross-sectional view of fibers prepared by the extrusion process according to one embodiment of the present disclosure (FIG. 1B showing the core of the fibers). FIG. 1C illustrates a picture of a cross-sectional view of fibers prepared by extrusion process according to another embodiment of the present disclosure, wherein the fibers have a sheath and a core.

FIG. 2D illustrates a graph comparing the effect of the polymers tested on fluorescence emission over time of the photoactivatable agents.

FIG. 5A illustrates a graph showing the effect of the presence of a lubricant on fluorescence emission of different concentrations of Eosin Y. FIG. 5B illustrates a graph comparing the effect of the presence of a lubricant on fluorescence emission of Eosin Y and on fluorescence emission of fluorescein.

FIG. 6A illustrates a graph comparing the fluorescence emission over time of a photoactivatable polypropylene fiber according to the present disclosure having 2, 4 or 6 layers of a EosinY:fluorescein composition on its surface. FIG. 6B illustrates a graph comparing the fluorescence emission over time of a photoactivatable nylon fiber according to an embodiment of the present disclosure having 2, 4 or 6 layers of a fluorescein composition on its surface.

FIGS. 8A and 8B show the fluorescence emission under blue lamp after one day wherein the fibers were not emerged in water. FIGS. 8C and 8D show the fluorescence emission under blue lamp after three days wherein the fibers were not emerged in water. FIGS. 8E and 8F show the fluorescence emission under blue lamp after three days emerged in water.

FIGS. 9A-9P illustrate pictures of the fluorescence emission under blue lamp of fibers dipped in a solution of photoactivatable agents, i.e., commercial dental fibers in Eosin Y 50 g/L (FIGS. 9A-9B); commercial dental fibers in Eosin Y 0.1 g/L (FIGS. 9C-9D); commercial dental fibers in fluorescein 50 g/L (FIGS. 9E-19F), commercial dental fibers in fluorescein 0.1 g/L (FIGS. 9G-9H), commercial dental fibers in fluorescein:Eosin Y 50 g/L (FIG. 9I-9J), commercial dental fibers in fluorescein:Eosin Y 0.1 g/L (FIGS. 9K-9L), polypropylene fibers in fluorescein 50 g/L (FIGS. 9M-9N), polypropylene fibers in fluorescein 0.1 g/L (FIGS. 9O-9P).

FIG. 11A illustrates a schematic representation of an article of manufacture, in occurrence a suit-like garment, according to one embodiment of the present disclosure. FIG. 11B illustrates a picture of a suit-like garment prepared with the photoactivatable fabrics according to one embodiment of the present disclosure.

DETAILED DESCRIPTION

Figure 1A:
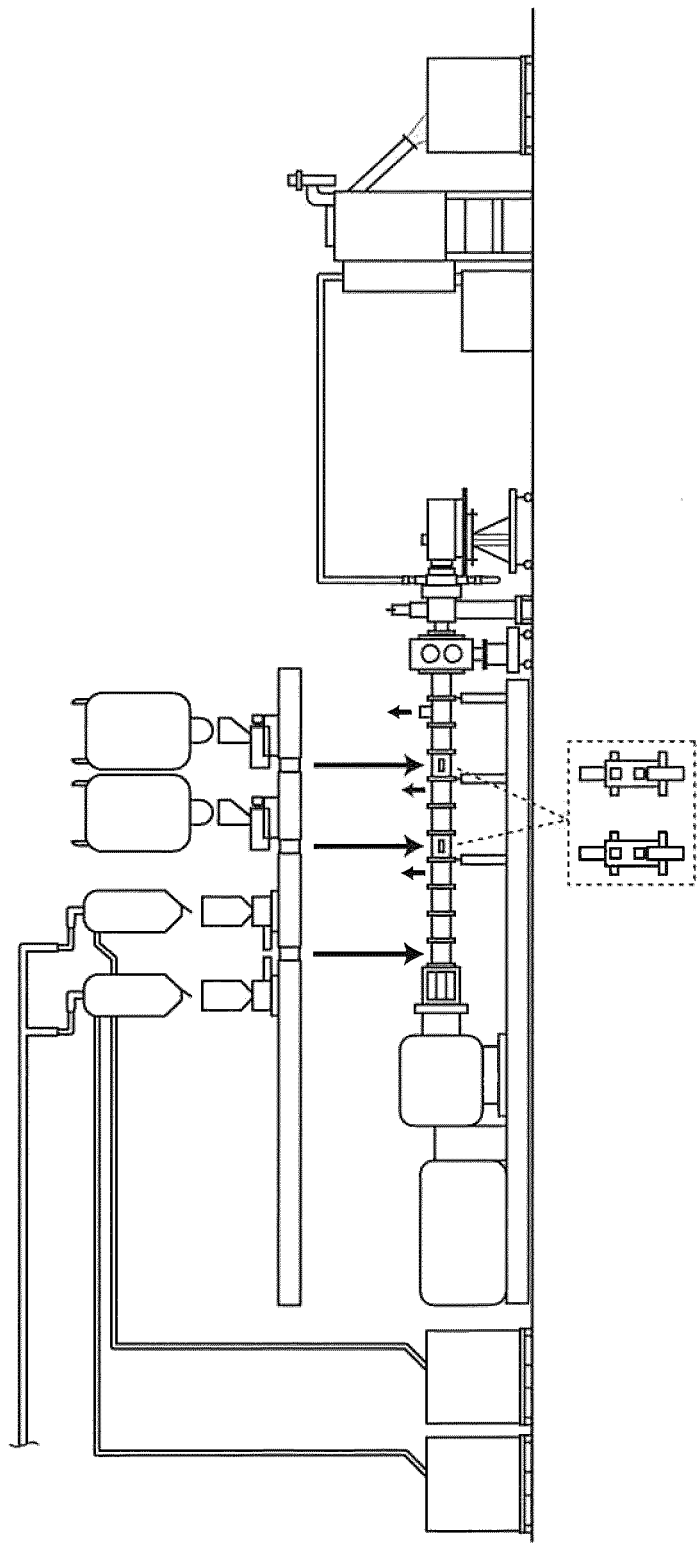
FIGS. 1A-1C.

In various aspects, the present disclosure relates to fibers and fabric media comprising photoactivatable agents and to fibers and fabric media that are photoactivatable by photoactivation of the photoactivatable agents. In some instances, the fibers and the fabric media have photoactivatable agents present on their surface (e.g., the fiber/fabric is coated or sprayed with the photoactivatable agents or the fiber/fabric is dipped into a composition or a formulation comprising the photoactivatable agent). In other instances, the photoactivatable agents are incorporated into the materials making the fibers (e.g., the photoactivatable agents are mixed/compounded with the materials making the fibers). In some other implementations, the photoactivatable agents are present both on the surface of the fiber/fabric and incorporated/compounded into the materials making the fibers.

In some instances, the fibers are, but not limited to, synthetic fibers, natural fibers, and textile fibers. For example, synthetic fibers may be made from a polymer or a combination of different polymers. In some instances, the polymer is a thermoplastic polymer.

As used herein, the term "fiber" relates to a string or a thread or a filament used as a component of composite materials. Fibers may be used in the manufacture of other materials such as for example, but not limited to, fabrics.

In some instances, the polymer is acrylic, acrylonitrile butadiene styrene (ABS), polybenzimidazole (PBI), polycarbonate, polyether sulfone (PES), polyetherether ketone (PEEK), polyetherimide (PEI), polyethylene (PE), polyphenylene oxide (PPO), polyphenylene sulfide (PPS), polypropylene (PP), polystyrene, polyvinyl chloride (PVC), teflon, polybutylene, polyethylene terephthalate (PET), polybutylene terephthalate (PBT), nylon, polylactic acid (PLA), polymethyl methacrylate polyester, polyurethane, rayons, poly(methyl methacrylate) (PMMA), or from any mixture thereof.

In some other instances, the fibers may be made from glycolic acid, copolymer lactide/glycolide, polyester polymer, copolymer polyglycolic acid/trimethylene carbonate, natural protein fiber, cellulose fiber, polyamide polymer, polymer of polypropylene, polymer of polyethylene, nylon, polymer of polylactic acid, polymer of polybutylene terephthalate, polyester, copolymer polyglycol, polybutylene, polymer of poly methyl methacrylate, or from any mixture thereof.

In some implementations, the fibers of the present disclosure may be coextruded fibers that have two distinct polymers forming the fiber, usually as a core-sheath or side-by-side.

In some implementations, the fibers may be composed of a single strand (mono-filament) or may be composed of a plurality of strands (multi-filaments). The photoactivatable fibers that are multifilament may also be intertwined or braided or twisted (i.e., the multifilaments are intertwined, braided or twisted to form the fibers).

In some implementations, the diameter of the photoactivatable fiber define herein (taken individually, monofilament) varies between about 15 microns and about 500 microns, between about 25 microns and about 500 microns, between about 50 microns and 400 microns, between about 50 microns and about 300 microns, preferably between about 50 microns and about 250 microns, preferably between about 75 microns and about 300 microns, and most preferably between about 75 microns and about 250 microns. In some specific implementations, the diameter of the photoactivatable fibers defined herein is about 15 microns, about 20 microns, about 25 microns, about 50 microns, about 75 microns, about 100 microns, about 125 microns, about 150 microns, about 175 microns, about 200 microns, about 225 microns, about 250 microns, about 250 microns, about 275 microns, about 300 microns, about 325 microns, about 350 microns, about 375 microns, about 400 microns, about 425 microns, about 450 microns, about 475 microns, about 500 microns. In some instances, the diameter of the photoactivatable fibers defined herein (taken individually) is about 31 microns.

In some implementations, the photoactivatable fibers defined herein show a medium to high resistance to mechanical pulling and stretching forces. In some implementations, the photoactivatable fibers defined here are resilient and have the ability to stretch and to reform to their original size and shape.

In some implementations, the photoactivatable fibers have a linear mass density of between about 400 and about 480 Deniers, between about 410 and about 470 Deniers, between about 420 and about 460 Deniers, between about 420 and about 450 Deniers, or about 428 Deniers. As used herein, the term "Denier" refers to a unit of measure for the linear mass density of fibers, is defined as the mass in grams per 9000 meters.

In some implementations, the fibers defined herein maintain their length and degree of flexibility and windability. In other implementation the stretch fibers may be lubricated to wind and unwind without damage being inflicted on the fibers due to the winding and the unwinding process. In some instance, the fibers have a tensile strength that allows the fibers to be stretched so as to reach a minimum diameter at least half, one third, one fourth, one fifth, one sixth, one seventh, one eight, one ninth, or one tenth of the original diameter.

FIG. 1A illustrates is a schematic representation of an example of a process for preparing photoactivatable fibers according to one embodiment of the present disclosure. In this example, an extrusion process is used wherein polymer pellets are melted and extruded and then pulled into a fiber while still hot. During this process a solution of photoactivatable agents in water and oil is sprayed onto the polymer while it is still hot. The fibers are then spun onto a bobbin for storage and ease of use. In some instances, the photoactivatable fibers of the present disclosure are prepared using a TEM co-rotating twin screw extruder.

In some implementations, the photoactivatable agent is a chemical compound which, when exposed to the light is photoexcited and can then transfer its energy to other molecules or emit it as light, such as for example fluorescence. For example, in some instances, the photoactivable agent when photoexcited by the light may transfer its energy to enhance or accelerate light dispersion or to other molecules such as oxidants to release oxygen radicals. Examples of photoactivable agents include, but are not limited to, fluorescent compounds (or stains) (also known as "fluorochromes" or "fluorophores" or "chromophores"). Other dye groups or dyes (biological and histological dyes, food colorings, carotenoids, and other dyes) can also be used. Suitable photoactivatable agent can be those that are Generally Regarded As Safe (GRAS).

In certain implementations, the photoactivatable fibers of the present disclosure comprise a first photoactivatable agent. In some implementations, the first photoactivatable agent absorbs at a wavelength in the range of the visible spectrum, such as at a wavelength of about 380 nm to about 800 nm, about 380 nm to about 700, about 400 nm to about 800, or about 380 nm to about 600 nm. In other embodiments, the first photoactivating agent absorbs at a wavelength of about 200 nm to about 800 nm, of about 200 nm to about 700 nm, of about 200 nm to about 600 nm or of about 200 nm to about 500 nm. In one embodiment, the first photoactivatable agent absorbs at a wavelength of about 200 nm to about 600 nm. In some embodiments, the first photoactivatable agent absorbs light at a wavelength of about 200 nm to about 300 nm, of about 250 nm to about 350 nm, of about 300 nm to about 400 nm, of about 350 nm to about 450 nm, of about 400 nm to about 500 nm, of about 450 nm to about 650 nm, of about 600 nm to about 700 nm, of about 650 nm to about 750 nm or of about 700 nm to about 800 nm.

In some implementations, the photoactivatable agents emit light within the range of about 400 nm and about 800 nm.

The photoactivatable fibers disclosed herein may include at least one additional photoactivatable agent. Combining photoactivatable agents may increase photo-absorption by the combined dye molecules and enhance absorption and photo-biomodulation selectivity. Thus, in certain embodiments, the photoactivatable fibers of the disclosure include more than one photoactivatable agent.

In the implementations wherein the photoactivatable fibers have the photoactivatable agent on their surface (i.e., the surface of the fibers that is in contact with the surrounding environment of the fiber), such photoactivatable fibers may be prepared by being dipped into a photoactivatable agent composition comprising one or more photoactivatable agents and a carrier material such as, but not limited to, water.

In other implementations wherein the photoactivatable fibers have the photoactivatable agent on their surface (i.e., the surface of the fibers that is in contact with the surrounding environment of the fiber), such photoactivatable fibers may be prepared by being sprayed with a photoactivatable agent composition comprising one or more photoactivatable agents and a carrier material.

In some specific examples, the photoactivatable agent composition has a consistency that allows the fibers to be dipped into the composition. In some specific examples, the photoactivatable agent composition is in a liquid or semi-liquid form.

The carrier material may be any liquid or semi liquid material that is compatible with the photoactivatable agent that is any material that does not affect the photoactive properties of the photoactivatable agent, such as, for example, water. In some other specific examples, the photoactivatable agent composition has a consistency that allows the photoactivatable agent composition to be sprayed onto the fibers.

In the implementations wherein the photoactivatable fibers have the photoactivatable agent incorporated into the fibers, the photoactivatable fibers are prepared by incorporating the photoactivatable agent into the fiber composition. In some examples, the photoactivatable fibers are prepared by extrusion. In some specific implementations, the photoactivatable fibers are prepared by a process which uses spinning. The spinning may be wet, dry, dry jet-wet, melt, gel, or electrospinning. The polymer being spun may be converted into a fluid state. If the polymer is a thermoplastic then it may be melted, otherwise it may be dissolved in a solvent or may be chemically treated to form soluble or thermoplastic derivatives. The molten polymer is then forced through the spinneret, and then it cools to a rubbery state, and then a solidified state. If a polymer solution is used, then the solvent is removed after being forced through the spinneret. A composition of the photoactivatable agent may be added to the polymer in the fluid state or to the melted polymer or to the polymer dissolved into a solvent. Melt spinning may be used for polymers that can be melted. The polymer having the photoactivatable agents dispersed therein solidifies by cooling after being extruded from the spinneret.

The photoactivatable agent may be uniformly or a non-uniformly distributed within the photoactivatable fibers. When the photoactivatable ingredient is uniformly distributed in the photoactivatable fibers, the concentration of photoactivatable agent in the photoactivatable fibers is steady as the photoactivatable fibers disintegrate, whereas when the photoactivatable agent is not uniformly distributed within the photoactivatable fibers, the concentration of the photoactivatable agent in the photoactivatable fibers varies as the photoactivatable fibers disintegrate.

The concentration of the photoactivatable agent to be used may be selected based on the desired intensity and duration of the photoactivity to be emitted from the photoactivatable fibers, and on the desired phototherapeutic, medical or cosmetic effect. For example, some dyes such as xanthene dyes reach a 'saturation concentration' after which further increases in concentration do not provide substantially higher emitted fluorescence. Further increasing the photoactivatable agent concentration above the saturation concentration can reduce the amount of activating light passing through the photoactivatable fibers. Therefore, if more fluorescence is required for a certain application than activating light, a high concentration of photoactivatable agent can be used. However, if a balance is required between the emitted fluorescence and the activating light, a concentration close to or lower than the saturation concentration can be chosen.

Suitable photoactivatable agent that may be used in the photoactivatable fibers of the present disclosure include, but are not limited to the following:

Chlorophyll dyes—chlorophyll dyes include but are not limited to chlorophyll a; chlorophyll b; chlorophyllin; bacteriochlorophyll a; bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Xanthene derivatives—xanthene dyes include but are not limited to eosin, eosin B (4',5'-dibromo, 2',7'-dinitr-o-fluorescein, dianion); eosin Y; eosin Y (2',4',5',7'-tetrabromo-fluorescein, dianion); eosin (2',4',5',7'-tetrabromo-fluorescein, dianion); eosin (2',4',5',7'-tetrabromo-fluorescein, dianion) methyl ester; eosin (2',4',5',7'-tetrabromo-fluorescein, monoanion) p-isopropylbenzyl ester; eosin derivative (2',7'-dibromo-fluorescein, dianion); eosin derivative (4',5'-dibromo-fluorescein, dianion); eosin derivative (2',7'-dichloro-fluorescein, dianion); eosin derivative (4',5'-dichloro-fluorescein, dianion); eosin derivative (2',7'-diiodo-fluorescein, dianion); eosin derivative (4',5'-diiodo-fluorescein, dianion); eosin derivative (tribromo-fluorescein, dianion); eosin derivative (2',4',5',7'-tetrachlor-o-fluorescein, dianion); eosin dicetylpyridinium chloride ion pair; erythrosin B (2',4',5',7'-tetraiodo-fluorescein, dianion); erythrosin; erythrosin dianion; erythiosin B; fluorescein; fluorescein dianion; phloxin B (2',4',5',7'-tetrabromo-3,4,5, 6-tetrachloro-fluorescein, dianion); phloxin B (tetrachloro-tetrabromo-fluorescein); phloxine B; rose bengal (3,4,5,6-tetrachloro-2',4',5',7'-tetraiodofluorescein, dianion); pyronin G, pyronin J, pyronin Y; Rhodamine dyes such as rhodamines that include, but are not limited to, 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

Methylene blue dyes—methylene blue derivatives include, but are not limited to, 1-methyl methylene blue; 1,9-dimethyl methylene blue; methylene blue; methylene blue (16 µM); methylene blue (14 µM); methylene violet; bromomethylene violet; 4-iodomethylene violet; 1,9-dimethyl-3-dimethyl-amino-7-diethyl-a-mino-phenothiazine; and 1,9-dimethyl-3-diethylamino-7-dibutyl-amino-phenothiazine.

Azo dyes—azo (or diazo-) dyes include but are not limited to methyl violet, neutral red, para red (pigment red 1), amaranth (Azorubine S), Carmoisine (azorubine, food red 3, acid red 14), allura red AC (FD&C 40), tartrazine (FD&C Yellow 5), orange G (acid orange 10), Ponceau 4R (food red 7), methyl red (acid red 2), and murexide-ammonium purpurate.

In some aspects of the disclosure, the one or more photoactivatable agents of the photoactivatable fibers disclosed herein can be independently selected from any of Acid black 1, Acid blue 22, Acid blue 93, Acid fuchsin, Acid green, Acid green 1, Acid green 5, Acid magenta, Acid orange 10, Acid red 26, Acid red 29, Acid red 44, Acid red 51, Acid red 66, Acid red 87, Acid red 91, Acid red 92, Acid red 94, Acid red 101, Acid red 103, Acid roseine, Acid rubin, Acid violet 19, Acid yellow 1, Acid yellow 9, Acid yellow 23, Acid yellow 24, Acid yellow 36, Acid yellow 73, Acid yellow S, Acridine orange, Acriflavine, Alcian blue, Alcian yellow, Alcohol soluble eosin, Alizarin, Alizarin blue 2RC, Alizarin carmine, Alizarin cyanin BBS, Alizarol cyanin R, Alizarin red S, Alizarin purpurin, Aluminon, Amido black 10B, Amidoschwarz, Aniline blue WS, Anthracene blue SWR, Auramine O, Azocannine B, Azocarmine G, Azoic diazo 5, Azoic diazo 48, Azure A, Azure B, Azure C, Basic blue 8, Basic blue 9, Basic blue 12, Basic blue 15, Basic blue 17, Basic blue 20, Basic blue 26, Basic brown 1, Basic fuchsin, Basic green 4, Basic orange 14, Basic red 2, Basic red 5, Basic red 9, Basic violet 2, Basic violet 3, Basic violet 4, Basic violet 10, Basic violet 14, Basic yellow 1, Basic yellow 2, Biebrich scarlet, Bismarck brown Y, Brilliant crystal scarlet 6R, Calcium red, Carmine, Carminic acid, Celestine blue B, China blue, Cochineal, Coelestine blue, Chrome violet CG, Chromotrope 2R, Chromoxane cyanin R, Congo corinth, Congo red, Cotton blue, Cotton red, Croceine scarlet, Crocin, Crystal ponceau 6R, Crystal violet, Dahlia, Diamond green B, Direct blue 14, Direct blue 58, Direct red, Direct red 10, Direct red 28, Direct red 80, Direct yellow 7, Eosin B, Eosin Bluish, Eosin, Eosin Y, Eosin yellowish, Eosinol, Erie garnet B, Eriochrome cyanin R, Erythrosin B, Ethyl eosin, Ethyl green, Ethyl violet, Evans blue, Fast blue B, Fast green FCF, Fast red B, Fast yellow, Fluorescein, Food green 3, Gallein, Gallamine blue, Gallocyanin, Gentian violet, Haematein, Haematine, Haematoxylin, Helio fast rubin BBL, Helvetia blue, Hematein, Hematine, Hematoxylin, Hoffman's violet, Imperial red, Indocyanin Green, Ingrain blue, Ingrain blue 1, Ingrain yellow 1, INT, Kermes, Kermesic acid, Kernechtrot, Lac, Laccaic acid, Lauth's violet, Light green, Lissamine green SF, Luxol fast blue, Magenta 0, Magenta I, Magenta II, Magenta III, Malachite green, Manchester brown, Martius yellow, Merbromin, Mercurochrome, Metanil yellow, Methylene azure A, Methylene azure B, Methylene azure C, Methylene blue, Methyl blue, Methyl green, Methyl violet, Methyl violet 2B, Methyl violet 10B, Mordant blue 3, Mordant blue 10, Mordant blue 14, Mordant blue 23, Mordant blue 32, Mordant blue 45, Mordant red 3, Mordant red 11, Mordant violet 25, Mordant violet 39 Naphthol blue black, Naphthol green B, Naphthol yellow S, Natural black 1, Natural green 3(chlorophyllin), Natural red, Natural red 3, Natural red 4, Natural red 8, Natural red 16, Natural red 25, Natural red 28, Natural yellow 6, NBT, Neutral red, New fuchsin, Niagara blue 3B, Night blue, Nile blue, Nile blue A, Nile blue oxazone, Nile blue sulphate, Nile red, Nitro BT, Nitro blue tetrazolium, Nuclear fast red, Oil red O, Orange G, Orcein, Pararosanilin, Phloxine B, Picric acid, Ponceau 2R, Ponceau 6R, Ponceau B, Ponceau de Xylidine, Ponceau S, Primula, Purpurin, Pyronin B, phycobilins, Phycocyanins, Phycoerythrins. Phycoerythrincyanin (PEC), Phthalocyanines, Pyronin G, Pyronin Y, Quinine, Rhodamine B, Rosanilin, Rose bengal, Saffron, Safranin O, Scarlet R, Scarlet red, Scharlach R, Shellac, Sirius red F3B, Solochrome cyanin R, Soluble blue, Solvent black 3, Solvent blue 38, Solvent red 23, Solvent red 24, Solvent red 27, Solvent red 45, Solvent yellow 94, Spirit soluble eosin, Sudan III, Sudan IV, Sudan black B, Sulfur yellow S, Swiss blue, Tartrazine, Thioflavine S, Thioflavine T, Thionin, Toluidine blue, Toluyline red, Tropaeolin G, Trypaflavine, Trypan blue, Uranin, Victoria blue 4R, Victoria blue B, Victoria green B, Vitamin B, Water blue I, Water soluble eosin, Xylidine ponceau, or Yellowish eosin.

In certain embodiments, the photoactivatable fibers of the present disclosure may include any of the photoactivatable agents listed above, or a combination thereof, so as to provide a synergistic biophotonic effect. For example, the following synergistic combinations of photoactivatable agents may be used: Eosin Y and Fluorescein; Fluorescein and Rose Bengal; Erythrosine in combination with Eosin Y, Rose Bengal or Fluorescein; Phloxine B in combination with one or more of Eosin Y, Rose Bengal, Fluorescein and Erythrosine; Eosin Y, Fluorescein and Rose Bengal.

In some examples, the photoactivatable agent is present in the photoactivatable agent composition at a concentration of about 100 g/L, about 50 g/L, about 10 g/L, about 5 g/L, about 1 g/L or about 0.1 g/L of the total volume. Preferably, the photoactivatable agent is present in the photoactivatable agent composition at a concentration of between about 10 g/L and about 100 g/L. In some instances, the photoactivatable agent is present in the photoactivatable agent composition at a concentration that is lower than 0.1 g/L, for example, the photoactivatable agent is present in the photoactivatable agent composition at a concentration in the milligram/L or in the microgram/L range.

In some embodiments, the photoactivatable fibers of the present disclosure comprise a lubricant. In some instances, the lubricant is coated onto the photoactivatable fibers of the present disclosure. In some instances, the lubricant is treatment oil, such as but not limited to Polyethylene glycol esters (e.g., Lurol Oil™). Without wishing to be bound by theory, the addition of a lubricant to the surface of the fibers improves the retention of the composition of photoactivatable agents onto the fibers. For example, the lubricant improves the hydrophilicity of the polymer so that it increases the absorption of the solution of photoactivatable agent.

In some implementations, there is less than about 15% leaching of the photoactivatable agent out of the photoactivatable fibers of the present disclosure, more preferably less than 10%, more preferably less than 5%, more preferably less than 4%, more preferably less than 3%, more preferably less than 2%, more preferably less than 1%, or even more preferably substantially no leaching of the photoactivatable agent out of the photoactivatable fibers. Leaching of the photoactivatable agent out of the photoactivatable fibers of the present disclosure may be assessed by placing 0.1 g of the photoactivatable fibers in 10 ml of water for 1 day and by then measuring the amount of photoactivatable agent in the water.

In some implementations, the photoactivatable fibers as defined herein may be woven into a fabric material resulting in a photoactivatable fabric comprising a plurality of photoactivatable fibers. In some implementations, the photoactivatable fabric comprising the photoactivatable fibers exhibits substantially no leaching of the photoactivatable agent.

As used herein, the term "fabric" relates to a woven material composed of a network of fibers or to a non-woven (e.g., spunbound) material composed of fibers. Weaving is a method of textile production in which two distinct sets of yarns or threads are interlaced at right angles to form a fabric or cloth. Similar methods are knitting, felting, and braiding or plaiting. Non-woven fabrics are broadly defined as sheet or web structures bonded together by entangling fiber or filaments mechanically, thermally or chemically. They are flat or tufted porous sheets that are made directly from separate fibers, molten plastic or plastic film. They are not made by weaving or knitting and do not require converting the fibers to yarn.

In some examples, the fabric material may be used in the fabrication of an article of manufacture such as, but not limited to, a garment, an article of clothing, a wound dressing, a towel, bedding, and the like. In some implementation the garment may be a shirt, pants, glove, mask, socks, or the like. In some instances, the photoactivatable fibers of the present disclosure are woven into a fabric material is a suit or a suit-like garment.

In the implementations wherein the photoactivatable agents are compounded with the polymer of the fibers, the fabric made from such fibers is also photoactivatable. Whereas in the implementations wherein the photoactivatable agents are not compounded with the polymer of the fibers, the fabric made from such fibers may be coated or dipped or sprayed with a photoactivatable agent composition to render the fabric photoactivatable.

In some other examples, the photoactivatable fabric may be a nonwoven photoactivatable fabric such as but not limited to a spunbound fabric. Spunbond fabrics may be produced by depositing extruded, spun filaments onto a collecting belt in a uniform random manner followed by bonding the fibers. The fibers may be separated during the web laying process by air jets or electrostatic charges. The collecting surface is usually perforated to prevent the air stream from deflecting and carrying the fibers in an uncontrolled manner. Bonding imparts strength and integrity to the web by applying heated rolls or hot needles to partially melt the polymer and fuse the fibers together. In general, high molecular weight and broad molecular weight distribution polymers such as, but not limited to, polypropylene, polyester, polyethylene, polyethylene terephthalate, nylon, polyurethane, and rayons may be used in the manufacture of spunbound fabrics. In some instances, spunbound fabrics may be composed of a mixture of polymers. A lower melting polymer can function as the binder which may be a separate fiber interspersed with higher melting fibers, or two polymers may be combined into a single fiber type. In the latter case the so-called bi-component fibers possess a lower melting component, which acts as a sheath covering over a higher melting core. Bicomponent fibers may also spun by extrusion of two adjacent polymers.

In some instances, spunbonding may combine fiber spinning with web formation by placing the bonding device in line with spinning. In some arrangements the web may be bonded in a separate step. The spinning process may be similar to the production of continuous filament yarns and may utilize similar extruder conditions for a given polymer. Fibers are formed as the molten polymer exits the spinnerets and is quenched by cool air. The objective of the process is to produce a wide web and, therefore, many spinnerets are placed side by side to generate sufficient fibers across the total width.

Before deposition on a moving belt or screen, the output of a spinneret usually includes a plurality of individual filaments which must be attenuated to orient molecular chains within the fibers to increase fiber strength and decrease extensibility. This is accomplished by rapidly stretching the plastic fibers immediately after exiting the spinneret. In practice the fibers are accelerated either mechanically or pneumatically. The web is formed by the pneumatic deposition of the filament bundles onto the moving belt. A pneumatic gun uses high-pressure air to move the filaments through a constricted area of lower pressure, but higher velocity as in a venturi tube. In order for the web to achieve maximum uniformity and cover, individual filaments are separated before reaching the belt. This is accomplished by inducing an electrostatic charge onto the bundle while under tension and before deposition. The charge may be induced triboelectrically or by applying a high voltage charge. The belt is usually made of an electrically grounded conductive wire. Upon deposition, the belt discharges the filaments. Webs produced by spinning linearly arranged filaments through a so-called slot die eliminating the need for such bundle separating devices.

Many methods can be used to bond the fibers in the spun web. These include mechanical needling, thermal bonding, and chemical bonding. The last two may bond large regions (area bonding) or small regions (point bonding) of the web by fusion or adhesion of fibers. Point bonding results in the fusion of fibers at points, with fibers between the point bonds remaining relatively free. Other methods used with staple fiber webs, but not routinely with continuous filament webs include stitch bonding, ultrasonic fusing, and hydraulic entanglement.

The photoactivatable fabrics of the present disclosure preferably have a thickness that allows light to reach the photoactivatable agents embedded in the fibers of the fabric and for the light emitted by the photoactivatable agents to exit the fabric.

In some embodiments, the photoactivatable fibers and the photoactivatable fabrics of the present disclosure may have cosmetic and/or medical benefits.

In some implementations of these embodiments, the photoactivatable fibers and the photoactivatable fabrics may be used to promote prevention and/or treatment of a tissue or an organ and/or to treat a tissue or an organ of a subject in need of phototherapy.

In some instances, the photoactivatable fibers and/fabrics of the present disclosure may be used to promote treatment of a skin disorder such as acne, eczema, dermatitis or psoriasis, promote tissue repair, and modulate inflammation, modulate collagen synthesis, reduce or avoid scarring, for cosmesis, or promote wound healing. They can be used to treat acute inflammation. Acute inflammation can present itself as pain, heat, redness, swelling and loss of function, and includes inflammatory responses such as those seen in allergic reactions such as those to insect bites e.g.; mosquito, bees, wasps, poison ivy, or post-ablative treatment.

In certain instance, the photoactivatable fibers and/fabrics of the present disclosure may provide treatment of a skin disorder, preventing or treating scarring, and/or accelerating wound healing and/or tissue repair.

In certain embodiments, the photoactivatable fibers or fabrics may be used to promote wound healing. In this case, the photoactivatable fibers or fabrics may be applied at wound site as deemed appropriate by the physician or other health care providers. In certain embodiments, the photoactivatable fibers or fabrics may be used following wound closure to optimize scar revision. In this case, the photoactivatable fibers or fabrics may be applied at regular intervals such as once a week, or at an interval deemed appropriate by the physician or other health care providers.

In certain embodiments, the photoactivatable fibers or fabrics may be used following acne treatment to maintain the condition of the treated skin. In this case, the photoactivatable fibers or fabrics may be applied at regular intervals such as once a week, or at an interval deemed appropriate by the physician or other health care providers.

In certain embodiments, the photoactivatable fibers or fabrics may be used following ablative skin treatment to maintain the condition of the treated skin.

The photoactivatable fibers or fabrics of the present disclosure may be used to treat skin disorders that include, but are not limited to, erythema, telangiectasia, actinic telangiectasia, basal cell carcinoma, contact dermatitis, dermatofibrosarcoma protuberans, genital warts, hidradenitis suppurativa, melanoma, merkel cell carcinoma, nummular dermatitis, molloscum contagiosum, psoriasis, psoriatic arthritis, rosacea, scabies, scalp psoriasis, sebaceous carcinoma, squamous cell carcinoma, seborrheic dermatitis, seborrheic keratosis, shingles, tinea versicolor, warts, skin cancer, pemphigus, sunburn, dermatitis, eczema, rashes, impetigo, lichen simplex chronicus, rhinophyma, perioral dermatitis, pseudofolliculitis barbae, drug eruptions, erythema multiforme, erythema nodosum, granuloma annulare, actinic keratosis, purpura, alopecia areata, aphthous stomatitis, dry skin, chapping, xerosis, fungal infections, herpes simplex, intertrigo, keloids, keratoses, milia, moluscum contagiosum, pityriasis rosea, pruritus, urticaria, and vascular tumors and malformations. Dermatitis includes contact dermatitis, atopic dermatitis, seborrheic dermatitis, nummular dermatitis, generalized exfoliative dermatitis, and statis dermatitis. Skin cancers include melanoma, basal cell carcinoma, and squamous cell carcinoma.

The photoactivatable fibers or fabrics of the present disclosure may be used to treat acne. As used herein, "acne" means a disorder of the skin caused by inflammation of skin glands or hair follicles. The photoactivatable fibers or fabrics of the disclosure can be used to treat acne at early pre-emergent stages or later stages where lesions from acne are visible. Mild, moderate and severe acne can be treated with embodiments of photoactivatable fibers or fabrics. Early pre-emergent stages of acne usually begin with an excessive secretion of sebum or dermal oil from the sebaceous glands located in the pilosebaceous apparatus. Sebum reaches the skin surface through the duct of the hair follicle. The presence of excessive amounts of sebum in the duct and on the skin tends to obstruct or stagnate the normal flow of sebum from the follicular duct, thus producing a thickening and solidification of the sebum to create a solid plug known as a comedone. In the normal sequence of developing acne, hyperkeratinazation of the follicular opening is stimulated, thus completing blocking of the duct. The usual results are papules, pustules, or cysts, often contaminated with bacteria, which cause secondary infections. Acne is characterized particularly by the presence of comedones, inflammatory papules, or cysts. The appearance of acne may range from slight skin irritation to pitting and even the development of disfiguring scars. Accordingly, the photoactivatable fibers or fabrics of the present disclosure can be used to treat one or more of skin irritation, pitting, development of scars, comedones, inflammatory papules, cysts, hyperkeratinazation, and thickening and hardening of sebum associated with acne.

Some skin disorders present various symptoms including redness, flushing, burning, scaling, pimples, papules, pustules, comedones, macules, nodules, vesicles, blisters, telangiectasia, spider veins, sores, surface irritations or pain, itching, inflammation, red, purple, or blue patches or discolorations, moles, and/or tumors.

The photoactivatable fibers or fabrics of the present disclosure may be used to treat various types of acne. Some types of acne include, for example, acne vulgaris, cystic acne, acne atrophica, bromide acne, chlorine acne, acne conglobata, acne cosmetica, acne detergicans, epidemic acne, acne estivalis, acne fulminans, halogen acne, acne indurata, iodide acne, acne keloid, acne mechanica, acne papulosa, pomade acne, premenstral acne, acne pustulosa, acne scorbutica, acne scrofulosorum, acne urticata, acne varioliformis, acne venenata, propionic acne, acne excoriee, gram negative acne, steroid acne, and nodulocystic acne.

In certain embodiments, the photoactivatable fibers or fabrics of the present disclosure are used in conjunction with systemic or topical antibiotic treatment. For example, antibiotics used to treat acne include tetracycline, erythromycin, minocycline, doxycycline. In some implementations, the article of manufacture being composed of the photoactivatable fabric of the present disclosure may have an anti-infective effect, for example when used in the treatment of a wound to prevent infection and/or re-infection of the wound by bacteria or by other infective agents.

The photoactivatable fibers or fabrics of the present disclosure may be used to treat wounds, promote wound healing, promote tissue repair and/or prevent or reduce cosmesis including improvement of motor function (e.g. movement of joints). Wounds that may be treated by the photoactivatable fibers and fabrics of the present disclosure include, for example, injuries to the skin and subcutaneous tissue initiated in different ways (e.g., pressure ulcers from extended bed rest, wounds induced by trauma or surgery, burns, ulcers linked to diabetes or venous insufficiency) and with varying characteristics. In certain embodiments, the present disclosure provides photoactivatable fibers or fabrics for treating and/or promoting the healing of, for example, burns, incisions, excisions, lesions, lacerations, abrasions, puncture or penetrating wounds, surgical wounds, contusions, hematomas, crushing injuries, amputations, sores and ulcers.

In some embodiments, the photoactivatable fibers and fabrics of the present disclosure may be used in a method for effecting phototherapy on a subject, such as on a tissue and/or an organ of the subject. Such method comprises the step of applying a photoactivatable fibers and fabric as defined herein onto the subject or onto the tissue or the organ in need of phototherapy and the step of illuminating the photoactivatable fiber and fabric with light having a wavelength that overlaps with that overlaps with an absorption spectrum of the photoactivatable agent.

In certain instances, the photoactivatable fibers and fabrics of the present disclosure may be used in phototherapy and/or in biophotonic therapy. In certain instances, the photoactivatable fibers and fabrics of the present disclosure may be used as biophotonic medical devices.

In certain instances, the photoactivatable fibers and fabrics of the present disclosure may be used in the manufacture of medical devices such as suture materials, stents, catheter, balloons, wound dressing or the like. In some other embodiments, the photoactivatable fibers may be used in the fabrication of dental care devices such as in the fabrication of toothbrush, dental floss, braces and the like.

The methods of the present disclosure comprise applying a photoactivatable fiber or photoactivatale fabric of the present disclosure to a tissue or organ in need of phototherapy and illuminating the photoactivatable fiber or photoactivatale fabric with light having a wavelength that overlaps with an absorption spectrum of the photoactivatable agent(s) present in the photoactivatable fiber or photoactivatable fabric to induce emission of the photoactivatable agent(s).

In the methods of the present disclosure, any source of actinic light can be used. Any type of halogen, LED or plasma arc lamp, or laser may be suitable. The primary characteristic of suitable sources of actinic light will be that they emit light in a wavelength (or wavelengths) appropriate for activating the one or more photoactivatable agent present in the composition. In one embodiment, an argon laser is used. In another embodiment, a potassium-titanyl phosphate (KTP) laser (e.g. a GreenLight™ laser) is used. In yet another embodiment, a LED lamp such as a photocuring device is the source of the actinic light. In yet another embodiment, the source of the actinic light is a source of light having a wavelength between about 200 to 800 nm. In another embodiment, the source of the actinic light is a source of visible light having a wavelength between about 400 and 600 nm. In another embodiment, the source of the actinic light is a source of visible light having a wavelength between about 400 and 700 nm. In yet another embodiment, the source of the actinic light is blue light. In yet another embodiment, the source of the actinic light is red light. In yet another embodiment, the source of the actinic light is green light. Furthermore, the source of actinic light should have a suitable power density. Suitable power density for non-collimated light sources (LED, halogen or plasma lamps) are in the range from about 0.1 mW/cm$^2$ to about 200 mW/cm$^2$. Suitable power density for laser light sources are in the range from about 0.5 mW/cm$^2$ to about 0.8 mW/cm$^2$.

In some implementations, the light has an energy at the subject's skin surface of between about 0.1 mW/cm$^2$ and about 500 mW/cm$^2$, or 0.1-300 mW/cm$^2$, or 0.1-200 mW/cm$^2$, wherein the energy applied depends at least on the condition being treated, the wavelength of the light, the distance of the skin from the light source and the thickness of the photoactivatable fibers or fabrics. In certain embodiments, the light at the subject's skin is between about 1-40 mW/cm$^2$, or between about 20-60 mW/cm$^2$, or between about 40-80 mW/cm$^2$, or between about 60-100 mW/cm$^2$, or between about 80-120 mW/cm$^2$, or between about 100-140 mW/cm$^2$, or between about 30-180 mW/cm$^2$, or between about 120-160 mW/cm$^2$, or between about 140-180 mW/cm$^2$, or between about 160-200 mW/cm$^2$, or between about 110-240 mW/cm$^2$, or between about 110-150 mW/cm$^2$, or between about 190-240 mW/cm$^2$.

The activation of the photoactivatable agents may take place almost immediately on illumination (femto- or pico seconds). A prolonged exposure period may be beneficial to exploit the synergistic effects of the absorbed, reflected and reemitted light of the photoactivatable fibers and fabrics of the present disclosure and its interaction with the tissue being treated. In one embodiment, the time of exposure of photoactivatable fibers or fabrics to actinic light is a period between 0.01 minutes and 90 minutes. In another embodiment, the time of exposure of the photoactivatable fibers or fabrics to actinic light is a period between 1 minute and 5 minutes. In some other embodiments, the photoactivatable fibers or fabrics are illuminated for a period between 1 minute and 3 minutes. In certain embodiments, light is applied for a period of about 1-30 seconds, about 15-45 seconds, about 30-60 seconds, about 0.75-1.5 minutes, about 1-2 minutes, about 1.5-2.5 minutes, about 2-3 minutes, about 2.5-3.5 minutes, about 3-4 minutes, about 3.5-4.5 minutes, about 4-5 minutes, about 5-10 minutes, about 10-15 minutes, about 15-20 minutes, or about 20-30 minutes. The treatment time may range up to about 90 minutes, about 80 minutes, about 70 minutes, about 60 minutes, about 50 minutes, about 40 minutes or about 30 minutes. It will be appreciated that the treatment time can be adjusted in order to maintain a dosage by adjusting the rate of fluence delivered to a treatment area. For example, the delivered fluence may be about 4 to about 60 $J/cm^2$, 4 to about 90 $J/cm^2$, 10 to about 90 $J/cm^2$, about 10 to about 60 $J/cm^2$, about 10 to about 50 $J/cm^2$, about 10 to about 40 $J/cm^2$, about 10 to about 30 $J/cm^2$, about 20 to about 40 $J/cm^2$, about 15 $J/cm^2$ to 25 $J/cm^2$, or about 10 to about 20 $J/cm^2$.

In certain embodiments, the photoactivatable fibers and photoactivatable fabric may be re-illuminated at certain intervals. In yet another embodiment, the source of actinic light is in continuous motion over the treated area for the appropriate time of exposure. In yet another embodiment, the photoactivatable fibers or photoactivatable fabric may be illuminated until the photoactivatable fibers or photoactivatable fabric is at least partially photobleached or fully photobleached.

In certain embodiments, the photoactivatable agents in the photoactivatable fibers or fabrics can be photoexcited by ambient light including from the sun and overhead lighting. In certain embodiments, the photoactivatable agents can be photoactivated by light in the visible range of the electromagnetic spectrum. The light can be emitted by any light source such as sunlight, light bulb, an LED device, electronic display screens such as on a television, computer, telephone, mobile device, flashlights on mobile devices. In the methods of the present disclosure, any source of light can be used. For example, a combination of ambient light and direct sunlight or direct artificial light may be used. Ambient light can include overhead lighting such as LED bulbs, fluorescent bulbs, and indirect sunlight.

In the methods of the present disclosure, the photoactivatable fibers or fabric may be removed from the tissue or organ following application of light. In other embodiments, the photoactivatable fibers or fabric may be left on the tissue or organ for an extended period of time and re-activated with direct or ambient light at appropriate times to treat the condition.

EXAMPLES

Example 1

Preparation of Photoactivatable Fibers and Photoactivatable Fabrics

Chromophores were incorporated into fibers made of polymer materials (polymer materials compounded with chromophores). The compounding involved taking a polymer melt and adding the chromophores in their solid form directly to the polymer, and then allowing the melt to cool. This process allowed chromophores to be integrated with the polymer fibers. The polymer fibers were selected from fibers, nonwoven fabrics, tubes and films. The chromophore to polymer ratio was selected so as to be dependent on the chromophore used, for example: for Eosin Y, 20% w/w ratio (in water) was used for the master chromophore batch, for Fluorescein, 5% w/w ratio was used for the master chromophore batch. A pure Eosin Y fiber was made and a 4:1 mixture (by weight (or 1:1 by fiber weight)) of Eosin Y and Fluorescein was made.

Figure 1B:
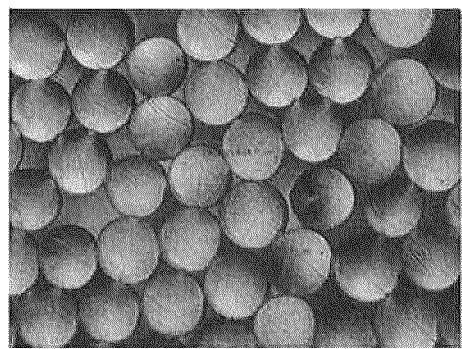
Figure 1C:
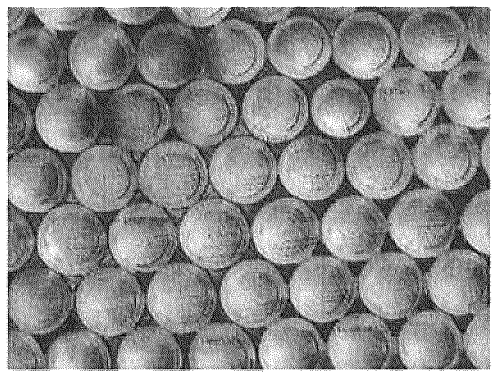

Preparation of the Fibers:

Fibers made of polypropylene, of polyethylene, nylon, or of a combination thereof were prepared. Eosin Y or fluorescein or a combination of Eosin Y and fluorescein were used as photoactivatable agents. A cross-sectional view of the fibers prepared using one type of polymer is shown in FIG. 1B. The polyethylene was made into a 50/50 polyethylene core with a polypropylene sheath. A cross-sectional view of these fibers is shown in FIG. 1C.

Fibers having the following composition have been considered:
A) Polypropylene polymer and 5% Eosin Y,
B) Polypropylene polymer and 10% Eosin Y,
C) Polypropylene polymer and 15% Eosin Y,
D) Polypropylene polymer and 20% Eosin Y,
E) Polypropylene polymer and 5% Eosin Y
F) Polypropylene polymer and 10% Fluorescein,
G) Polypropylene polymer and 15% Eosin Y;
H) Polypropylene polymer and 20% Eosin Y
I) Polyethylene polymer and 5% Eosin Y,
J) Polyethylene polymer and 10% Eosin Y,
K) Polyethylene polymer and 15% Eosin Y,
L) Polyethylene polymer and 20% Eosin Y,
M) Polyethylene polymer and 5% Fluorescein,
N) Nylon and 5% Eosin Y,
O) Nylon and 10% Eosin Y,
P) Nylon and 15% Eosin Y,
Q) Nylon and 20% Eosin Y,
R) Nylon and 5% Fluorescein.

Non-Woven Fabric:

Polypropylene fibers were used as non-woven samples. The following fibers were prepared:
S) Polypropylene polymer and 0.5 g/L Eosin Y,
T) Polypropylene polymer and 0.5 g/L Eosin Y and 0.25 g/L fluorescein.

Example 2

Preparation of Photoactivatable Fibers with Lubricant

Fibers were dipped in a bath of chromophore and lubricant (1:6 oil:water) (i.e., lurol oil) to produce fibers that were colored and that fluoresced. The fibers incorporated two chromophores, both Eosin Y and a fluorescein/Eosin Y mixture (1/4). The polyethylene was made into a 50/50 polyethylene core with a polypropylene sheath.

Fibers having the following composition have been considered:
AA) Polymethyl methacrylate (Sheath) with Polypropylene (Core), Eosin Y:Fluorescein 10 g/L each, 150 micron monofilament,
BB) Polymethyl methacrylate (Sheath) with Polypropylene (Core), Eosin Y:Fluorescein 20 g/L each, 150 micron monofilament,
CC) Polymethyl methacrylate (Sheath) with Polypropylene (Core), Eosin Y:Fluorescein 30 g/L each, 150 micron monofilament,
DD) Nylon, Eosin Y:Fluorescein 10 g/L each, 150 micron multifilament,
EE) Nylon, Eosin Y:Fluorescein 20 g/L each, 150 micron multifilament,
FF) Nylon, Eosin Y: Fluorescein 50 g/L each, 150 micron multifilament,
GG) Polypropylene, Eosin Y Chromophore 20%, 2 pounds, HH) Polypropylene, Eosin Y Chromophore 20%, 1 pounds MIXED WITH polypropylene, Fluorescein Chromophore 5%, 1 pounds (1:1 Ratio) Polyethylene Sheath doped with, Eosin Y Chromophore 20%, 1 pound AND polypropylene Core blank, Blank, 1 pound, II) Polyethylene Sheath doped with, Eosin Y Chromophore 20%, 0.5 pounds MIXED WITH polyethylene Sheath doped with, Fluorescein Chromophore 5%, 0.5 pounds (1:1 Ratio), JJ) Polypropylene Core blank, Blank, 1 pound, KK) Polyethylene Sheath doped with, Eosin Y Chromophore 20%, 1 pound AND polypropylene Core doped with, Eosin Y Chromophore 20%, 1 pound, LL) Polyethylene Sheath doped with, Eosin Y Chromophore 20%, 0.5 pounds MIXED WITH polyethylene Sheath doped with, Fluorescein Chromophore 5%, 0.5 pounds (1:1 Ratio) AND polypropylene Core doped with, Eosin Y Chromophore 20%, 1 pound, MM) Polyethylene Sheath doped with, Eosin Y Chromophore 20%, 0.5 pounds MIXED WITH polyethylene Sheath doped with, Fluorescein Chromophore 5%, 0.5 pounds (1:1 Ratio) AND polypropylene Core doped with, Eosin Y Chromophore 20%, 0.5 pounds MIXED WITH polypropylene Core doped with, Fluorescein Chromophore 5%, 0.5 pounds (1:1 Ratio), NN) Polyethylene Sheath blank, Blank, 1 pound WITH polypropylene Core doped with, Eosin Y Chromophore 20%, 1 pound, OO) Polyethylene Sheath blank, Blank, 1 pound AND polypropylene core doped with, Eosin Y Chromophore 20%, 0.5 pounds MIXED WITH polypropylene core doped with, Fluorescein Chromophore 5%, 0.5 pounds (1:1 Ratio), PP) Polyethylene Sheath doped with, Eosin Y Chromophore 20%, 1 pound AND polypropylene core doped with, Eosin Y Chromophore 20%, 0.5 pound MIXED WITH polypropylene core doped with, Fluorescein Chromophore 5%, 0.5 pounds (1:1 Ratio)

QQ) Nylon, Eosin Y Chromophore 20%, 2 pounds,

RR) Nylon, Eosin Y Chromophore 20%, 1 pound MIXED WITH Nylon, Fluorescein Chromophore 5%, 1 pound (1:1 Ratio).

Example 3

Fluorescence Emission by Photoactivatable Fibers

Figure 2A:
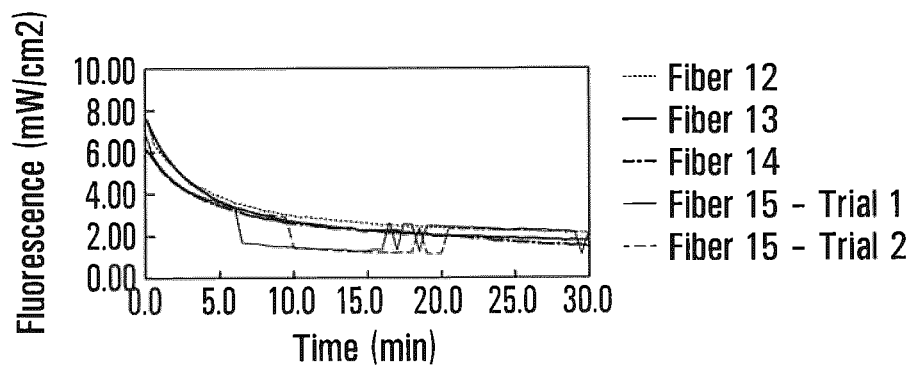
FIGS. 2A-2D illustrate graphs showing the fluorescence emission over time of a photoactivatable agent present in nylon fibers (FIG. 2A), PBT fibers (FIG. 2B), and PMMA fibers (FIG. 2C).
Figure 2B:
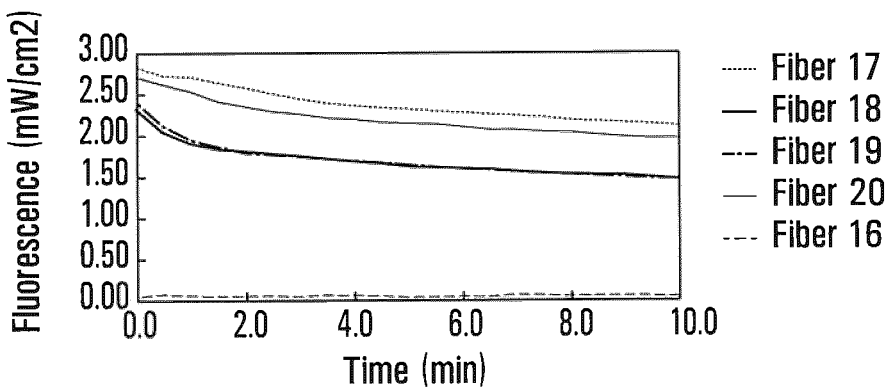
Figure 2C:
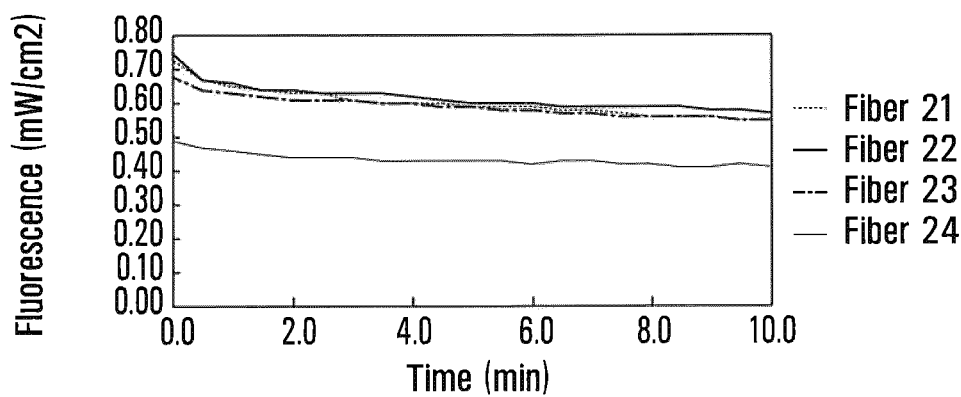

The photoactivatable fibers outlined in Tables 1, 5, 9, 14, 19 and 25 were prepared; a composition of photoactivatable agents was sprayed onto some of the fibers. Each of these fibers was assessed for its ability to emit fluorescence following illumination for 5 mins at 5 cm using a Thera™ Lamp. The results are presented in FIG. 2A (nylon fibers), FIG. 2B (PBT fibers) and FIG. 2C (PMMA fibers) and in Tables 2, 3, 4, 6, 7, 8, 10, 11, 12, 13, 15, 16, 17, 18, 20, 21, 22, 23, 24, 26, 27, 28, 29, 30, 31, 32 and 33.

TABLE 1

Photoactivatable fibers comprising polyethylene compounded with Eosin

| Fiber | Composition | Fluorescence Emission |
|---|---|---|
| 1 | Polyethylene with 0.5% Eosin + Lurol Oil Coating | Table 2 |
| 2 | Polyethylene with 0.5% Eosin + 1% Urea Peroxide Coating + Lurol Oil Coating | Table 3 |
| 3 | Polyethylene with 0.5% Eosin + Sodium Bicarbonate Coating + Lurol Oil Coating | Table 4 |
| 4 | Polyethylene with 0.5% Eosin + 10 g/L Eosin Y Coating + Lurol Oil Coating | — |

TABLE 2

Fiber 1 - Polyethylene + Eosin Inside, Lurol Oil Outside

| Fiber 1 - Polyethylene + Eosin Inside, Lurol Oil Outside | | mW/cm2 at 5 cm | | | | | | |
|---|---|---|---|---|---|---|---|---|
| | | 0 | 0.5 min | 1 min | 1.5 min | 2 min | 2.5 min | 3 min |
| Lamp | 400-518 | 37.73 | 37.83 | 37.89 | 37.91 | 38.04 | 38.18 | 38.28 |
| Fluoresc. | 519-760 | 0.03 | 0.03 | 0.03 | 0.03 | 0.03 | 0.03 | 0.02 |
| total | 400-760 | 37.76779 | 37.85432 | 37.9151 | 37.94457 | 38.06825 | 38.2112 | 38.30258 |
| % fluorescence | | 0.1% | 0.1% | 0.1% | 0.1% | 0.1% | 0.1% | 0.1% |
| purple | (400)-450 | 25.7413 | 25.4023 | 25.1707 | 24.9117 | 24.7605 | 24.6212 | 24.4817 |
| Blue | 450-500 | 11.9843 | 12.4069 | 12.6914 | 12.9768 | 13.2592 | 13.5382 | 13.7734 |
| Green | 500-570 | 0.0117 | 0.0197 | 0.0307 | 0.0279 | 0.0259 | 0.0267 | 0.0338 |
| Yellow | 570-591 | 0.0065 | 0.0067 | 0.0092 | 0.0102 | 0.0093 | 0.0092 | 0.0056 |
| Orange | 591-610 | 0.0054 | 0.0098 | 0.0088 | 0.0110 | 0.0091 | 0.0096 | 0.0064 |
| Red | 610-760 | 0.0188 | 0.0094 | 0.0047 | 0.0075 | 0.0047 | 0.0068 | 0.0019 |
| total | (400-700) | 37.77 | 37.85 | 37.92 | 37.95 | 38.07 | 38.21 | 38.30 |

TABLE 2-continued

Fiber 1 - Polyethylene + Eosin Inside, Lurol Oil Outside

| Fiber 1 - Polyethylene + Eosin Inside, Lurol Oil Outside | | mW/cm2 at 5 cm | | | | | |
|---|---|---|---|---|---|---|---|
| | | 3.5 min | 4 min | 4.5 min | 5 min | J/cm2 | |
| Lamp | 400-518 | 38.36 | 38.44 | 38.56 | 38.61 | 11.44 | 99.9% |
| Fluoresc. | 519-760 | 0.03 | 0.03 | 0.02 | 0.02 | 0.01 | 0.1% |
| total | 400-760 | 38.38788 | 38.4684 | 38.58573 | 38.6291 | 11.45 | 100.0% |
| % fluorescence | | 0.1% | 0.1% | 0.1% | 0.0% | 0.00 | 0.1% |
| purple | (400)-450 | 24.3537 | 24.2225 | 24.1625 | 24.0604 | 7.43 | 65.0% |
| Blue | 450-500 | 13.9839 | 14.1869 | 14.3716 | 14.5227 | 4.00 | 34.9% |
| Green | 500-570 | 0.0334 | 0.0415 | 0.0349 | 0.0313 | 0.01 | 0.1% |
| Yellow | 570-591 | 0.0071 | 0.0108 | 0.0064 | 0.0058 | 0.00 | 0.0% |
| Orange | 591-610 | 0.0074 | 0.0064 | 0.0072 | 0.0056 | 0.00 | 0.0% |
| Red | 610-760 | 0.0026 | 0.0005 | 0.0035 | 0.0035 | 0.00 | 0.0% |
| total | (400-700) | 38.39 | 38.47 | 38.59 | 38.63 | 11.45 | 100.0% |

TABLE 3

Fiber 2 - with Urea Peroxide in Lurol Oil

| Fiber 2 - with Urea Peroxide in Lurol Oil | | mW/cm2 at 5 cm | | | | | | |
|---|---|---|---|---|---|---|---|---|
| | | 0 | 0.5 min | 1 min | 1.5 min | 2 min | 2.5 min | 3 min |
| Lamp | 400-518 | 44.34 | 43.56 | 43.60 | 43.59 | 43.53 | 43.48 | 43.45 |
| Fluoresc. | 519-760 | 0.03 | 0.03 | 0.03 | 0.03 | 0.03 | 0.04 | 0.03 |
| total | 400-760 | 44.364 | 43.59121 | 43.63011 | 43.62437 | 43.55596 | 43.52089 | 43.48319 |
| % fluorescence | | 0.1% | 0.1% | 0.1% | 0.1% | 0.1% | 0.1% | 0.1% |
| purple | (400)-450 | 28.7823 | 27.7839 | 27.6486 | 27.3997 | 27.1146 | 26.9311 | 26.7372 |
| Blue | 450-500 | 15.5221 | 15.7414 | 15.9171 | 16.1574 | 16.3843 | 16.5173 | 16.6797 |
| Green | 500-570 | 0.0376 | 0.0415 | 0.0369 | 0.0431 | 0.0308 | 0.0436 | 0.0389 |
| Yellow | 570-591 | 0.0091 | 0.0094 | 0.0112 | 0.0094 | 0.0083 | 0.0111 | 0.0072 |
| Orange | 591-610 | 0.0076 | 0.0087 | 0.0106 | 0.0103 | 0.0099 | 0.0111 | 0.0107 |
| Red | 610-760 | 0.0055 | 0.0069 | 0.0060 | 0.0049 | 0.0085 | 0.0072 | 0.0101 |
| total | (400-700) | 44.36 | 43.59 | 43.63 | 43.62 | 43.56 | 43.52 | 43.48 |

| Fiber 2 - with Urea Peroxide in Lurol Oil | | mW/cm2 at 5 cm | | | | | |
|---|---|---|---|---|---|---|---|
| | | 3.5 min | 4 min | 4.5 min | 5 min | J/cm2 | |
| Lamp | 400-518 | 43.47 | 43.48 | 43.60 | 43.69 | 13.08 | 99.9% |
| Fluoresc. | 519-760 | 0.03 | 0.03 | 0.04 | 0.04 | 0.01 | 0.1% |
| total | 400-760 | 43.49531 | 43.50617 | 43.63938 | 43.72855 | 13.09 | 100.0% |
| % fluorescence | | 0.1% | 0.1% | 0.1% | 0.1% | 0.00 | 0.1% |
| purple | (400)-450 | 26.5918 | 26.4659 | 26.4030 | 26.3381 | 8.16 | 62.3% |
| Blue | 450-500 | 16.8401 | 16.9717 | 17.1625 | 17.3136 | 4.92 | 37.6% |
| Green | 500-570 | 0.0393 | 0.0406 | 0.0504 | 0.0474 | 0.01 | 0.1% |
| Yellow | 570-591 | 0.0093 | 0.0083 | 0.0115 | 0.0076 | 0.00 | 0.1% |
| Orange | 591-610 | 0.0100 | 0.0107 | 0.0092 | 0.0114 | 0.00 | 0.0% |
| Red | 610-760 | 0.0051 | 0.0096 | 0.0031 | 0.0110 | 0.00 | 0.0% |
| total | (400-700) | 43.50 | 43.51 | 43.64 | 43.73 | 13.09 | 100.0% |

TABLE 4

Fiber 3 - with Sodium Bicarbonate in Lurol Oil

| Fiber 3- with Sodium Bicarbonate in Lurol Oil | | mW/cm2 at 5 cm | | | | | | |
|---|---|---|---|---|---|---|---|---|
| | | 0 | 0.5 min | 1 min | 1.5 min | 2 min | 2.5 min | 3 min |
| Lamp | 400-518 | 45.77 | 45.38 | 45.39 | 45.41 | 45.38 | 45.46 | 45.53 |
| Fluoresc. | 519-760 | 0.03 | 0.03 | 0.03 | 0.02 | 0.03 | 0.03 | 0.02 |
| total | 400-760 | 45.79708 | 45.4078 | 45.42176 | 45.43369 | 45.40676 | 45.48801 | 45.55223 |
| % fluorescence | | 0.1% | 0.1% | 0.1% | 0.0% | 0.1% | 0.1% | 0.0% |

TABLE 4-continued

Fiber 3 - with Sodium Bicarbonate in Lurol Oil

| | | | | | | | |
|---|---|---|---|---|---|---|---|
| purple | (400)-450 | 30.4595 | 29.6024 | 29.2516 | 28.8436 | 28.6273 | 28.4034 | 28.2416 |
| Blue | 450-500 | 15.2759 | 15.7454 | 16.1074 | 16.5308 | 16.7115 | 17.0158 | 17.2490 |
| Green | 500-570 | 0.0356 | 0.0341 | 0.0350 | 0.0419 | 0.0480 | 0.0437 | 0.0514 |
| Yellow | 570-591 | 0.0075 | 0.0081 | 0.0062 | 0.0067 | 0.0080 | 0.0068 | 0.0031 |
| Orange | 591-610 | 0.0107 | 0.0106 | 0.0104 | 0.0063 | 0.0071 | 0.0089 | 0.0040 |
| Red | 610-760 | 0.0082 | 0.0076 | 0.0117 | 0.0046 | 0.0051 | 0.0098 | 0.0035 |
| total | (400-700) | 45.80 | 45.41 | 45.42 | 45.43 | 45.41 | 45.49 | 45.55 |

| Fiber 3- with Sodium Bicarbonate in Lurol Oil | | mW/cm2 at 5 cm | | | | | |
|---|---|---|---|---|---|---|---|
| | | 3.5 min | 4 min | 4.5 min | 5 min | J/cm2 | |
| Lamp | 400-518 | 45.55 | 45.53 | 45.53 | 45.64 | 13.65 | 99.9% |
| Fluoresc. | 519-760 | 0.03 | 0.04 | 0.02 | 0.03 | 0.01 | 0.1% |
| total | 400-760 | 45.58 | 45.56858 | 45.554 | 45.66506 | 13.66 | 100.0% |
| % fluorescence | | 0.1% | 0.1% | 0.1% | 0.1% | 0.00 | 0.1% |
| purple | (400)-450 | 28.0332 | 27.8598 | 27.6870 | 27.6032 | 8.61 | 63.0% |
| Blue | 450-500 | 17.4738 | 17.6294 | 17.7953 | 17.9823 | 5.03 | 36.8% |
| Green | 500-570 | 0.0500 | 0.0491 | 0.0580 | 0.0645 | 0.01 | 0.1% |
| Yellow | 570-591 | 0.0094 | 0.0100 | 0.0052 | 0.0053 | 0.00 | 0.0% |
| Orange | 591-610 | 0.0090 | 0.0116 | 0.0060 | 0.0060 | 0.00 | 0.0% |
| Red | 610-760 | 0.0049 | 0.0091 | 0.0026 | 0.0041 | 0.00 | 0.0% |
| total | (400-700) | 45.58 | 45.57 | 45.55 | 45.67 | 13.66 | 100.0% |

TABLE 5

Photoactivatable fibers comprising polylactic acid (PLA) compounded with Eosin

| Fiber | Composition | Fluorescence Emission |
|---|---|---|
| 5 | PLA with 0.5% Eosin + Lurol Oil Coating | Table 6 |
| 6 | PLA with 0.5% Eosin + 1% Urea Peroxide Coating + Lurol Oil Coating | Table 7 |
| 7 | PLA with 0.5% Eosin + Sodium Bicarbonate Coating + Lurol Oil Coating | Table 8 |

TABLE 6

Fiber 5 - Polylactic Acid + Eosin Inside, Lurol Oil Outside

| Fiber 5 - Polylactic Acid + Eosin Inside, Lurol Oil Outside | | mW/cm2 at 5 cm | | | | | | |
|---|---|---|---|---|---|---|---|---|
| | | 0 | 0.5 min | 1 min | 1.5 min | 2 min | 2.5 min | 3 min |
| Lamp | 400-518 | 14.94 | 14.93 | 14.85 | 14.75 | 14.71 | 14.67 | 14.65 |
| Fluoresc. | 519-760 | 1.12 | 1.02 | 0.98 | 0.95 | 0.94 | 0.92 | 0.91 |
| total | 400-760 | 16.05383 | 15.94828 | 15.82929 | 15.69884 | 15.6478 | 15.58449 | 15.56786 |
| % fluorescence | | 6.9% | 6.4% | 6.2% | 6.1% | 6.0% | 5.9% | 5.9% |
| purple | (400)-450 | 10.4182 | 10.2214 | 10.0756 | 9.9133 | 9.8031 | 9.7045 | 9.6358 |
| Blue | 450-500 | 4.5199 | 4.7079 | 4.7777 | 4.8335 | 4.9048 | 4.9608 | 5.0190 |
| Green | 500-570 | 0.1184 | 0.1103 | 0.1017 | 0.0982 | 0.0979 | 0.0945 | 0.0947 |
| Yellow | 570-591 | 0.2998 | 0.2848 | 0.2731 | 0.2668 | 0.2631 | 0.2578 | 0.2561 |
| Orange | 591-610 | 0.3337 | 0.3119 | 0.3002 | 0.2939 | 0.2891 | 0.2839 | 0.2806 |
| Red | 610-760 | 0.3793 | 0.3265 | 0.3152 | 0.3070 | 0.3035 | 0.2965 | 0.2949 |
| total | (400-700) | 16.07 | 15.96 | 15.84 | 15.71 | 15.66 | 15.60 | 15.58 |

| Fiber 5 - Polylactic Acid + Eosin Inside, Lurol Oil Outside | | mW/cm2 at 5 cm | | | | | |
|---|---|---|---|---|---|---|---|
| | | 3.5 min | 4 min | 4.5 min | 5 min | J/cm2 | |
| Lamp | 400-518 | 14.66 | 14.62 | 14.61 | 14.61 | 4.42 | 93.9% |
| Fluoresc. | 519-760 | 0.90 | 0.87 | 0.87 | 0.85 | 0.28 | 6.0% |
| total | 400-760 | 15.55919 | 15.48759 | 15.48833 | 15.46502 | 4.71 | 99.9% |

TABLE 6-continued

Fiber 5 - Polylactic Acid + Eosin Inside, Lurol Oil Outside

| | | | | | | | |
|---|---|---|---|---|---|---|---|
| % fluorescence | | 5.8% | 5.6% | 5.6% | 5.5% | 0.06 | 6.0% |
| purple | (400)-450 | 9.5792 | 9.5010 | 9.4528 | 9.4132 | 2.95 | 62.6% |
| Blue | 450-500 | 5.0769 | 5.1140 | 5.1618 | 5.1980 | 1.47 | 31.3% |
| Green | 500-570 | 0.0931 | 0.0908 | 0.0913 | 0.0890 | 0.03 | 0.6% |
| Yellow | 570-591 | 0.2523 | 0.2461 | 0.2436 | 0.2386 | 0.08 | 1.7% |
| Orange | 591-610 | 0.2780 | 0.2700 | 0.2688 | 0.2626 | 0.09 | 1.9% |
| Red | 610-760 | 0.2929 | 0.2784 | 0.2828 | 0.2761 | 0.09 | 2.0% |
| total | (400-700) | 15.57 | 15.50 | 15.50 | 15.48 | 4.71 | 100.0% |

TABLE 7

Fiber 6 - Polylactic Acid + Eosin Inside, UP + Lurol Oil Outside

| Fiber 6 - Polylactic Acid + Eosin Inside, UP + Lurol Oil Outside | | mW/cm2 at 5 cm | | | | | | |
|---|---|---|---|---|---|---|---|---|
| | | 0 | 0.5 min | 1 min | 1.5 min | 2 min | 2.5 min | 3 min |
| Lamp | 400-518 | 15.27 | 15.32 | 15.33 | 15.31 | 15.29 | 15.28 | 15.26 |
| Fluoresc. | 519-760 | 1.05 | 0.94 | 0.91 | 0.90 | 0.89 | 0.86 | 0.85 |
| total | 400-760 | 16.32258 | 16.26344 | 16.24112 | 16.20668 | 16.17224 | 16.14035 | 16.10769 |
| % fluorescence | | 6.4% | 5.8% | 5.6% | 5.6% | 5.5% | 5.3% | 5.3% |
| purple | (400)-450 | 10.6935 | 10.4773 | 10.3672 | 10.2573 | 10.1656 | 10.0862 | 10.0081 |
| Blue | 450-500 | 4.5788 | 4.8458 | 4.9628 | 5.0482 | 5.1215 | 5.1921 | 5.2499 |
| Green | 500-570 | 0.0972 | 0.0853 | 0.0822 | 0.0826 | 0.0797 | 0.0787 | 0.0778 |
| Yellow | 570-591 | 0.2906 | 0.2567 | 0.2470 | 0.2436 | 0.2380 | 0.2330 | 0.2287 |
| Orange | 591-610 | 0.3265 | 0.2930 | 0.2836 | 0.2786 | 0.2726 | 0.2664 | 0.2618 |
| Red | 610-760 | 0.3516 | 0.3193 | 0.3121 | 0.3097 | 0.3079 | 0.2968 | 0.2942 |
| total | (400-700) | 16.34 | 16.28 | 16.25 | 16.22 | 16.19 | 16.15 | 16.12 |

| Fiber 6 - Polylactic Acid + Eosin Inside, UP + Lurol Oil Outside | | mW/cm2 at 5 cm | | | | | |
|---|---|---|---|---|---|---|---|
| | | 3.5 min | 4 min | 4.5 min | 5 min | J/cm2 | |
| Lamp | 400-518 | 15.22 | 15.18 | 15.14 | 15.11 | 4.58 | 94.4% |
| Fluoresc. | 519-760 | 0.83 | 0.83 | 0.80 | 0.79 | 0.27 | 5.5% |
| total | 400-760 | 16.05246 | 16.00419 | 15.94197 | 15.8982 | 4.84 | 99.9% |
| % fluorescence | | 5.2% | 5.2% | 5.0% | 5.0% | 0.05 | 5.5% |
| purple | (400)-450 | 9.9236 | 9.8464 | 9.7768 | 9.7092 | 3.05 | 62.9% |
| Blue | 450-500 | 5.2948 | 5.3311 | 5.3629 | 5.3990 | 1.53 | 31.6% |
| Green | 500-570 | 0.0752 | 0.0752 | 0.0741 | 0.0737 | 0.02 | 0.5% |
| Yellow | 570-591 | 0.2254 | 0.2223 | 0.2162 | 0.2132 | 0.07 | 1.5% |
| Orange | 591-610 | 0.2578 | 0.2549 | 0.2474 | 0.2433 | 0.08 | 1.7% |
| Red | 610-760 | 0.2880 | 0.2866 | 0.2764 | 0.2715 | 0.09 | 1.9% |
| total | (400-700) | 16.06 | 16.02 | 15.95 | 15.91 | 4.85 | 100.0% |

TABLE 8

Fiber 7 - Polylactic Acid + Eosin Inside, Bicarb + Lurol Oil Outside

| Fiber 7 - Polylactic Acid + Eosin Inside, Bicarb + Lurol Oil Outside | | mW/cm2 at 5 cm | | | | | | |
|---|---|---|---|---|---|---|---|---|
| | | 0 | 0.5 min | 1 min | 1.5 min | 2 min | 2.5 min | 3 min |
| Lamp | 400-518 | 16.07 | 16.04 | 16.01 | 15.90 | 15.79 | 15.77 | 15.72 |
| Fluoresc. | 519-760 | 1.12 | 0.99 | 0.96 | 0.93 | 0.92 | 0.92 | 0.91 |
| total | 400-760 | 17.18991 | 17.03564 | 16.96755 | 16.83133 | 16.71217 | 16.69256 | 16.62935 |

TABLE 8-continued

Fiber 7 - Polylactic Acid + Eosin Inside, Bicarb + Lurol Oil Outside

| % fluorescence | | 6.5% | 5.8% | 5.7% | 5.5% | 5.5% | 5.5% | 5.4% |
|---|---|---|---|---|---|---|---|---|
| purple | (400)-450 | 11.1705 | 10.9276 | 10.8025 | 10.6200 | 10.4800 | 10.3930 | 10.2891 |
| Blue | 450-500 | 4.9016 | 5.1169 | 5.2034 | 5.2792 | 5.3112 | 5.3811 | 5.4351 |
| Green | 500-570 | 0.1197 | 0.1019 | 0.0951 | 0.0932 | 0.0913 | 0.0929 | 0.0918 |
| Yellow | 570-591 | 0.3141 | 0.2730 | 0.2662 | 0.2585 | 0.2557 | 0.2532 | 0.2495 |
| Orange | 591-610 | 0.3475 | 0.3054 | 0.2967 | 0.2881 | 0.2847 | 0.2817 | 0.2778 |
| Red | 610-760 | 0.3529 | 0.3253 | 0.3178 | 0.3062 | 0.3028 | 0.3042 | 0.2994 |
| total | (400-700) | 17.21 | 17.05 | 16.98 | 16.85 | 16.73 | 16.71 | 16.64 |

| Fiber 7 - Polylactic Acid + Eosin Inside, Bicarb + Lurol Oil Outside | | mW/cm2 at 5 cm | | | | | |
|---|---|---|---|---|---|---|---|
| | | 3.5 min | 4 min | 4.5 min | 5 min | J/cm2 | |
| Lamp | 400-518 | 15.6 | 15.6 | 15.70 | 15.75 | 4.75 | 94.3% |
| Fluoresc. | 519-760 | 0.89 | 0.87 | 0.87 | 0.84 | 0.28 | 5.6% |
| total | 400-760 | 16.55821 | 16.5202 | 16.56995 | 16.59658 | 5.03 | 99.9% |
| % fluorescence | | 5.4% | 5.2% | 5.2% | 5.1% | 0.06 | 5.6% |
| purple | (400)-450 | 10.1908 | 10.1298 | 10.1080 | 10.0959 | 3.15 | 62.6% |
| Blue | 450-500 | 5.4730 | 5.5252 | 5.5922 | 5.6575 | 1.60 | 31.7% |
| Green | 500-570 | 0.0894 | 0.0859 | 0.0890 | 0.0858 | 0.03 | 0.6% |
| Yellow | 570-591 | 0.2454 | 0.2382 | 0.2381 | 0.2313 | 0.08 | 1.5% |
| Orange | 591-610 | 0.2740 | 0.2670 | 0.2655 | 0.2586 | 0.09 | 1.7% |
| Red | 610-760 | 0.2988 | 0.2868 | 0.2898 | 0.2799 | 0.09 | 1.8% |
| total | (400-700) | 16.57 | 16.53 | 16.58 | 16.61 | 5.04 | 100.0% |

TABLE 9

Photoactivatable fibers comprising polypropylene compounded with Eosin

| Fiber | Composition | Fluorescence Emission |
|---|---|---|
| 8 | Polypropylene with 0.5% Eosin + Lurol Oil Coating | Table 10 |
| 9 | Polypropylene with 0.5% Eosin + 1% Urea Peroxide Coating + Lurol Oil Coating | Table 11 |
| 10 | Polypropylene with 0.5% Eosin + Sodium Bicarbonate Coating + Lurol Oil Coating | Table 12 |
| 11 | Polypropylene with 0.5% Eosin + 10 g/L Eosin Y Coating + Lurol Oil Coating | Table 13 |

TABLE 10

Fiber 8 - Polypropylene + Eosin Inside, Lurol Oil Outside

| Fiber 8 - Polypropylene + Eosin Inside, Lurol Oil | | mW/cm2 at 5 cm | | | | | | |
|---|---|---|---|---|---|---|---|---|
| | | 0 | 0.5 min | 1 min | 1.5 min | 2 min | 2.5 min | 3 min |
| Lamp | 400-518 | 38.79 | 38.50 | 38.31 | 38.11 | 37.91 | 37.60 | 37.37 |
| Fluoresc. | 519-760 | 0.10 | 0.01 | 0.01 | 0.01 | 0.01 | 0.01 | 0.01 |
| total | 400-760 | 38.887 | 38.51682 | 38.31451 | 38.11967 | 37.91618 | 37.60603 | 37.37597 |
| % fluorescence | | 0.2% | 0.0% | 0.0% | 0.0% | 0.0% | 0.0% | 0.0% |
| purple | (400)-450 | 26.213 | 25.61104 | 25.2140 | 24.8144 | 24.4722 | 24.0801 | 23.7486 |
| Blue | 450-500 | 12.5660 | 12.8714 | 13.0711 | 13.2695 | 13.4083 | 13.4929 | 13.5901 |
| Green | 500-570 | 0.01 | 0.0223 | 0.0221 | 0.0249 | 0.0289 | 0.0253 | 0.0293 |
| Yellow | 570-591 | 0.0002 | 0.0003 | 0.0006 | 0.0053 | 0.0014 | 0.0036 | 0.0021 |
| Orange | 591-610 | 0.00 | 0.0029 | 0.0044 | 0.0049 | 0.0026 | 0.0031 | 0.0030 |
| Red | 610-760 | 0.09 | 0.0096 | 0.0026 | 0.0008 | 0.0029 | 0.0012 | 0.0029 |
| total | (400-700) | 38.89 | 38.52 | 38.31 | 38.12 | 37.92 | 37.61 | 37.38 |

TABLE 10-continued

| Fiber 8 - Polypropylene + Eosin Inside, Lurol Oil Outside | | | | | | |
|---|---|---|---|---|---|---|
| Fiber 8 - Polypropylene + Eosin Inside, Lurol Oil | | mW/cm2 at 5 cm | | | | |
| | | 3.5 min | 4 min | 4.5 min | 5 min | J/cm2 |
| Lamp | 400-518 | 37.23 | 36.98 | 36.89 | 36.70 | 11.33 | 99.9% |
| Fluoresc. | 519-760 | 0.01 | 0.01 | 0.02 | 0.02 | 0.01 | 0.1% |
| total | 400-760 | 37.24258 | 36.99724 | 36.90971 | 36.7173 | 11.34 | 100.0 |
| % fluorescence | | 0.0% | 0.0% | 0.1% | 0.1% | 0.00 | 0.1% |
| purple | (400)-450 | 23.5275 | 23.2268 | 23.0455 | 22.8148 | 7.32 | 64.6% |
| Blue | 450-500 | 13.6822 | 13.7305 | 13.8151 | 13.8517 | 4.00 | 35.3% |
| Green | 500-570 | 0.0257 | 0.0272 | 0.0345 | 0.0339 | 0.01 | 0.1 |
| Yellow | 570-591 | 0.0010 | 0.0023 | 0.0053 | 0.0030 | 0.00 | 0.0% |
| Orange | 591-610 | 0.0033 | 0.0045 | 0.0032 | 0.0054 | 0.00 | 0.0 |
| Red | 610-760 | 0.0029 | 0.0061 | 0.0060 | 0.0087 | 0.00 | 0.0 |
| total | (400-700) | 37.24 | 37.00 | 36.91 | 36.72 | 11.34 | 100.0% |

TABLE 11

| Fiber 9 - Polypropylene + Eosin Inside, UP + Lurol Oil Outside | | | | | | | | |
|---|---|---|---|---|---|---|---|---|
| Fiber 9 - Polypropylene + Eosin Inside, UP + Lurol Oil Outside | | mW/cm2 at 5 cm | | | | | | |
| | | 0 | 0.5 mi | 1 min | 1.5 min | 2 mi | 2.5 min | 3 min |
| Lamp | 400-518 | 38.22 | 37.85 | 37.66 | 37.36 | 37.11 | 36.88 | 36.72 |
| Fluoresc. | 519-760 | 0.12 | 0.00 | 0.02 | 0.00 | 0.01 | 0.01 | 0.02 |
| total | 400-760 | 38.33982 | 37.8572 | 37.67632 | 37.36189 | 37.1219 | 36.89308 | 36.73885 |
| % fluorescence | | 0.3% | 0.0% | 0.0% | 0.0% | 0.0% | 0.0% | 0.0% |
| purple | (400)-450 | 25.9945 | 25.2982 | 24.9107 | 24.4318 | 24.0608 | 23.7143 | 23.4416 |
| Blue | 450-500 | 12.2258 | 12.535 | 12.7280 | 12.9008 | 13.030 | 13.1446 | 13.2552 |
| Green | 500-570 | 0.0032 | 0.0220 | 0.0210 | 0.0265 | 0.0273 | 0.0230 | 0.0278 |
| Yellow | 570-591 | 0.0007 | 0.0001 | 0.0038 | 0.0005 | 0.0004 | 0.0048 | 0.0034 |
| Orange | 591-610 | 0.0005 | 0.0003 | 0.0053 | 0.0021 | 0.0014 | 0.0052 | 0.0048 |
| Red | 610-760 | 0.1152 | 0.0014 | 0.0078 | 0.0002 | 0.0014 | 0.0014 | 0.0062 |
| total | (400-700) | 38.34 | 37.86 | 37.68 | 37.36 | 37.12 | 36.89 | 36.74 |

| Fiber 9 - Polypropylene + Eosin Inside, UP + Lurol Oil Outside | | | | | | | |
|---|---|---|---|---|---|---|---|
| | | 3.5 min | 4 min | 4.5 min | 5 min | J/cm | |
| Lamp | 400-518 | 36.64 | 36.51 | 36.43 | 36.37 | 11.14 | 99.9% |
| Fluoresc. | 519-760 | 0.01 | 0.01 | 0.01 | 0.01 | 0.01 | 0.1% |
| total | 400-760 | 36.64907 | 36.52148 | 36.44165 | 36.37409 | 11.15 | 100.0% |
| % fluorescence | | 0.0% | 0.0% | 0.0% | 0.0% | 0.00 | 0.1% |
| purple | (400)-450 | 23.2361 | 23.0084 | 22.8281 | 22.6777 | 7.23 | 64.8% |
| Blue | 450-500 | 13.3760 | 13.4809 | 13.5761 | 13.6610 | 3.91 | 35.1% |
| Green | 500-570 | 0.0285 | 0.0241 | 0.0321 | 0.0306 | 0.01 | 0.1% |
| Yellow | 570-591 | 0.0005 | 0.0029 | 0.0011 | 0.0009 | 0.00 | 0.0% |
| Orange | 591-610 | 0.0033 | 0.0033 | 0.0025 | 0.0023 | 0.00 | 0.0% |
| Red | 610-760 | 0.0048 | 0.0020 | 0.0019 | 0.0017 | 0.00 | 0.0% |
| total | (400-700) | 36.65 | 36.52 | 36.44 | 36.37 | 11.15 | 100.0% |

TABLE 12

Fiber 10 - Polypropylene + Eosin Inside, Bicarb + Lurol Oil Outside

| Fiber 10 - Polypropylene + Eosin Inside, Bicarb + Lurol Oil | | mW/cm2 at 5 cm | | | | | | |
|---|---|---|---|---|---|---|---|---|
| | | 0 | 0.5 min | 1 min | 1.5 min | 2 min | 2.5 min | 3 min |
| Lamp | 400-518 | 36.92 | 36.59 | 36.47 | 36.29 | 36.17 | 36.04 | 35.91 |
| Fluoresc. | 519-760 | 0.00 | 0.01 | 0.01 | 0.01 | 0.01 | 0.01 | 0.01 |
| total | 400-760 | 36.92294 | 36.59499 | 36.47866 | 36.30052 | 36.18347 | 36.04749 | 35.91653 |
| % fluorescence | | 0.0% | 0.0% | 0.0% | 0.0% | 0.0% | 0.0% | 0.0% |
| purple | (400)-450 | 24.9566 | 24.3430 | 24.0409 | 23.6970 | 23.4067 | 23.1523 | 22.8998 |
| Blue | 450-500 | 11.9414 | 12.2264 | 12.4073 | 12.5720 | 12.7439 | 12.8609 | 12.9852 |
| Green | 500-570 | 0.0226 | 0.0177 | 0.0253 | 0.0257 | 0.0262 | 0.0254 | 0.0258 |
| Yellow | 570-591 | 0.0012 | 0.0030 | 0.0017 | 0.0041 | 0.0026 | 0.0015 | 0.0031 |
| Orange | 591-610 | 0.0010 | 0.0035 | 0.0012 | 0.0015 | 0.0027 | 0.0031 | 0.0023 |
| Red | 610-760 | 0.0001 | 0.0015 | 0.0022 | 0.0002 | 0.0014 | 0.0043 | 0.0004 |
| total | (400-700) | 36.92 | 36.60 | 36.48 | 36.30 | 36.18 | 36.05 | 35.92 |

| Fiber 10 - Polypropylene + Eosin Inside, Bicarb + Lurol Oil | | mW/cm2 at 5 cm | | | | | |
|---|---|---|---|---|---|---|---|
| | | 3.5 min | 4 min | 4.5 min | 5 min | J/cm2 | |
| Lamp | 400-518 | 35.83 | 35.76 | 35.70 | 35.67 | 10.85 | 100.0% |
| Fluoresc. | 519-760 | 0.01 | 0.01 | 0.01 | 0.01 | 0.00 | 0.0% |
| total | 400-760 | 35.84232 | 35.77078 | 35.70893 | 35.67485 | 10.85 | 100.0% |
| % fluorescence | | 0.0% | 0.0% | 0.0% | 0.0% | 0.00 | 0.0% |
| purple | (400)-450 | 22.7089 | 22.5307 | 22.3735 | 22.2601 | 7.02 | 64.7% |
| Blue | 450-500 | 13.1015 | 13.2040 | 13.3008 | 13.3833 | 3.82 | 35.2% |
| Green | 500-570 | 0.0244 | 0.0253 | 0.0297 | 0.0281 | 0.01 | 0.1% |
| Yellow | 570-591 | 0.0012 | 0.0039 | 0.0036 | 0.0006 | 0.00 | 0.0% |
| Orange | 591-610 | 0.0031 | 0.0046 | 0.0013 | 0.0012 | 0.00 | 0.0% |
| Red | 610-760 | 0.0033 | 0.0024 | 0.0000 | 0.0015 | 0.00 | 0.0% |
| total | (400-700) | 35.84 | 35.77 | 35.71 | 35.67 | 10.85 | 100.0% |

35

TABLE 13

Fiber 11 - Polypropylene + Eosin Inside, Eosin + Lurol Oil Outside

| Fiber 11 - Polypropylene + Eosin Inside, Eosin + Lurol Oil Outside | | mW/cm2 at 5 cm | | | | | | |
|---|---|---|---|---|---|---|---|---|
| | | 0 | 0.5 min | 1 min | 1.5 min | 2 min | 2.5 min | 3 min |
| Lamp | 400-518 | 34.92 | 34.27 | 34.10 | 33.96 | 33.80 | 33.65 | 33.52 |
| Fluoresc. | 519-760 | 0.04 | 0.02 | 0.03 | 0.03 | 0.03 | 0.03 | 0.03 |
| total | 400-760 | 34.96027 | 34.29043 | 34.12328 | 33.98972 | 33.83178 | 33.67762 | 33.55483 |
| % fluorescence | | 0.1% | 0.1% | 0.1% | 0.1% | 0.1% | 0.1% | 0.1% |
| purple | (400)-450 | 24.0092 | 23.0633 | 22.6970 | 22.3805 | 22.0694 | 21.8103 | 21.5672 |
| Blue | 450-500 | 10.9008 | 11.1891 | 11.3868 | 11.5594 | 11.7112 | 11.8201 | 11.9385 |
| Green | 500-570 | 0.0173 | 0.0173 | 0.0143 | 0.0207 | 0.0223 | 0.0225 | 0.0194 |
| Yellow | 570-591 | 0.0118 | 0.0090 | 0.0071 | 0.0088 | 0.0095 | 0.0102 | 0.0076 |
| Orange | 591-610 | 0.0114 | 0.0076 | 0.0097 | 0.0112 | 0.0104 | 0.0078 | 0.0109 |
| Red | 610-760 | 0.0102 | 0.0044 | 0.0088 | 0.0097 | 0.0095 | 0.0069 | 0.0117 |
| total | (400-700) | 34.96 | 34.29 | 34.12 | 33.99 | 33.83 | 33.68 | 33.56 |

| Fiber 11 - Polypropylene + Eosin Inside, Eosin + Lurol Oil Outside | | mW/cm2 at 5 cm | | | | | |
|---|---|---|---|---|---|---|---|
| | | 3.5 min | 4 min | 4.5 min | 5 min | J/cm2 | |
| Lamp | 400-518 | 33.43 | 33.36 | 33.23 | 33.16 | 10.15 | 99.9% |
| Fluoresc. | 519-760 | 0.03 | 0.03 | 0.03 | 0.03 | 0.01 | 0.1% |
| total | 400-760 | 33.45521 | 33.38872 | 33.26012 | 33.18787 | 10.16 | 100.0% |
| % fluorescence | | 0.1% | 0.1% | 0.1% | 0.1% | 0.00 | 0.1% |

TABLE 13-continued

| Fiber 11 - Polypropylene + Eosin Inside, Eosin + Lurol Oil Outside | | | | | | | |
|---|---|---|---|---|---|---|---|
| purple | (400)-450 | 21.3650 | 21.1855 | 20.9851 | 20.8562 | 6.63 | 65.3% |
| Blue | 450-500 | 12.0429 | 12.1567 | 12.2284 | 12.2886 | 3.51 | 34.5% |
| Green | 500-570 | 0.0232 | 0.0196 | 0.0235 | 0.0199 | 0.01 | 0.1% |
| Yellow | 570-591 | 0.0079 | 0.0079 | 0.0075 | 0.0085 | 0.00 | 0.0% |
| Orange | 591-610 | 0.0081 | 0.0096 | 0.0079 | 0.0085 | 0.00 | 0.0% |
| Red | 610-760 | 0.0082 | 0.0098 | 0.0081 | 0.0065 | 0.00 | 0.0% |
| total | (400-700) | 33.46 | 33.39 | 33.26 | 33.19 | 10.16 | 100.0% |

TABLE 14

Photoactivatable fibers comprising nylon compounded with Eosin

| Fiber | Composition | Fluorescence Emission |
|---|---|---|
| 12 | Nylon with 0.5% Eosin + Lurol Oil Coating | Table 15 |
| 13 | Nylon with 0.5% Eosin + 1% Urea Peroxide Coating + Lurol Oil Coating | Table 16 |
| 14 | Nylon with 0.5% Eosin + Sodium Bicarbonate Coating + Lurol Oil Coating | Table 17 |
| 15 | Nylon with 0.5% Eosin + 10 g/L Eosin Y Coating + Lurol Oil Coating | Table 18 |

TABLE 15

Fiber 12 - Nylon + Eosin Inside, Lurol Oil Outside

| Fiber 12 - Nylon + Eosin Inside, Lurol Oil Outside | | mW/cm2 at 5 cm | | | | | | |
|---|---|---|---|---|---|---|---|---|
| | | 0 | 0.5 min | 1 min | 1.5 min | 2 min | 2.5 min | 3 min |
| Lamp | 400-518 | 8.45 | 9.13 | 10.34 | 11.38 | 12.24 | 13.06 | 13.83 |
| Fluoresc. | 519-760 | 7.55 | 6.46 | 5.97 | 5.54 | 5.23 | 4.91 | 4.64 |
| total | 400-760 | 15.99847 | 15.59112 | 16.31268 | 16.92697 | 17.46969 | 17.96796 | 18.46997 |
| % fluorescence | | 47.2% | 41.4% | 36.6% | 32.7% | 29.9% | 27.3% | 25.1% |
| purple | (400)-450 | 6.8019 | 6.9690 | 7.5393 | 7.9927 | 8.3430 | 8.6685 | 8.9554 |
| Blue | 450-500 | 1.6408 | 2.1589 | 2.7965 | 3.3803 | 3.8857 | 4.3748 | 4.8527 |
| Green | 500-570 | 2.0031 | 1.7498 | 1.6586 | 1.5746 | 1.5063 | 1.4374 | 1.3732 |
| Yellow | 570-591 | 2.2768 | 1.9007 | 1.7088 | 1.5559 | 1.4441 | 1.3456 | 1.2576 |
| Orange | 591-610 | 1.4927 | 1.2519 | 1.1345 | 1.0406 | 0.9709 | 0.9120 | 0.8536 |
| Red | 610-760 | 1.8387 | 1.6080 | 1.5182 | 1.4229 | 1.3568 | 1.2651 | 1.2106 |
| total | (400-700) | 16.05 | 15.64 | 16.36 | 16.97 | 17.51 | 18.00 | 18.50 |

| Fiber 12 - Nylon + Eosin Inside, Lurol Oil Outside | | mW/cm2 at 5 cm | | | | | |
|---|---|---|---|---|---|---|---|
| | | 3.5 min | 4 min | 4.5 min | 5 min | J/cm2 | |
| Lamp | 400-518 | 14.52 | 15.24 | 15.82 | 16.38 | 3.72 | 69.9% |
| Fluoresc. | 519-760 | 4.40 | 4.25 | 4.03 | 3.90 | 1.59 | 29.9% |
| total | 400-760 | 18.92674 | 19.48819 | 19.84828 | 20.28261 | 5.31 | 99.8% |
| % fluorescence | | 23.3% | 21.8% | 20.3% | 19.2% | 0.30 | 29.9% |
| purple | (400)-450 | 9.2182 | 9.4951 | 9.6972 | 9.8883 | 2.51 | 47.2% |
| Blue | 450-500 | 5.2897 | 5.7259 | 6.0989 | 6.4642 | 1.21 | 22.7% |
| Green | 500-570 | 1.3144 | 1.2775 | 1.2280 | 1.2009 | 0.45 | 8.5% |
| Yellow | 570-591 | 1.1845 | 1.1207 | 1.0606 | 1.0133 | 0.45 | 8.4% |
| Orange | 591-610 | 0.8080 | 0.7702 | 0.7336 | 0.7040 | 0.30 | 5.6% |
| Red | 610-760 | 1.1433 | 1.1291 | 1.0584 | 1.0397 | 0.41 | 7.6% |
| total | (400-700) | 18.96 | 19.52 | 19.88 | 20.31 | 5.32 | 100.0% |

TABLE 16

Fiber 13 - Nylon + Eosin Inside, UP + Lurol Oil Outside (25-30 minutes)

| Fiber 13 - Nylon + Eosin Inside, UP + Lurol Oil Outside (25-30 minutes) | | mW/cm2 at 5 cm | | | | | | |
|---|---|---|---|---|---|---|---|---|
| | | 0 | 0.5 min | 1 min | 1.5 min | 2 min | 2.5 min | 3 min |
| Lamp | 400-518 | 24.96 | 25.05 | 25.19 | 25.29 | 25.42 | 25.49 | 25.61 |
| Fluoresc. | 519-760 | 1.98 | 1.93 | 1.93 | 1.95 | 1.91 | 1.90 | 1.89 |
| total | 400-760 | 26.93968 | 26.98401 | 27.11688 | 27.24167 | 27.32461 | 27.38227 | 27.49843 |
| % fluorescence | | 7.4% | 7.2% | 7.1% | 7.2% | 7.0% | 6.9% | 6.9% |
| purple | (400)-450 | 13.4292 | 13.4647 | 13.5354 | 13.5872 | 13.6501 | 13.6725 | 13.7437 |
| Blue | 450-500 | 11.4229 | 11.4809 | 11.5418 | 11.5944 | 11.6551 | 11.7014 | 11.7509 |
| Green | 500-570 | 0.7422 | 0.7341 | 0.7330 | 0.7372 | 0.7289 | 0.7264 | 0.7299 |
| Yellow | 570-591 | 0.4073 | 0.3998 | 0.3982 | 0.3978 | 0.3923 | 0.3909 | 0.3853 |
| Orange | 591-610 | 0.3298 | 0.3235 | 0.3230 | 0.3212 | 0.3183 | 0.3170 | 0.3128 |
| Red | 610-760 | 0.6231 | 0.5954 | 0.5999 | 0.6183 | 0.5943 | 0.5883 | 0.5899 |
| total | (400-700) | 26.95 | 27.00 | 27.13 | 27.26 | 27.34 | 27.40 | 27.51 |

| Fiber 13 - Nylon + Eosin Inside, UP + Lurol Oil Outside (25-30 minutes) | | mW/cm2 at 5 cm | | | | | |
|---|---|---|---|---|---|---|---|
| | | 3.5 min | 4 min | 4.5 min | 5 min | J/cm2 | |
| Lamp | 400-518 | 25.68 | 25.78 | 25.90 | 25.99 | 7.63 | 93.0% |
| Fluoresc. | 519-760 | 1.84 | 1.88 | 1.86 | 1.84 | 0.57 | 7.0% |
| total | 400-760 | 27.52573 | 27.66029 | 27.7626 | 27.83434 | 8.20 | 99.9% |
| % fluorescence | | 6.7% | 6.8% | 6.7% | 6.6% | 0.07 | 7.0% |
| purple | (400)-450 | 13.7672 | 13.8125 | 13.8662 | 13.9151 | 4.10 | 49.9% |
| Blue | 450-500 | 11.8032 | 11.8555 | 11.9193 | 11.9667 | 3.50 | 42.7% |
| Green | 500-570 | 0.7229 | 0.7323 | 0.7294 | 0.7230 | 0.22 | 2.7% |
| Yellow | 570-591 | 0.3833 | 0.3793 | 0.3786 | 0.3737 | 0.12 | 1.4% |
| Orange | 591-610 | 0.3103 | 0.3079 | 0.3066 | 0.3036 | 0.10 | 1.2% |
| Red | 610-760 | 0.5528 | 0.5867 | 0.5762 | 0.5659 | 0.18 | 2.2% |
| total | (400-700) | 27.54 | 27.67 | 27.78 | 27.85 | 8.21 | 100.0% |

TABLE 17

Fiber 14 - Nylon + Eosin Inside, Bicarbonate + Lurol Oil Outside (25-30 minutes)

| Fiber 14 - Nylon + Eosin Inside, Bicarbonate + Lurol Oil Outside (25-30 minutes) | | mW/cm2 at 5 cm | | | | | | |
|---|---|---|---|---|---|---|---|---|
| | | 0 | 0.5 min | 1 min | 1.5 min | 2 min | 2.5 min | 3 min |
| Lamp | 400-518 | 27.04 | 27.10 | 27.20 | 27.13 | 27.12 | 27.21 | 27.30 |
| Fluoresc. | 519-760 | 1.72 | 1.70 | 1.69 | 1.65 | 1.61 | 1.59 | 1.59 |
| total | 400-760 | 28.7625 | 28.80483 | 28.88949 | 28.77401 | 28.72682 | 28.79745 | 28.89051 |
| % fluorescence | | 6.0% | 5.9% | 5.8% | 5.7% | 5.6% | 5.5% | 5.5% |
| purple | (400)-450 | 14.7774 | 14.7599 | 14.7845 | 14.7271 | 14.6997 | 14.7221 | 14.7524 |
| Blue | 450-500 | 12.1575 | 12.2336 | 12.3042 | 12.2857 | 12.3044 | 12.3716 | 12.4369 |
| Green | 500-570 | 0.7817 | 0.7752 | 0.7711 | 0.7525 | 0.7403 | 0.7425 | 0.7407 |
| Yellow | 570-591 | 0.3552 | 0.3522 | 0.3484 | 0.3332 | 0.3294 | 0.3225 | 0.3216 |
| Orange | 591-610 | 0.2653 | 0.2623 | 0.2593 | 0.2496 | 0.2476 | 0.2397 | 0.2398 |
| Red | 610-760 | 0.4370 | 0.4330 | 0.4333 | 0.4369 | 0.4162 | 0.4097 | 0.4097 |
| total | (400-700) | 28.77 | 28.82 | 28.90 | 28.78 | 28.74 | 28.81 | 28.90 |

TABLE 17-continued

Fiber 14 - Nylon + Eosin Inside, Bicarbonate + Lurol Oil Outside (25-30 minutes)

| Fiber 14 - Nylon + Eosin Inside, Bicarbonate + Lurol Oil Outside (25-30 minutes) | | mW/cm2 at 5 cm | | | | | |
|---|---|---|---|---|---|---|---|
| | | 3.5 min | 4 min | 4.5 min | 5 min | J/cm2 | |
| Lamp | 400-518 | 27.37 | 27.49 | 27.58 | 27.53 | 8.18 | 94.4% |
| Fluoresc. | 519-760 | 1.57 | 1.54 | 1.56 | 1.49 | 0.49 | 5.6% |
| total | 400-760 | 28.94176 | 29.02669 | 29.14196 | 29.0172 | 8.66 | 100.0% |
| % fluorescence | | 5.4% | 5.3% | 5.3% | 5.1% | 0.06 | 5.6% |
| purple | (400)-450 | 14.7707 | 14.8138 | 14.8509 | 14.7998 | 4.43 | 51.1% |
| Blue | 450-500 | 12.4876 | 12.5577 | 12.6191 | 12.6099 | 3.71 | 42.8% |
| Green | 500-570 | 0.7376 | 0.7291 | 0.7282 | 0.7190 | 0.22 | 2.6% |
| Yellow | 570-591 | 0.3195 | 0.3133 | 0.3150 | 0.3054 | 0.10 | 1.1% |
| Orange | 591-610 | 0.2385 | 0.2326 | 0.2365 | 0.2263 | 0.07 | 0.9% |
| Red | 610-760 | 0.3982 | 0.3904 | 0.4027 | 0.3666 | 0.13 | 1.4% |
| total | (400-700) | 28.95 | 29.04 | 29.15 | 29.03 | 8.67 | 100.0% |

TABLE 18

Fiber 15 - Nylon + Eosin Inside, Eosin + Lurol Oil Outside - Trial 2 (25-30 minutes)

| Fiber 15 - Nylon + Eosin Inside, Eosin + Lurol Oil Outside - Trial 2 (25-30 minutes) | | mW/cm2 at 5 cm | | | | | | |
|---|---|---|---|---|---|---|---|---|
| | | 0 | 0.5 min | 1 min | 1.5 min | 2 min | 2.5 min | 3 min |
| Lamp | 400-518 | 18.95 | 19.06 | 19.19 | 19.29 | 19.41 | 19.49 | 19.61 |
| Fluoresc. | 519-760 | 2.25 | 2.23 | 2.24 | 2.19 | 2.20 | 2.17 | 2.18 |
| total | 400-760 | 21.20136 | 21.28697 | 21.42811 | 21.48191 | 21.60579 | 21.66376 | 21.78431 |
| % fluorescence | | 10.6% | 10.5% | 10.4% | 10.2% | 10.2% | 10.0% | 10.0% |
| purple | (400)-450 | 10.4090 | 10.4463 | 10.5206 | 10.5657 | 10.6302 | 10.6576 | 10.7182 |
| Blue | 450-500 | 8.4999 | 8.5673 | 8.6248 | 8.6759 | 8.7348 | 8.7871 | 8.8430 |
| Green | 500-570 | 0.5179 | 0.5198 | 0.5227 | 0.5133 | 0.5139 | 0.5128 | 0.5124 |
| Yellow | 570-591 | 0.5174 | 0.5138 | 0.5096 | 0.5043 | 0.5029 | 0.4997 | 0.4990 |
| Orange | 591-610 | 0.4525 | 0.4474 | 0.4439 | 0.4396 | 0.4384 | 0.4349 | 0.4342 |
| Red | 610-760 | 0.8250 | 0.8123 | 0.8263 | 0.8028 | 0.8053 | 0.7911 | 0.7970 |
| total | (400-700) | 21.22 | 21.31 | 21.45 | 21.50 | 21.63 | 21.68 | 21.80 |

| Fiber 15 - Nylon + Eosin Inside, Eosin + Lurol Oil Outside - Trial 2 (25-30 minutes) | | mW/cm2 at 5 cm | | | | | |
|---|---|---|---|---|---|---|---|
| | | 3.5 min | 4 min | 4.5 min | 5 min | J/cm2 | |
| Lamp | 400-518 | 19.74 | 19.83 | 19.94 | 20.05 | 5.84 | 89.8% |
| Fluoresc. | 519-760 | 2.19 | 2.15 | 2.15 | 2.13 | 0.66 | 10.1% |
| total | 400-760 | 21.92765 | 21.98483 | 22.08331 | 22.17704 | 6.49 | 99.9% |
| % fluorescence | | 10.0% | 9.8% | 9.7% | 9.6% | 0.10 | 10.1% |
| purple | (400)-450 | 10.7853 | 10.8302 | 10.8776 | 10.9295 | 3.19 | 49.1% |
| Blue | 450-500 | 8.9077 | 8.9536 | 9.0093 | 9.0661 | 2.63 | 40.4% |
| Green | 500-570 | 0.5241 | 0.5177 | 0.5155 | 0.5159 | 0.16 | 2.4% |
| Yellow | 570-591 | 0.4989 | 0.4941 | 0.4892 | 0.4894 | 0.15 | 2.3% |
| Orange | 591-610 | 0.4322 | 0.4282 | 0.4264 | 0.4245 | 0.13 | 2.0% |
| Red | 610-760 | 0.7988 | 0.7803 | 0.7846 | 0.7707 | 0.24 | 3.7% |
| total | (400-700) | 21.95 | 22.00 | 22.10 | 22.20 | 6.50 | 100.0% |

TABLE 19

Photoactivatable fibers comprising polybutylene terephthalate (PBT) compounded with Eosin

| Fiber | Composition | Fluorescence Emission |
|---|---|---|
| 16 | Virgin PBT + Lurol Oil Coating | Table 20 |
| 17 | PBT with 1% Eosin + Lurol Oil Coating | Table 21 |
| 18 | PBT with 1% Eosin + 1% Urea Peroxide Coating + Lurol Oil Coating | Table 22 |
| 19 | PBT with 1% Eosin + Sodium Bicarbonate Coating + Lurol Oil Coating | Table 23 |
| 20 | PBT with 1% Eosin + 10 g/L Eosin Y Coating + Lurol Oil Coating | Table 24 |

TABLE 20

Fiber 16 - PBT Blank

| Fiber 16 - PBT Blank | | mW/cm2 at 5 cm | | | | | | |
|---|---|---|---|---|---|---|---|---|
| | | 0 | 0.5 min | 1 min | 1.5 min | 2 min | 2.5 min | 3 min |
| Lamp | 400-518 | 69.78 | 69.35 | 69.24 | 68.90 | 68.53 | 68.16 | 68.04 |
| Fluoresc. | 519-760 | 0.05 | 0.07 | 0.06 | 0.05 | 0.05 | 0.06 | 0.05 |
| total | 400-760 | 69.82895 | 69.4195 | 69.30044 | 68.95217 | 68.5783 | 68.21259 | 68.09006 |
| % fluorescence | | 0.1% | 0.1% | 0.1% | 0.1% | 0.1% | 0.1% | 0.1% |
| purple | (400)-450 | 42.9096 | 42.0190 | 41.5394 | 40.9650 | 40.4537 | 39.9428 | 39.6390 |
| Blue | 450-500 | 26.7852 | 27.2232 | 27.5890 | 27.8149 | 27.9591 | 28.0905 | 28.2822 |
| Green | 500-570 | 0.1043 | 0.1571 | 0.1564 | 0.1587 | 0.1566 | 0.1574 | 0.1648 |
| Yellow | 570-591 | 0.0000 | 0.0052 | 0.0084 | 0.0098 | 0.0050 | 0.0067 | 0.0040 |
| Orange | 591-610 | 0.0000 | 0.0088 | 0.0059 | 0.0033 | 0.0035 | 0.0087 | 0.0001 |
| Red | 610-760 | 0.0299 | 0.0066 | 0.0016 | 0.0006 | 0.0006 | 0.0071 | 0.0000 |
| total | (400-700) | 69.83 | 69.42 | 69.30 | 68.95 | 68.58 | 68.21 | 68.09 |

| Fiber 16 - PBT Blank | | mW/cm2 at 5 cm | | | | | |
|---|---|---|---|---|---|---|---|
| | | 3.5 min | 4 min | 4.5 min | 5 min | J/cm2 | |
| Lamp | 400-518 | 67.72 | 67.51 | 67.29 | 67.15 | 20.54 | 99.9% |
| Fluoresc. | 519-760 | 0.07 | 0.06 | 0.05 | 0.04 | 0.02 | 0.1% |
| total | 400-760 | 67.79068 | 67.56456 | 67.3467 | 67.19618 | 20.55 | 100.0% |
| % fluorescence | | 0.1% | 0.1% | 0.1% | 0.1% | 0.00 | 0.1% |
| purple | (400)-450 | 39.2507 | 38.9616 | 38.6804 | 38.4675 | 12.13 | 59.0% |
| Blue | 450-500 | 28.3575 | 28.4216 | 28.4878 | 28.5608 | 8.37 | 40.7% |
| Green | 500-570 | 0.1639 | 0.1680 | 0.1621 | 0.1529 | 0.05 | 0.2% |
| Yellow | 570-591 | 0.0110 | 0.0079 | 0.0106 | 0.0061 | 0.00 | 0.0% |
| Orange | 591-610 | 0.0069 | 0.0049 | 0.0058 | 0.0060 | 0.00 | 0.0% |
| Red | 610-760 | 0.0010 | 0.0006 | 0.0001 | 0.0032 | 0.00 | 0.0% |
| total | (400-700) | 67.79 | 67.56 | 67.35 | 67.20 | 20.55 | 100.0% |

TABLE 21

Fiber 17 - PBT + Eosin Inside, Lurol Oil Outside

| Fiber 17 - PBT + Eosin Inside, Lurol Oil Outside | | UZ,13/49 mW/cm2 at 5 cm | | | | | | |
|---|---|---|---|---|---|---|---|---|
| | | 0 | 0.5 min | 1 min | 1.5 min | 2 min | 2.5 min | 3 min |
| Lamp | 400-518 | 2.63 | 2.57 | 2.41 | 2.18 | 2.06 | 1.99 | 2.26 |
| Fluoresc. | 519-760 | 2.83 | 2.73 | 2.71 | 2.64 | 2.58 | 2.51 | 2.45 |
| total | 400-760 | 5.463108 | 5.298557 | 5.120492 | 4.828287 | 4.644863 | 4.504063 | 4.707606 |
| % fluorescence | | 51.8% | 51.5% | 53.0% | 54.8% | 55.6% | 55.8% | 52.1% |
| purple | (400)-450 | 1.8166 | 1.7553 | 1.6450 | 1.5014 | 1.4223 | 1.3755 | 1.5282 |
| Blue | 450-500 | 0.8139 | 0.8126 | 0.7602 | 0.6817 | 0.6405 | 0.6139 | 0.7270 |
| Green | 500-570 | 0.0536 | 0.0543 | 0.0575 | 0.0548 | 0.0545 | 0.0552 | 0.0543 |
| Yellow | 570-591 | 0.5284 | 0.4851 | 0.4763 | 0.4619 | 0.4510 | 0.4395 | 0.4304 |

TABLE 21-continued

Fiber 17 - PBT + Eosin Inside, Lurol Oil Outside

| | | | | | | | | |
|---|---|---|---|---|---|---|---|---|
| Orange | 591-610 | 0.7208 | 0.6774 | 0.6674 | 0.6502 | 0.6344 | 0.6149 | 0.5997 |
| Red | 610-760 | 1.5646 | 1.5467 | 1.5464 | 1.5100 | 1.4731 | 1.4350 | 1.3972 |
| total | (400-700) | 5.50 | 5.33 | 5.15 | 4.86 | 4.68 | 4.53 | 4.74 |

| Fiber 17 - PBT + Eosin Inside, Lurol Oil Outside | | mW/cm2 at 5 cm | | | | | |
|---|---|---|---|---|---|---|---|
| | | 3.5 min | 4 min | 4.5 min | 5 min | J/cm2 | |
| Lamp | 400-518 | 2.34 | 2.30 | 2.28 | 2.24 | 0.69 | 47.1% |
| Fluoresc. | 519-760 | 2.40 | 2.36 | 2.34 | 2.33 | 0.77 | 52.3% |
| total | 400-760 | 4.736382 | 4.659129 | 4.616988 | 4.571799 | 1.46 | 99.4% |
| % fluorescence | | 50.6% | 50.7% | 50.7% | 50.9% | 0.53 | 52.6% |
| purple | (400)-450 | 1.5655 | 1.5335 | 1.5147 | 1.4931 | 0.47 | 32.0% |
| Blue | 450-500 | 0.7718 | 0.7606 | 0.7591 | 0.7499 | 0.22 | 15.0% |
| Green | 500-570 | 0.0554 | 0.0537 | 0.0556 | 0.0561 | 0.02 | 1.1% |
| Yellow | 570-591 | 0.4193 | 0.4146 | 0.4093 | 0.4090 | 0.14 | 9.2% |
| Orange | 591-610 | 0.5842 | 0.5764 | 0.5684 | 0.5648 | 0.19 | 12.9% |
| Red | 610-760 | 1.3685 | 1.3481 | 1.3375 | 1.3262 | 0.44 | 29.7% |
| total | (400-700) | 4.76 | 4.69 | 4.64 | 4.60 | 1.47 | 100.0% |

TABLE 22

Fiber 18 - PBT + Eosin Inside, UP + Lurol Oil Outside

| Fiber 18 - PBT + Eosin Inside, UP + Lurol Oil Outside | | mW/cm2 at 5 cm | | | | | |
|---|---|---|---|---|---|---|---|
| | | 0 | 0.5 min | 1 min | 1.5 min | 2 min | 2.5 min |
| Lamp | 400-518 | 0.42 | 0.46 | 1.12 | 0.91 | 0.91 | 0.96 |
| Fluoresc. | 519-760 | 2.32 | 2.04 | 1.90 | 1.84 | 1.81 | 1.78 |
| total | 400-760 | 2.740057 | 2.495696 | 3.021197 | 2.744473 | 2.727173 | 2.740978 |
| % fluorescence | | 84.6% | 81.8% | 63.0% | 66.9% | 66.5% | 65.1% |
| purple | (400)-450 | 0.3091 | 0.3171 | 0.7094 | 0.5882 | 0.5908 | 0.6157 |
| Blue | 450-500 | 0.1126 | 0.1379 | 0.4059 | 0.3184 | 0.3210 | 0.3396 |
| Green | 500-570 | 0.0497 | 0.0412 | 0.0447 | 0.0430 | 0.0441 | 0.0444 |
| Yellow | 570-591 | 0.4315 | 0.3609 | 0.3414 | 0.3298 | 0.3247 | 0.3202 |
| Orange | 591-610 | 0.5479 | 0.4794 | 0.4456 | 0.4291 | 0.4212 | 0.4130 |
| Red | 610-760 | 1.3154 | 1.1822 | 1.0955 | 1.0564 | 1.0456 | 1.0277 |
| total | (400-700) | 2.77 | 2.52 | 3.04 | 2.76 | 2.75 | 2.76 |

| Fiber 18 - PBT + Eosin Inside, UP + Lurol Oil Outside | | mW/cm2 at 5 cm | | | | | |
|---|---|---|---|---|---|---|---|
| | | 3 min | 3.5 min | 4 min | 4.5 min | 5 min | J/cm2 | |
| Lamp | 400-518 | 0.99 | 0.99 | 0.99 | 1.08 | 1.07 | 0.26 | 32.0% |
| Fluoresc. | 519-760 | 1.76 | 1.72 | 1.69 | 1.66 | 1.63 | 0.56 | 67.2% |
| total | 400-760 | 2.744468 | 2.71341 | 2.678671 | 2.743669 | 2.696495 | 0.82 | 99.3% |
| % fluorescence | | 64.0% | 63.4% | 63.1% | 60.6% | 60.3% | 0.68 | 67.7% |
| purple | (400)-450 | 0.6325 | 0.6333 | 0.6306 | 0.6807 | 0.6734 | 0.17 | 20.7% |
| Blue | 450-500 | 0.3549 | 0.3580 | 0.3572 | 0.3990 | 0.3955 | 0.09 | 11.3% |
| Green | 500-570 | 0.0452 | 0.0456 | 0.0463 | 0.0471 | 0.0470 | 0.01 | 1.6% |
| Yellow | 570-591 | 0.3163 | 0.3103 | 0.3053 | 0.3009 | 0.2959 | 0.10 | 12.1% |
| Orange | 591-610 | 0.4054 | 0.3958 | 0.3873 | 0.3800 | 0.3715 | 0.13 | 15.6% |
| Red | 610-760 | 1.0096 | 0.9893 | 0.9704 | 0.9539 | 0.9309 | 0.32 | 38.6% |
| total | (400-700) | 2.76 | 2.73 | 2.70 | 2.76 | 2.71 | 0.83 | 100.0% |

TABLE 23

Fiber 19 - PBT + Eosin Inside, Bicarb + Lurol Oil Outside

| Fiber 19 - PBT + Eosin Inside, Bicarb + Lurol Oil Outside | | mW/cm2 at 5 cm | | | | | |
|---|---|---|---|---|---|---|---|
| | | 0 | 0.5 min | 1 min | 1.5 min | 2 min | 2.5 min |
| Lamp | 400-518 | 0.55 | 0.56 | 1.00 | 1.17 | 1.25 | 1.08 |
| Fluoresc. | 519-760 | 2.40 | 2.11 | 1.94 | 1.86 | 1.78 | 1.76 |
| total | 400-760 | 2.954142 | 2.667009 | 2.942724 | 3.028633 | 3.035268 | 2.841185 |
| % fluorescence | | 81.4% | 79.1% | 65.9% | 61.5% | 58.7% | 62.1% |
| purple | (400)-450 | 0.3923 | 0.3886 | 0.6557 | 0.7512 | 0.7970 | 0.6904 |
| Blue | 450-500 | 0.1566 | 0.1676 | 0.3467 | 0.4136 | 0.4562 | 0.3852 |
| Green | 500-570 | 0.0504 | 0.0408 | 0.0409 | 0.0416 | 0.0404 | 0.0425 |
| Yellow | 570-591 | 0.4400 | 0.3607 | 0.3312 | 0.3199 | 0.3066 | 0.3023 |
| Orange | 591-610 | 0.5668 | 0.4937 | 0.4519 | 0.4318 | 0.4119 | 0.4049 |
| Red | 610-760 | 1.3750 | 1.2394 | 1.1382 | 1.0913 | 1.0431 | 1.0353 |
| total | (400-700) | 2.98 | 2.69 | 2.96 | 3.05 | 3.06 | 2.86 |

| Fiber 19 - PBT + Eosin Inside, Bicarb + Lurol Oil Outside | | mW/cm2 at 5 cm | | | | | |
|---|---|---|---|---|---|---|---|
| | | 3 min | 3.5 min | 4 min | 4.5 min | 5 min | J/cm2 | |
| Lamp | 400-518 | 1.05 | 1.05 | 1.09 | 1.11 | 1.13 | 0.30 | 34.4% |
| Fluoresc. | 519-760 | 1.74 | 1.71 | 1.69 | 1.66 | 1.64 | 0.56 | 64.9% |
| total | 400-760 | 2.787107 | 2.766328 | 2.777914 | 2.770098 | 2.774827 | 0.86 | 99.3% |
| % fluorescence | | 62.4% | 61.9% | 60.9% | 60.1% | 59.2% | 0.65 | 65.3% |
| purple | (400)-450 | 0.6687 | 0.6707 | 0.6870 | 0.6962 | 0.7091 | 0.19 | 22.2% |
| Blue | 450-500 | 0.3775 | 0.3828 | 0.3989 | 0.4086 | 0.4225 | 0.10 | 12.1% |
| Green | 500-570 | 0.0432 | 0.0441 | 0.0449 | 0.0453 | 0.0460 | 0.01 | 1.5% |
| Yellow | 570-591 | 0.2983 | 0.2935 | 0.2904 | 0.2869 | 0.2834 | 0.10 | 11.2% |
| Orange | 591-610 | 0.3978 | 0.3895 | 0.3835 | 0.3768 | 0.3705 | 0.13 | 15.0% |
| Red | 610-760 | 1.0207 | 1.0044 | 0.9917 | 0.9744 | 0.9612 | 0.33 | 37.9% |
| total | (400-700) | 2.81 | 2.79 | 2.80 | 2.79 | 2.79 | 0.86 | 100.0% |

TABLE 24

Fiber 20 - PBT + Eosin Inside, Eosin + Lurol Oil Outside

| Fiber 20 - PBT + Eosin Inside, Eosin + Lurol Oil Outside | | mW/cm2 at 5 cm | | | | | |
|---|---|---|---|---|---|---|---|
| | | 0 | 0.5 min | 1 min | 1.5 min | 2 min | 2.5 min |
| Lamp | 400-518 | 3.25 | 3.82 | 3.91 | 4.14 | 4.19 | 4.39 |
| Fluoresc. | 519-760 | 2.72 | 2.62 | 2.54 | 2.42 | 2.36 | 2.30 |
| total | 400-760 | 5.966188 | 6.441835 | 6.450766 | 6.557832 | 6.549098 | 6.694657 |
| % fluorescence | | 45.6% | 40.7% | 39.4% | 36.9% | 36.0% | 34.4% |
| purple | (400)-450 | 2.1823 | 2.5014 | 2.5369 | 2.6563 | 2.6642 | 2.7716 |
| Blue | 450-500 | 1.0644 | 1.3131 | 1.3703 | 1.4781 | 1.5245 | 1.6190 |
| Green | 500-570 | 0.0508 | 0.0554 | 0.0585 | 0.0551 | 0.0556 | 0.0568 |
| Yellow | 570-591 | 0.4800 | 0.4340 | 0.4202 | 0.4071 | 0.3951 | 0.3860 |
| Orange | 591-610 | 0.6916 | 0.6422 | 0.6186 | 0.5936 | 0.5743 | 0.5586 |
| Red | 610-760 | 1.5314 | 1.5275 | 1.4769 | 1.3971 | 1.3637 | 1.3304 |
| total | (400-700) | 6.00 | 6.47 | 6.48 | 6.59 | 6.58 | 6.72 |

| Fiber 20 - PBT + Eosin Inside, Eosin + Lurol Oil Outside | | mW/cm2 at 5 cm | | | | | |
|---|---|---|---|---|---|---|---|
| | | 3 min | 3.5 min | 4 min | 4.5 min | 5 min | J/cm2 | |
| Lamp | 400-518 | 4.35 | 4.30 | 4.27 | 4.27 | 4.24 | 1.23 | 62.9% |
| Fluoresc. | 519-760 | 2.27 | 2.23 | 2.20 | 2.17 | 2.16 | 0.72 | 36.7% |
| total | 400-760 | 6.622601 | 6.520864 | 6.46933 | 6.436219 | 6.394325 | 1.94 | 99.6% |
| % fluorescence | | 34.3% | 34.1% | 34.1% | 33.7% | 33.8% | 0.37 | 36.8% |
| purple | (400)-450 | 2.7308 | 2.6852 | 2.6568 | 2.6469 | 2.6211 | 0.78 | 40.1% |

TABLE 24-continued

Fiber 20 - PBT + Eosin Inside, Eosin + Lurol Oil Outside

| | | | | | | | | |
|---|---|---|---|---|---|---|---|---|
| Blue | 450-500 | 1.6181 | 1.6076 | 1.6056 | 1.6155 | 1.6114 | 0.44 | 22.8% |
| Green | 500-570 | 0.0560 | 0.0546 | 0.0576 | 0.0569 | 0.0567 | 0.02 | 0.9% |
| Yellow | 570-591 | 0.3797 | 0.3738 | 0.3682 | 0.3644 | 0.3631 | 0.12 | 6.2% |
| Orange | 591-610 | 0.5488 | 0.5387 | 0.5300 | 0.5229 | 0.5176 | 0.17 | 9.0% |
| Red | 610-760 | 1.3163 | 1.2875 | 1.2773 | 1.2554 | 1.2499 | 0.41 | 21.2% |
| total | (400-700) | 6.65 | 6.55 | 6.50 | 6.46 | 6.42 | 1.95 | 100.0% |

TABLE 25

Photoactivatable fibers comprising poly(methyl methacrylate) (PMMA) compounded with Eosin

| Fiber | Composition | Fluorescence Emission |
|---|---|---|
| 21 | PMMA with 1% Eosin + Lurol Oil Coating | Table 26 |
| 22 | PMMA with 1% Eosin + 1% Urea Peroxide Coating + Lurol Oil Coating | Table 27 |
| 23 | PrMMA with 1% Eosin + Sodium Bicarbonate Coating + Lurol Oil Coating | Table 28 |
| 24 | PMMA with 1% Eosin + 10 g/L Eosin Y Coating + Lurol Oil Coating | Table 29 |

TABLE 26

Fiber 21 - PMMA + Eosin Inside, Lurol Oil Outside

| Fiber 21 - PMMA + Eosin | | mW/cm2 at 5 cm | | | | | |
|---|---|---|---|---|---|---|---|
| Inside, Lurol Oil Outside | | 0 | 0.5 min | 1 min | 1.5 min | 2 min | 2.5 min |
| Lamp | 400-518 | 10.26 | 10.12 | 10.08 | 10.02 | 9.98 | 9.96 |
| Fluoresc. | 519-760 | 0.73 | 0.67 | 0.65 | 0.64 | 0.63 | 0.63 |
| total | 400-760 | 10.99377 | 10.79335 | 10.72893 | 10.65819 | 10.61231 | 10.58607 |
| % fluorescence | | 6.7% | 6.2% | 6.0% | 6.0% | 5.9% | 5.9% |
| purple | (400)-450 | 7.8615 | 7.6370 | 7.5561 | 7.4510 | 7.3697 | 7.3017 |
| Blue | 450-500 | 2.3995 | 2.4856 | 2.5276 | 2.5694 | 2.6118 | 2.6571 |
| Green | 500-570 | 0.0096 | 0.0069 | 0.0050 | 0.0043 | 0.0038 | 0.0033 |
| Yellow | 570-591 | 0.1304 | 0.1195 | 0.1128 | 0.1092 | 0.1063 | 0.1037 |
| Orange | 591-610 | 0.2326 | 0.2175 | 0.2105 | 0.2074 | 0.2043 | 0.2022 |
| Red | 610-760 | 0.3732 | 0.3388 | 0.3284 | 0.3283 | 0.3277 | 0.3293 |
| total | (400-700) | 11.01 | 10.81 | 10.74 | 10.67 | 10.62 | 10.60 |

| Fiber 21 - PMMA + Eosin | | mW/cm2 at 5 cm | | | | | |
|---|---|---|---|---|---|---|---|
| Inside, Lurol Oil Outside | | 3 min | 3.5 min | 4 min | 4.5 min | 5 min | J/cm2 |
| Lamp | 400-518 | 9.88 | 9.90 | 9.83 | 9.79 | 9.82 | 2.99 | 93.9% |
| Fluoresc. | 519-760 | 0.61 | 0.60 | 0.60 | 0.60 | 0.59 | 0.19 | 6.0% |
| total | 400-760 | 10.49542 | 10.50296 | 10.43348 | 10.39166 | 10.41602 | 3.19 | 99.9% |
| % fluorescence | | 5.9% | 5.7% | 5.8% | 5.8% | 5.7% | 0.06 | 6.0% |
| purple | (400)-450 | 7.2094 | 7.1832 | 7.1110 | 7.0489 | 7.0420 | 2.21 | 69.4% |
| Blue | 450-500 | 2.6720 | 2.7161 | 2.7200 | 2.7422 | 2.7821 | 0.78 | 24.6% |
| Green | 500-570 | 0.0028 | 0.0026 | 0.0025 | 0.0023 | 0.0020 | 0.00 | 0.0% |
| Yellow | 570-591 | 0.1003 | 0.0978 | 0.0963 | 0.0953 | 0.0928 | 0.03 | 1.0% |
| Orange | 591-610 | 0.1977 | 0.1949 | 0.1934 | 0.1922 | 0.1889 | 0.06 | 1.9% |
| Red | 610-760 | 0.3241 | 0.3193 | 0.3211 | 0.3215 | 0.3190 | 0.10 | 3.1% |
| total | (400-700) | 10.51 | 10.51 | 10.44 | 10.40 | 10.43 | 3.19 | 100.0% |

TABLE 27

Fiber 22 - PMMA + Eosin Inside, UP + Lurol Oil Outside

| Fiber 22 - PMMA + Eosin Inside, UP + Lurol Oil Outside | | mW/cm2 at 5 cm | | | | | |
|---|---|---|---|---|---|---|---|
| | | 0 | 0.5 min | 1 min | 1.5 min | 2 min | 2.5 min |
| Lamp | 400-518 | 15.69 | 14.95 | 14.74 | 14.59 | 14.47 | 14.42 |
| Fluoresc. | 519-760 | 0.75 | 0.67 | 0.66 | 0.64 | 0.64 | 0.63 |
| total | 400-760 | 16.4387 | 15.62283 | 15.39582 | 15.23084 | 15.11069 | 15.05078 |
| % fluorescence | | 4.6% | 4.3% | 4.3% | 4.2% | 4.3% | 4.2% |
| purple | (400)-450 | 11.0082 | 10.3866 | 10.1416 | 9.9691 | 9.8076 | 9.7133 |
| Blue | 450-500 | 4.6795 | 4.5640 | 4.5964 | 4.6207 | 4.6597 | 4.7054 |
| Green | 500-570 | 0.0004 | 0.0004 | 0.0002 | 0.0000 | 0.0000 | 0.0000 |
| Yellow | 570-591 | 0.0950 | 0.0842 | 0.0818 | 0.0763 | 0.0759 | 0.0727 |
| Orange | 591-610 | 0.2189 | 0.2031 | 0.1987 | 0.1947 | 0.1933 | 0.1901 |
| Red | 610-760 | 0.4494 | 0.3965 | 0.3888 | 0.3815 | 0.3856 | 0.3805 |
| total | (400-700) | 16.45 | 15.63 | 15.41 | 15.24 | 15.12 | 15.06 |

| Fiber 22 - PMMA + Eosin Inside, UP + Lurol Oil Outside | | mW/cm2 at 5 cm | | | | | |
|---|---|---|---|---|---|---|---|
| | | 3 min | 3.5 min | 4 min | 4.5 min | 5 min | J/cm2 | |
| Lamp | 400-518 | 14.39 | 14.36 | 14.33 | 14.28 | 14.27 | 4.39 | 95.7% |
| Fluoresc. | 519-760 | 0.63 | 0.63 | 0.62 | 0.61 | 0.60 | 0.19 | 4.2% |
| total | 400-760 | 15.01809 | 14.9848 | 14.95077 | 14.89236 | 14.87711 | 4.58 | 99.9% |
| % fluorescence | | 4.2% | 4.2% | 4.1% | 4.1% | 4.1% | 0.04 | 4.2% |
| purple | (400)-450 | 9.6369 | 9.5602 | 9.5019 | 9.4261 | 9.3807 | 2.97 | 64.9% |
| Blue | 450-500 | 4.7496 | 4.7990 | 4.8327 | 4.8559 | 4.8920 | 1.41 | 30.8% |
| Green | 500-570 | 0.0000 | 0.0000 | 0.0000 | 0.0000 | 0.0000 | 0.00 | 0.0% |
| Yellow | 570-591 | 0.0720 | 0.0703 | 0.0683 | 0.0664 | 0.0642 | 0.02 | 0.5% |
| Orange | 591-610 | 0.1884 | 0.1865 | 0.1828 | 0.1805 | 0.1789 | 0.06 | 1.3% |
| Red | 610-760 | 0.3825 | 0.3799 | 0.3760 | 0.3743 | 0.3721 | 0.12 | 2.5% |
| total | (400-700) | 15.03 | 15.00 | 14.96 | 14.90 | 14.89 | 4.58 | 100.0% |

TABLE 28

Fiber 23 - PMMA + Eosin Inside, Bicarbonate + Lurol Oil Outside

| Fiber 23 - PMMA + Eosin Inside, Bicarbonate + Lurol Oil Outside | | mW/cm2 at 5 cm | | | | | |
|---|---|---|---|---|---|---|---|
| | | 0 | 0.5 min | 1 min | 1.5 min | 2 min | 2.5 min |
| Lamp | 400-518 | 13.15 | 13.50 | 13.34 | 13.26 | 13.22 | 13.13 |
| Fluoresc. | 519-760 | 0.68 | 0.64 | 0.63 | 0.62 | 0.61 | 0.61 |
| total | 400-760 | 13.83246 | 14.1425 | 13.97107 | 13.88749 | 13.82635 | 13.73764 |
| % fluorescence | | 4.9% | 4.5% | 4.5% | 4.5% | 4.4% | 4.4% |
| purple | (400)-450 | 9.3441 | 9.4130 | 9.2256 | 9.1099 | 9.0173 | 8.9034 |
| Blue | 450-500 | 3.8100 | 4.0877 | 4.1181 | 4.1541 | 4.1999 | 4.2260 |
| Green | 500-570 | 0.0000 | 0.0000 | 0.0000 | 0.0000 | 0.0000 | 0.0000 |
| Yellow | 570-591 | 0.0804 | 0.0695 | 0.0664 | 0.0646 | 0.0623 | 0.0606 |
| Orange | 591-610 | 0.2044 | 0.1888 | 0.1839 | 0.1819 | 0.1782 | 0.1759 |
| Red | 610-760 | 0.4057 | 0.3948 | 0.3881 | 0.3880 | 0.3795 | 0.3824 |
| total | (400-700) | 13.84 | 14.15 | 13.98 | 13.90 | 13.84 | 13.75 |

| Fiber 23 - PMMA + Eosin Inside, Bicarbonate + Lurol Oil Outside | | mW/cm2 at 5 cm | | | | | |
|---|---|---|---|---|---|---|---|
| | | 3 min | 3.5 min | 4 min | 4.5 min | 5 min | J/cm2 | |
| Lamp | 400-518 | 12.89 | 12.80 | 12.69 | 12.59 | 12.51 | 3.92 | 95.4% |
| Fluoresc. | 519-760 | 0.61 | 0.60 | 0.60 | 0.59 | 0.59 | 0.19 | 4.5% |
| total | 400-760 | 13.49795 | 13.40275 | 13.28483 | 13.18373 | 13.09997 | 4.10 | 99.9% |
| % fluorescence | | 4.5% | 4.5% | 4.5% | 4.5% | 4.5% | 0.05 | 4.5% |
| purple | (400)-450 | 8.7126 | 8.6168 | 8.5063 | 8.4182 | 8.3422 | 2.68 | 65.2% |
| Blue | 450-500 | 4.1747 | 4.1828 | 4.1792 | 4.1748 | 4.1704 | 1.24 | 30.2% |
| Green | 500-570 | 0.0000 | 0.0000 | 0.0000 | 0.0000 | 0.0000 | 0.00 | 0.0% |

TABLE 28-continued

Fiber 23 - PMMA + Eosin Inside, Bicarbonate + Lurol Oil Outside

| | | | | | | | | |
|---|---|---|---|---|---|---|---|---|
| Yellow | 570-591 | 0.0604 | 0.0597 | 0.0591 | 0.0576 | 0.0565 | 0.02 | 0.5% |
| Orange | 591-610 | 0.1761 | 0.1742 | 0.1728 | 0.1704 | 0.1683 | 0.05 | 1.3% |
| Red | 610-760 | 0.3847 | 0.3798 | 0.3780 | 0.3732 | 0.3729 | 0.12 | 2.8% |
| total | (400-700) | 13.51 | 13.41 | 13.30 | 13.19 | 13.11 | 4.11 | 100.0% |

TABLE 29

Fiber 24 - PMMA + Eosin Inside, Eosin + Lurol Oil Outside

| Fiber 24 - PMMA + Eosin Inside, Eosin + Lurol Oil Outside | | mW/cm2 at 5 cm | | | | | |
|---|---|---|---|---|---|---|---|
| | | 0 | 0.5 min | 1 min | 1.5 min | 2 min | 2.5 min |
| Lamp | 400-518 | 13.69 | 13.11 | 13.01 | 12.84 | 12.64 | 12.72 |
| Fluoresc. | 519-760 | 0.49 | 0.47 | 0.46 | 0.45 | 0.44 | 0.44 |
| total | 400-760 | 14.1806 | 13.57408 | 13.46488 | 13.29157 | 13.08745 | 13.16511 |
| % fluorescence | | 3.5% | 3.4% | 3.4% | 3.4% | 3.4% | 3.4% |
| purple | (400)-450 | 9.6291 | 9.0682 | 8.9211 | 8.7398 | 8.5535 | 8.5459 |
| Blue | 450-500 | 4.0575 | 4.0408 | 4.0850 | 4.1040 | 4.0914 | 4.1746 |
| Green | 500-570 | 0.0000 | 0.0000 | 0.0000 | 0.0000 | 0.0000 | 0.0000 |
| Yellow | 570-591 | 0.0456 | 0.0374 | 0.0362 | 0.0350 | 0.0332 | 0.0325 |
| Orange | 591-610 | 0.1404 | 0.1264 | 0.1243 | 0.1215 | 0.1201 | 0.1197 |
| Red | 610-760 | 0.3167 | 0.3091 | 0.3061 | 0.2989 | 0.2969 | 0.3000 |
| total | (400-700) | 14.19 | 13.58 | 13.47 | 13.30 | 13.10 | 13.17 |

| Fiber 24 - PMMA + Eosin Inside, Eosin + Lurol Oil Outside | | mW/cm2 at 5 cm | | | | | |
|---|---|---|---|---|---|---|---|
| | | 3 min | 3.5 min | 4 min | 4.5 min | 5 min | J/cm2 |
| Lamp | 400-518 | 12.91 | 12.48 | 12.70 | 12.93 | 13.08 | 3.87 | 96.6% |
| Fluoresc. | 519-760 | 0.44 | 0.43 | 0.43 | 0.43 | 0.43 | 0.13 | 3.4% |
| total | 400-760 | 13.35073 | 12.91267 | 13.13371 | 13.35688 | 13.50934 | 4.01 | 99.9% |
| % fluorescence | | 3.3% | 3.4% | 3.3% | 3.2% | 3.2% | 0.03 | 3.4% |
| purple | (400)-450 | 8.6049 | 8.2940 | 8.3781 | 8.4711 | 8.5391 | 2.62 | 65.3% |
| Blue | 450-500 | 4.3091 | 4.1839 | 4.3231 | 4.4581 | 4.5427 | 1.25 | 31.3% |
| Green | 500-570 | 0.0000 | 0.0000 | 0.0000 | 0.0000 | 0.0000 | 0.00 | 0.0% |
| Yellow | 570-591 | 0.0312 | 0.0309 | 0.0308 | 0.0294 | 0.0296 | 0.01 | 0.3% |
| Orange | 591-610 | 0.1158 | 0.1154 | 0.1157 | 0.1133 | 0.1139 | 0.04 | 0.9% |
| Red | 610-760 | 0.2972 | 0.2959 | 0.2933 | 0.2922 | 0.2913 | 0.09 | 2.3% |
| total | (400-700) | 13.36 | 12.92 | 13.14 | 13.36 | 13.52 | 4.01 | 100.0% |

TABLE 30

Color Breakdown for fluorescence emission of nylon fibers

| Color | Fiber 12 | Fiber 13 | Fiber 14 | Fiber 15 |
|---|---|---|---|---|
| Purple | 2.51 | 2.25 | 2.47 | 2.44 |
| Blue | 1.21 | 1.05 | 1.07 | 1.07 |
| Green | 0.45 | 0.46 | 0.41 | 0.27 |
| Yellow | 0.45 | 0.45 | 0.38 | 0.42 |
| Orange | 0.30 | 0.30 | 0.25 | 0.32 |
| Red | 0.41 | 0.42 | 0.35 | 0.42 |

TABLE 31

Color Breakdown for fluorescence emission of PBT fibers

| Color | Fiber 16 | Fiber 17 | Fiber 18 | Fiber 19 | Fiber 20 |
|---|---|---|---|---|---|
| Purple | 12.13 | 0.47 | 0.17 | 0.19 | 0.78 |
| Blue | 8.37 | 0.22 | 0.09 | 0.10 | 0.44 |

TABLE 31-continued

Color Breakdown for fluorescence emission of PBT fibers

| Color | Fiber 16 | Fiber 17 | Fiber 18 | Fiber 19 | Fiber 20 |
|---|---|---|---|---|---|
| Green | 0.05 | 0.02 | 0.01 | 0.01 | 0.02 |
| Yellow | 0.00 | 0.14 | 0.10 | 0.10 | 0.12 |
| Orange | 0.00 | 0.19 | 0.13 | 0.13 | 0.17 |
| Red | 0.00 | 0.44 | 0.32 | 0.33 | 0.41 |

TABLE 32

Color Breakdown for fluorescence emission of PMMA fibers

| Color | Fiber 21 | Fiber 22 | Fiber 23 | Fiber 24 |
|---|---|---|---|---|
| Purple | 2.21 | 2.97 | 2.68 | 2.62 |
| Blue | 0.78 | 1.41 | 1.24 | 2.25 |
| Green | 0.00 | 0.00 | 0.00 | 0.00 |
| Yellow | 0.03 | 0.02 | 0.02 | 0.01 |

TABLE 32-continued

Color Breakdown for fluorescence emission of PMMA fibers

| Color | Fiber 21 | Fiber 22 | Fiber 23 | Fiber 24 |
|---|---|---|---|---|
| Orange | 0.06 | 0.06 | 0.05 | 0.04 |
| Red | 0.10 | 0.12 | 0.12 | 0.09 |

Figure 2D:
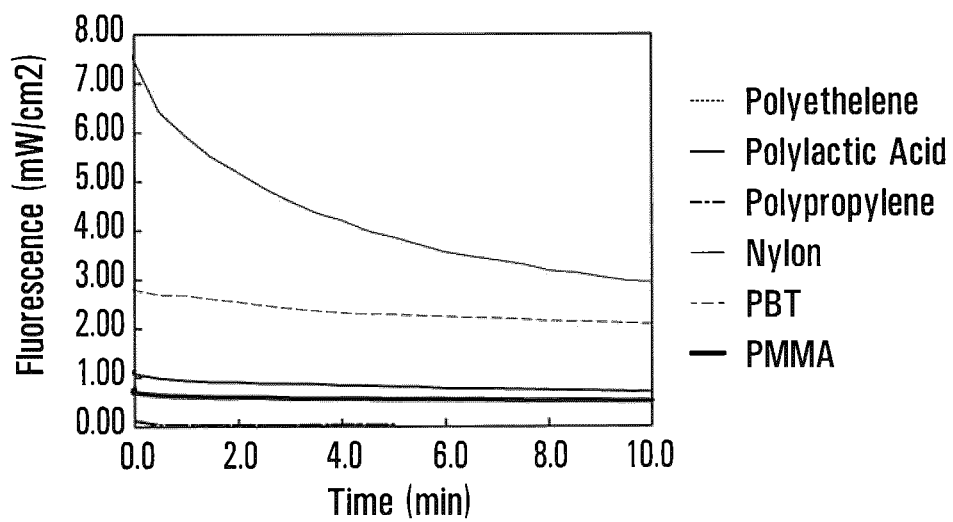

The influence of the polymer on the fluorescence emitted by the fibers was measured and compared between the various fibers prepared. The results are presented in FIG. 2D. The data shows that fibers made from polyethylene and PBT fluoresce the most.

TABLE 33

Color Breakdown for fluorescence emission of the indicated fibers

| Color | Polyethylene | Polylactic Acid | Polypropylene | Nylon | PBT | PMMA |
|---|---|---|---|---|---|---|
| Purple | 8.81 | 2.95 | 7.32 | 2.51 | 0.47 | 2.21 |
| Blue | 5.08 | 1.47 | 4.00 | 1.21 | 0.22 | 0.78 |
| Green | 0.01 | 0.03 | 0.01 | 0.45 | 0.02 | 0.00 |
| Yellow | 0.00 | 0.08 | 0.00 | 0.45 | 0.14 | 0.03 |
| Orange | 0.00 | 0.09 | 0.00 | 0.30 | 0.19 | 0.06 |
| Red | 0.01 | 0.09 | 0.00 | 0.41 | 0.44 | 0.10 |

Example 4

Leaching of Photoactivatable Agent Out of Photoactivatable Fibers

Figure 3:
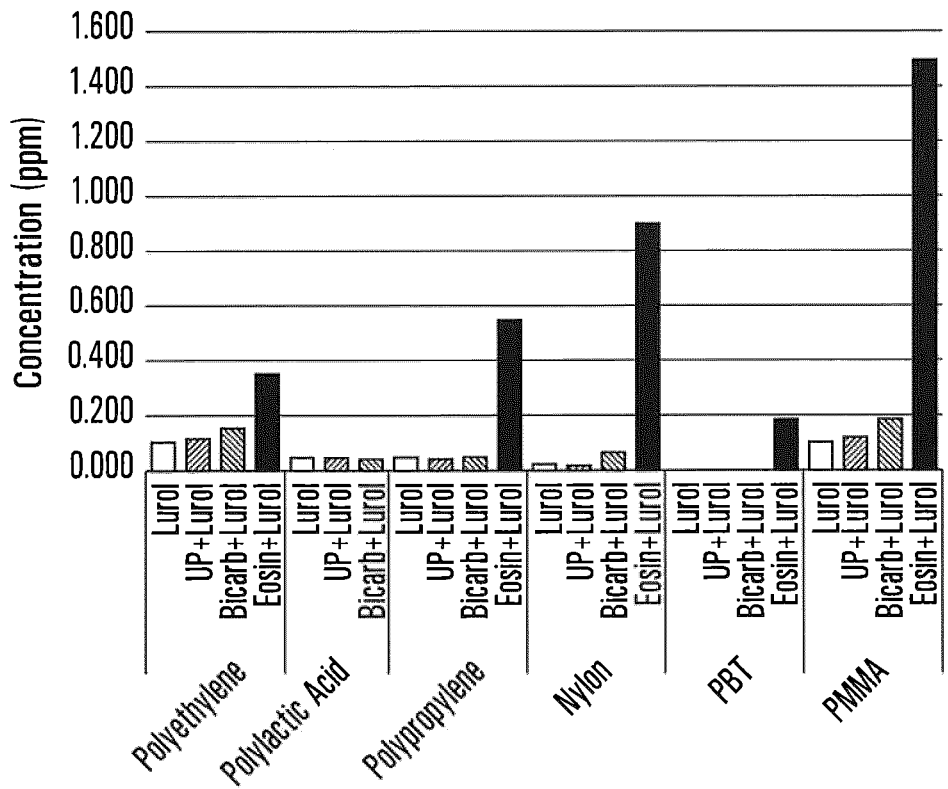
FIG. 3 illustrates a graph comparing the leaching of Eosin out of the indicated photoactivatable fibers according to one embodiment of the present disclosure.

The purpose of this experiment was to determine whether the polymer has an effect on the leaching of the photoactivatable agent out of the photoactivatable fibers. Leaching was measured by placing 0.1 g of fiber in 10 ml of water for 1 day following which the water was assessed for the presence of photoactivatable agent. FIG. 3 shows the leaching of Eosin out of the photoactivatable fibers as defined in Example 3. The detection limit for samples in FIG. 4 was 0.0095 μg/ml. Table 34 outlines the data obtained during this experiment. The data presented in Table 34 and illustrated in FIG. 3 demonstrates that photoactivatable fibers made from polyethylene and photoactivatable fibers made from PBT present the least leaching of Eosin amongst the polymers tested. The data also show that compounding the photoactivatable agent with the polymer of the fiber leads to substantially no leaching of the photoactivatable agent out of the photoactivatable fiber.

TABLE 34

Leaching of Eosin out of photoactivatable fibers as defined in Example 3

| Photoactivatable Fiber | Photoactivatable agent | Concentration in solution (ppm) | % leaching |
|---|---|---|---|
| 1 | Compounded | 0.103 | 0.454 |
| 2 | Compounded | 0.116 | 0.510 |
| 3 | Compounded | 0.154 | 0.676 |
| 4 | Compounded and coated | 0.351 | 1.544 |
| 5 | Compounded | 0.046 | 0.102 |
| 6 | Compounded | 0.046 | 0.102 |
| 7 | Compounded | 0.041 | 0.090 |
| 8 | Compounded | 0.048 | 0.211 |
| 9 | Compounded | 0.041 | 0.183 |
| 10 | Compounded | 0.049 | 0.214 |
| 11 | Compounded and coated | 0.546 | 2.404 |
| 12 | Compounded | 0.022 | 0.099 |
| 13 | Compounded | 0.017 | 0.074 |
| 14 | Compounded | 0.065 | 0.286 |
| 15 | Compounded and coated | 0.899 | 3.957 |
| 17 | Compounded | BDL | N/A |
| 18 | Compounded | BDL | N/A |
| 19 | Compounded | BDL | N/A |
| 20 | Compounded and coated | 0.184337 | 0.4055414 |
| 21 | Compounded | 0.102 | 0.224 |
| 22 | Compounded | 0.118 | 0.261 |
| 23 | Compounded | 0.184 | 0.405 |
| 24 | Compounded and coated | 1.495 | 3.290 |

Example 5

Effect of Varying Lamp Height on Fluorescence Emitted by Photoactivatable Fibers The purpose of this experiment was to determine the effect of varying the blue lamp height on fluorescence emission of the photoactivatable fibers. Measurements are presented in Tables 35-38 below.

TABLE 35

Blue lamp output

| Height (cm) | Energy (J/cm$^2$) | Change in height | Change in energy | Percent Energy increase |
|---|---|---|---|---|
| 5 | 30.43 | | | |
| 3.75 | 39.15 | −1.25 | 8.72 | 22.28 |
| 2.5 | 49.78 | −1.25 | 10.63 | 21.35 |

TABLE 36

Influence of height of blue lamp from nylon photoactivatable fibers on fluorescence emission

| | 0-5 minutes | | | | 5-10 minutes | | | |
|---|---|---|---|---|---|---|---|---|
| Height (cm) | Energy (J/cm$^2$) | Change in height | Change in energy | Percent Energy increase | Energy (J/cm$^2$) | Change in height | Change in energy | Percent Energy increase |
| 5 | 1.59 | | | | 1.02 | | | |
| 3.75 | 1.64 | −1.25 | 0.05 | 3.19 | 0.96 | −1.25 | −0.06 | −6.60 |
| 2.5 | 1.90 | −1.25 | 0.26 | 15.66 | 1.09 | −1.25 | 0.13 | 13.83 |

TABLE 37

Influence of height of blue lamp from PBT photoactivatable fibers on fluorescence emission

| | 0-5 minutes | | | | 5-10 minutes | | | |
|---|---|---|---|---|---|---|---|---|
| Height (cm) | Energy (J/cm$^2$) | Change in height | Change in energy | Percent Energy increase | Energy (J/cm$^2$) | Change in height | Change in energy | Percent Energy increase |
| 5 | 0.77 | | | | 0.67 | | | |
| 2.5 | 1.04 | −2.50 | 0.28 | 26.54 | 0.80 | −2.50 | 0.13 | 19.88 |

TABLE 38

Influence of height of blue lamp from PLA photoactivatable fibers on fluorescence emission

| | 0-5 minutes | | | | 5-10 minutes | | | |
|---|---|---|---|---|---|---|---|---|
| Height (cm) | Energy (J/cm$^2$) | Change in height | Change in energy | Percent Energy increase | Energy (J/cm$^2$) | Change in height | Change in energy | Percent Energy increase |
| 5 | 0.28 | | | | 0.24 | | | |
| 2.5 | 0.39 | −2.50 | 0.11 | 27.25 | 0.25 | −2.50 | 0.01 | 2.83 |

As the blue lamp height decreases, the fluorescence and the energy produced by the photoactivatable fiber increases in a non-linear fashion. For nylon fibers, the effect is seen in the first five minutes. The fluorescence and energy are 12.95 mW/cm$^2$ for fluorescence and 1.90 J/cm$^2$ for energy. After five minutes, it was observed that the fluorescence and the energy were similar. For PBT fibers, decreasing the lamp height increases both fluorescence and energy. However, photobleaching occurs more rapidly. For PLA fibers, decreasing the lamp height increases fluorescence at first. Photobleaching occurs at a rate such that after 7 minutes the fluorescence is lower when the lamp is closer.

Example 6

Effect of Addition of a Lubricant on the Fluorescence Emitted from Eosin Y

Figure 4:
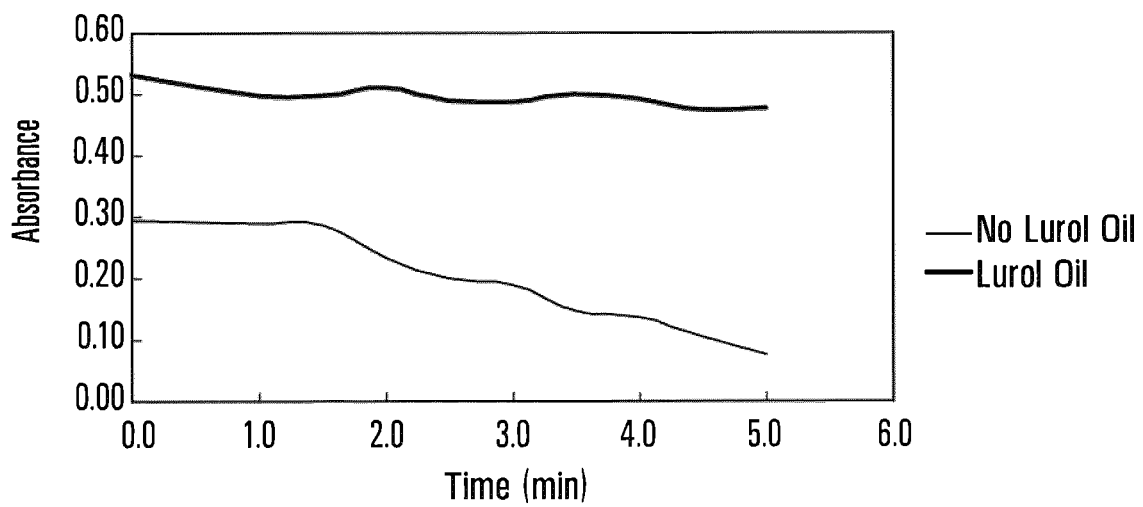
FIG. 4 illustrates a graph showing the effect of addition of a lubricant to fluorescence emission by Eosin Y in solution.

The purpose of this experiment was to assess if addition of a lubricant affects the emission of fluorescence of a solution of Eosin Y. When lurol oil is added to a solution of Eosin Y in water the solution immediately turns from an orange color to a pink color. It also may get slightly bubbly. A quick check of the solution with lurol oil shows that the solution is one layer, completely miscible, with no visible precipitate. The effect of lurol oil was compared by adding 320 μL to a 2 mL solution of 109 μg/g Eosin Y. The no lurol oil solution had 320 μL. of water added. The fluorescence of these two solutions was measured to determine if the lurol oil had any effect (FIG. 4). The results indicated that the lurol oil has an effect of the Eosin Y solution, as the lurol oil solution was almost twice as fluorescent and barely photodegraded. Also, the fluorescence of the lurol oil is red shifted, such that some yellow and orange are observed. Under the blue lamp the lurol oil solution looks almost orange, while the solution without lurol oil was green.

Example 7

Figure 5A:
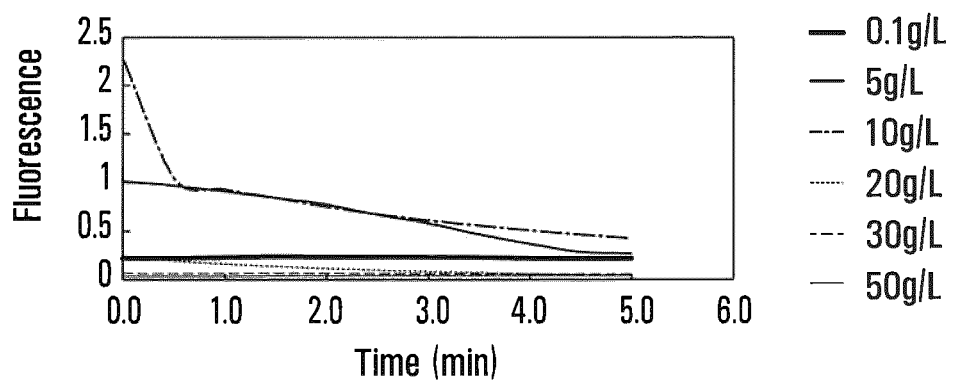
FIGS. 5A-5B.
Figure 5B:
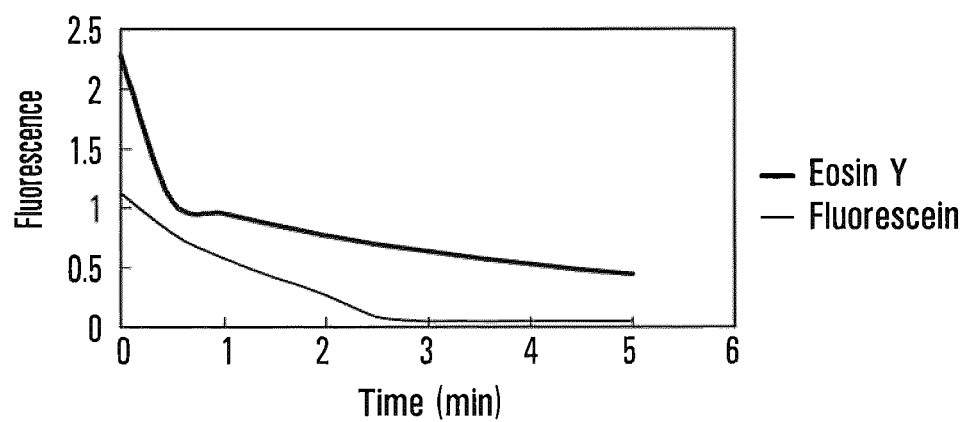

Effect of Addition of a Lubricant on the Fluorescence Emission of Photoactivatable Fibers The presence of a lubricant was shown to have an effect on the doped fibers and their fluorescence. In the case of low concentrations of chromophore it can slightly red shift, and reduces bleaching time considerably. In higher concentrations of chromophore it red shifts, as well as increase fluorescence. The most effect seems to be around 10 g/L of lurol oil. Initially the fluorescence of Eosin Y doped fibers was 0.01 (FIG. 5A), but with the lurol oil added the fluorescence is boosted to 0.7. A comparison was done of Eosin Y and Fluorescein at the same concentration with lurol oil added. It would appear that while they start out similarly in fluorescence, the fluorescein photo-degrades faster (FIG. 5B).

Example 8

Figure 6A:
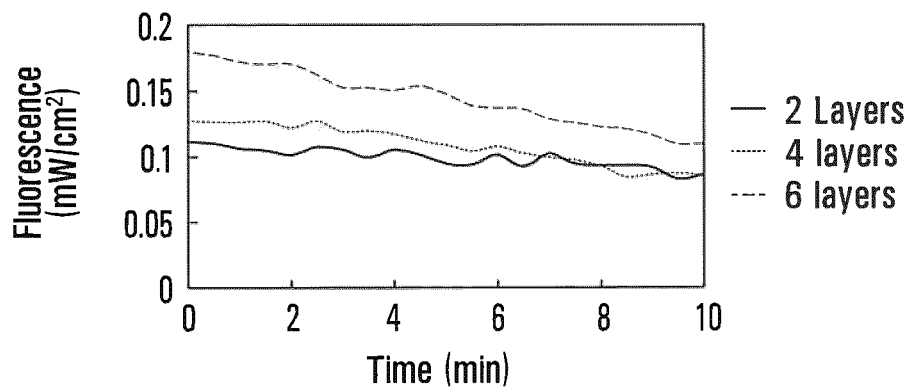
FIGS. 6A-6B.
Figure 6B:
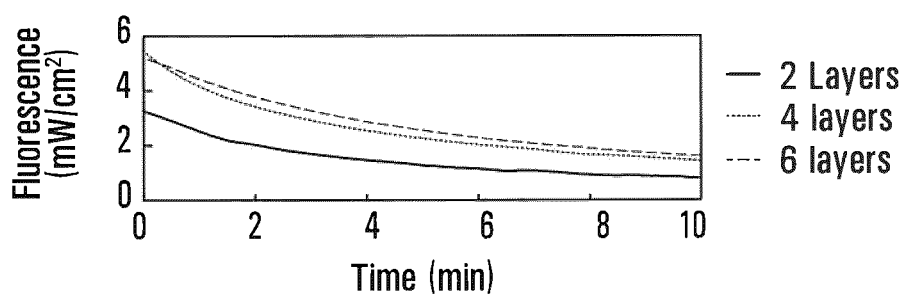

Preparation of Photoactivatable Fibers with Multiple Layers of Photoactivatable Agents The purpose of this experiment was to determine if adding more than one layer of photoactivatable agents onto the polymeric fibers affect the emission of fluorescence. For this, the following photoactivatable fibers were prepared. The polypropylene polymer was compounded with the photoactivatable agent (Eosin Y:fluorescein) at around 0.8-1.0% w/w and the polymer was then hardened and cut into small pieces. This polymer was processed into the hopper and it was extruded into a fiber at specific micron sizes (FIG. 6A: 31 microns) (FIG. 6B: 93 microns). As it was exiting from the machine head, it was sprayed with a composition of lurol oil alone, or with a composition of lurol oil and photoactivatable agent, or with a composition of lurol oil and urea peroxide, or with a composition of lurol oil and sodium bicarbonate.

The amount of fluorophore is determinant for overall fluorescence of the photoactivatable fibers. As the layer level increases the overall fluorescence also increases. The increase is not linear, and doubling the fiber content does not double the fluorescence. It is clear however that 6 layers out preforms both 4 and 2 layers of the same material.

Example 9

Figure 7:
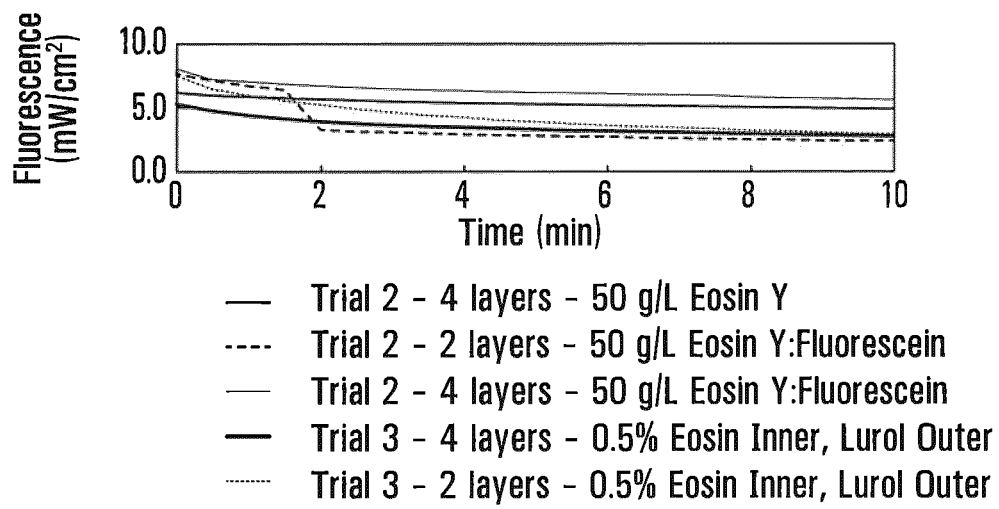
FIG. 7 illustrates a graph comparing the fluorescence emission of over time of photoactivatable nylon fibers according to one embodiment of the present disclosure having the photoactivatable agent present inside of the photoactivatable nylon fibers (inner) or on the surface (outer).

Influence of with Multiple Layers of Photoactivatable Agents on Fluorescence Emission When the chromophore is situated on the surface of the polymeric fibers, increasing the number of layers also increases the fluorescence of the polymeric fiber. When the chromophore is on the inside, the opposite happens, increasing the number of layers decreases overall fluorescence. The photoactivatable fibers were prepared as described in Example 8. Photobleaching occurs more rapidly when the chromophore is on the inside (FIG. 7). When comparing the 4 layer 50 g/L Eosin Y Outer from Trial 2 and 4 layer 0.5% Eosin Y Inner from Trial 3, the rate of photobleaching is faster when Eosin Y is compounded with nylon. Nylon trial 3 was more successful than nylon trial 2. With less chromophore within the fiber and with less layers, it fluoresced more than with the chromophore coating the fiber. However, photobleaching occurs at a much faster rate. A difference of 2 mW/cm$^2$ is observed between them after 10 minutes.

TABLE 39

Color breakdown of the fluorescence emitted

| Color | Trial 2 4 layers 50 g/L Eosin Y | Trial 2 2 layers 50 g/L E:F | Trial 2 4 layers 50 g/L E:F | Trial 3 2 layers 0.5% Eosin Inner Lurol Oil Outer | Trial 3 4 layers 0.5% Eosin Inner Lurol Oil Outer |
|---|---|---|---|---|---|
| Purple | 2.63 | 6.21 | 1.87 | 2.51 | 0.29 |
| Blue | 1.27 | 3.49 | 0.90 | 1.21 | 0.08 |
| Green | 0.22 | 0.32 | 0.31 | 0.45 | 0.21 |
| Yellow | 0.56 | 0.47 | 0.66 | 0.45 | 0.35 |
| Orange | 0.44 | 0.34 | 0.51 | 0.30 | 0.26 |
| Red | 0.50 | 0.27 | 0.60 | 0.41 | 0.41 |

TABLE 40

Nylon Run 1-103 microns E/F 10 g/L-4 Layers 0-5 min

| Nylon Run 1-103 microns | | mW/cm2 at 5 cm | | | | | | |
|---|---|---|---|---|---|---|---|---|
| E/F 10 g/L-4 Layers 0-5 min | | 0 | 0.5 min | 1 min | 1.5 min | 2 min | 2.5 min | 3 min |
| Lamp | 400-518 | 21.47 | 24.99 | 25.79 | 26.31 | 26.83 | 27.22 | 27.44 |
| Fluoresc. | 519-760 | 3.12 | 5.17 | 4.70 | 4.34 | 4.03 | 3.85 | 3.68 |
| total | 400-760 | 24.58338 | 30.15935 | 30.49297 | 30.65144 | 30.85972 | 31.07188 | 31.11921 |
| % fluorescence | | 12.7% | 17.1% | 15.4% | 14.2% | 13.1% | 12.4% | 11.8% |
| purple | (400)-450 | 14.2387 | 15.8609 | 16.1645 | 16.2767 | 16.4031 | 16.5001 | 16.5381 |
| Blue | 450-500 | 7.2285 | 8.9835 | 9.4986 | 9.9158 | 10.3133 | 10.6121 | 10.7933 |
| Green | 500-570 | 1.2302 | 2.1414 | 1.9567 | 1.7172 | 1.5957 | 1.5291 | 1.4669 |
| Yellow | 570-591 | 1.1034 | 1.4359 | 1.3037 | 1.1519 | 1.0679 | 1.0119 | 0.9749 |
| Orange | 591-610 | 0.6207 | 0.8740 | 0.7901 | 0.7554 | 0.7005 | 0.6657 | 0.6391 |
| Red | 610-760 | 0.1814 | 0.8965 | 0.8084 | 0.8645 | 0.8071 | 0.7795 | 0.7324 |
| total | (400-700) | 24.60 | 30.19 | 30.52 | 30.68 | 30.89 | 31.10 | 31.14 |

| Nylon Run 1-103 microns | | mW/cm2 at 5 cm | | | | |
|---|---|---|---|---|---|---|
| E/F 10 g/L-4 Layers 0-5 min | | 3.5 min | 4 min | 4.5 min | 5 min | J/cm2 |
| Lamp | 400-518 | 27.69 | 27.95 | 28.21 | 28.36 | 7.92 | 87.0% |
| Fluoresc. | 519-760 | 3.53 | 3.49 | 3.32 | 3.17 | 1.18 | 12.9% |
| total | 400-760 | 31.21439 | 31.43356 | 31.52938 | 31.53128 | 9.09 | 99.9% |
| % fluorescence | | 11.3% | 11.1% | 10.5% | 10.0% | 0.13 | 12.9% |
| purple | (400)-450 | 16.5781 | 16.6734 | 16.7323 | 16.7269 | 4.86 | 53.4% |
| Blue | 450-500 | 11.0066 | 11.1705 | 11.3788 | 11.5401 | 3.03 | 33.3% |
| Green | 500-570 | 1.4155 | 1.3995 | 1.3350 | 1.2853 | 0.47 | 5.2% |
| Yellow | 570-591 | 0.9367 | 0.9109 | 0.8637 | 0.8309 | 0.32 | 3.5% |
| Orange | 591-610 | 0.6134 | 0.5987 | 0.5662 | 0.5442 | 0.20 | 2.2% |
| Red | 610-760 | 0.6883 | 0.7045 | 0.6760 | 0.6255 | 0.21 | 2.4% |
| total | (400-700) | 31.24 | 31.46 | 31.55 | 31.55 | 9.10 | 100.0% |

TABLE 41

| Nylon Run 1-103 microns E/F 20 g/L-4 Layers 0-5 min | | | | | | | | |
|---|---|---|---|---|---|---|---|---|
| Nylon Run 1-103 microns | | mW/cm2 at 5 cm | | | | | | |
| E/F 10 g/L-4 Layers 0-5 min | | 0 | 0.5 min | 1 min | 1.5 min | 2 min | 2.5 min | 3 min |
| Lamp | 400-518 | 19.40 | 21.27 | 22.67 | 22.77 | 23.13 | 23.67 | 24.11 |
| Fluoresc. | 519-760 | 7.72 | 6.40 | 5.79 | 5.81 | 5.63 | 5.45 | 5.18 |
| total | 400-760 | 27.12141 | 27.67375 | 28.45756 | 28.58048 | 28.76461 | 29.12852 | 29.29128 |
| % fluorescence | | 28.5% | 23.1% | 20.4% | 20.3% | 19.6% | 18.7% | 17.7% |
| purple | (400)-450 | 12.6847 | 13.4080 | 14.0379 | 14.1004 | 14.2567 | 14.5022 | 14.6514 |
| Blue | 450-500 | 6.6370 | 7.7965 | 8.5687 | 8.6018 | 8.8139 | 9.1072 | 9.4021 |
| Green | 500-570 | 2.2366 | 1.8797 | 1.6972 | 1.7004 | 1.6593 | 1.6050 | 1.5366 |
| Yellow | 570-591 | 2.4298 | 1.9811 | 1.7822 | 1.7786 | 1.7244 | 1.6595 | 1.5891 |
| Orange | 591-610 | 1.5572 | 1.2861 | 1.1626 | 1.1594 | 1.1250 | 1.0824 | 1.0351 |
| Red | 610-760 | 1.6340 | 1.3711 | 1.2534 | 1.2832 | 1.2280 | 1.2135 | 1.1167 |
| total | (400-700) | 27.18 | 27.72 | 28.50 | 28.62 | 28.81 | 29.17 | 29.33 |

| Nylon Run 1-103 microns | | mW/cm2 at 5 cm | | | | | |
|---|---|---|---|---|---|---|---|
| E/F 10 g/L-4 Layers 0-5 min | | 3.5 min | 4 min | 4.5 min | 5 min | J/cm2 | |
| Lamp | 400-518 | 24.51 | 24.92 | 25.30 | 25.57 | 6.95 | 80.2% |
| Fluoresc. | 519-760 | 5.03 | 4.87 | 4.75 | 4.66 | 1.70 | 19.6% |
| total | 400-760 | 29.53686 | 29.79402 | 30.04862 | 30.22247 | 8.65 | 99.9% |
| % fluorescence | | 17.0% | 16.4% | 15.8% | 15.4% | 0.20 | 19.6% |
| purple | (400)-450 | 14.8214 | 14.9772 | 15.1395 | 15.2521 | 4.28 | 49.4% |
| Blue | 450-500 | 9.6311 | 9.8833 | 10.0927 | 10.2565 | 2.66 | 30.7% |
| Green | 500-570 | 1.4934 | 1.4625 | 1.4331 | 1.4059 | 0.50 | 5.8% |
| Yellow | 570-591 | 1.5402 | 1.4879 | 1.4429 | 1.4163 | 0.52 | 6.0% |
| Orange | 591-610 | 1.0043 | 0.9687 | 0.9394 | 0.9180 | 0.34 | 3.9% |
| Red | 610-760 | 1.0842 | 1.0517 | 1.0368 | 1.0080 | 0.37 | 4.2% |
| total | (400-700) | 29.57 | 29.83 | 30.08 | 30.26 | 8.66 | 100.0% |

TABLE 42

| Nylon Run 7 Fluorescein 35 g/L-4 Layers 0-5 min | | | | | | | | |
|---|---|---|---|---|---|---|---|---|
| Nylon Run 7 Fluorescein | | mW/cm2 at 5 cm | | | | | | |
| 35 g/L-4 Layers 0-5 min | | 0 | 0.5 min | 1 min | 1.5 min | 2 min | 2.5 min | 3 min |
| Lamp | 400-518 | 10.68 | 11.92 | 12.89 | 13.63 | 14.33 | 14.95 | 15.60 |
| Fluoresc. | 519-760 | 10.30 | 9.13 | 8.49 | 8.01 | 7.59 | 7.16 | 6.83 |
| total | 400-760 | 20.98009 | 21.05839 | 21.38843 | 21.64094 | 21.92016 | 22.11076 | 22.42923 |
| % fluorescence | | 49.1% | 43.4% | 39.7% | 37.0% | 34.6% | 32.4% | 30.4% |
| purple | (400)-450 | 6.7401 | 7.2458 | 7.6859 | 8.0035 | 8.3020 | 8.5583 | 8.8489 |
| Blue | 450-500 | 3.5037 | 4.2174 | 4.7250 | 5.1256 | 5.5065 | 5.8505 | 6.2007 |
| Green | 500-570 | 6.4483 | 5.8166 | 5.4777 | 5.2332 | 5.0226 | 4.8153 | 4.6339 |
| Yellow | 570-591 | 1.8820 | 1.6354 | 1.4990 | 1.3971 | 1.3096 | 1.2236 | 1.1540 |
| Orange | 591-610 | 1.0807 | 0.9469 | 0.8767 | 0.8197 | 0.7732 | 0.7270 | 0.6870 |
| Red | 610-760 | 1.3665 | 1.2324 | 1.1575 | 1.0932 | 1.0361 | 0.9634 | 0.9312 |
| total | (400-700) | 21.02 | 21.09 | 21.42 | 21.67 | 21.95 | 22.14 | 22.46 |

| Nylon Run 7 Fluorescein | | mW/cm2 at 5 cm | | | | | |
|---|---|---|---|---|---|---|---|
| 35 g/L-4 Layers 0-5 min | | 3.5 min | 4 min | 4.5 min | 5 min | J/cm2 | |
| Lamp | 400-518 | 16.21 | 16.71 | 17.21 | 17.61 | 4.32 | 65.4% |
| Fluoresc. | 519-760 | 6.42 | 6.17 | 5.88 | 5.65 | 2.28 | 34.5% |
| total | 400-760 | 22.63264 | 22.88359 | 23.0868 | 23.25756 | 6.60 | 99.9% |
| % fluorescence | | 28.4% | 27.0% | 25.5% | 24.3% | 0.35 | 34.5% |
| purple | (400)-450 | 9.0966 | 9.3179 | 9.5100 | 9.6820 | 2.50 | 37.8% |
| Blue | 450-500 | 6.5468 | 6.8184 | 7.1173 | 7.3422 | 1.67 | 25.2% |
| Green | 500-570 | 4.4415 | 4.3017 | 4.1459 | 4.0237 | 1.51 | 22.8% |

TABLE 42-continued

| Nylon Run 7 Fluorescein 35 g/L-4 Layers 0-5 min | | | | | | | |
|---|---|---|---|---|---|---|---|
| Yellow | 570-591 | 1.0778 | 1.0244 | 0.9718 | 0.9246 | 0.40 | 6.0% |
| Orange | 591-610 | 0.6431 | 0.6127 | 0.5811 | 0.5564 | 0.23 | 3.5% |
| Red | 610-760 | 0.8515 | 0.8318 | 0.7831 | 0.7505 | 0.31 | 4.6% |
| total | (400-700) | 22.66 | 22.91 | 23.11 | 23.28 | 6.61 | 100.0% |

TABLE 43

Nylon Run 9C-103 microns E/F 30/7.5/7.5-4 Layers 0-5 min

| Nylon Run 9C-103 microns E/F 30/7.5/7.5-4 | | mW/cm2 at 5 cm | | | | | | |
|---|---|---|---|---|---|---|---|---|
| Layers 0-5 min | | 0 | 0.5 min | 1 min | 1.5 min | 2 min | 2.5 min | 3 min |
| Lamp | 400-518 | 20.92 | 21.07 | 21.36 | 21.56 | 21.77 | 21.82 | 21.92 |
| Fluoresc. | 519-760 | 1.54 | 1.41 | 1.39 | 1.36 | 1.36 | 1.34 | 1.34 |
| total | 400-760 | 22.45942 | 22.48255 | 22.74403 | 22.9241 | 23.12528 | 23.16169 | 23.26146 |
| % fluorescence | | 6.9% | 6.3% | 6.1% | 5.9% | 5.9% | 5.8% | 5.8% |
| purple | (400)-450 | 14.2461 | 14.0180 | 14.0744 | 14.0780 | 14.0611 | 14.0484 | 14.0565 |
| Blue | 450-500 | 6.6739 | 7.0542 | 7.2817 | 7.4833 | 7.7090 | 7.7720 | 7.8656 |
| Green | 500-570 | 0.0700 | 0.0640 | 0.0625 | 0.0652 | 0.0690 | 0.0682 | 0.0698 |
| Yellow | 570-591 | 0.3880 | 0.3600 | 0.3510 | 0.3480 | 0.3480 | 0.3455 | 0.3465 |
| Orange | 591-610 | 0.5250 | 0.4839 | 0.4742 | 0.4657 | 0.4584 | 0.4548 | 0.4544 |
| Red | 610-760 | 0.5830 | 0.5270 | 0.5243 | 0.5075 | 0.5028 | 0.4956 | 0.4916 |
| total | (400-700) | 22.49 | 22.51 | 22.77 | 22.95 | 23.15 | 23.18 | 23.28 |

| Nylon Run 9C-103 microns E/F 30/7.5/7.5-4 | | mW/cm2 at 5 cm | | | | | |
|---|---|---|---|---|---|---|---|
| Layers 0-5 min | | 3.5 min | 4 min | 4.5 min | 5 min | J/cm2 | |
| Lamp | 400-518 | 22.02 | 22.17 | 22.33 | 22.48 | 6.51 | 94.0% |
| Fluoresc. | 519-760 | 1.33 | 1.29 | 1.31 | 1.30 | 0.41 | 5.9% |
| total | 400-760 | 23.35004 | 23.46191 | 23.64257 | 23.78278 | 6.92 | 99.9% |
| % fluorescence | | 5.7% | 5.5% | 5.5% | 5.5% | 0.06 | 5.9% |
| purple | (400)-450 | 14.0161 | 14.0168 | 14.0343 | 14.0449 | 4.22 | 60.9% |
| Blue | 450-500 | 8.0056 | 8.1532 | 8.3002 | 8.4356 | 2.29 | 33.1% |
| Green | 500-570 | 0.0715 | 0.0696 | 0.0761 | 0.0801 | 0.02 | 0.3% |
| Yellow | 570-591 | 0.3454 | 0.3405 | 0.3456 | 0.3501 | 0.11 | 1.5% |
| Orange | 591-610 | 0.4491 | 0.4407 | 0.4421 | 0.4408 | 0.14 | 2.0% |
| Red | 610-760 | 0.4848 | 0.4631 | 0.4663 | 0.4531 | 0.15 | 2.2% |
| total | (400-700) | 23.37 | 23.48 | 23.66 | 23.80 | 6.93 | 100.0% |

TABLE 44

Polypropylene Run 10 Fluorescein 35 g/L-4 Layers 0-5 min

| Polypropylene Run 10 Fluorescein 35 g/L-4 | | mW/cm2 at 5 cm | | | | | | |
|---|---|---|---|---|---|---|---|---|
| Layers 0-5 min | | 0 | 0.5 min | 1 min | 1.5 min | 2 min | 2.5 min | 3 min |
| Lamp | 400-518 | 34.75 | 35.18 | 35.26 | 35.19 | 35.26 | 35.20 | 35.11 |
| Fluoresc. | 519-760 | 0.58 | 0.63 | 0.60 | 0.46 | 0.45 | 0.41 | 0.38 |
| total | 400-760 | 35.32948 | 35.80934 | 35.85791 | 35.65735 | 35.70358 | 35.60884 | 35.48748 |
| % fluorescence | | 1.6% | 1.8% | 1.7% | 1.3% | 1.3% | 1.1% | 1.1% |
| purple | (400)-450 | 21.5860 | 21.4518 | 21.3402 | 20.8147 | 20.7911 | 20.6313 | 20.4316 |
| Blue | 450-500 | 13.0286 | 13.5733 | 13.7616 | 14.2367 | 14.3212 | 14.4363 | 14.5448 |
| Green | 500-570 | 0.5551 | 0.5656 | 0.5458 | 0.4488 | 0.4390 | 0.4082 | 0.3877 |
| Yellow | 570-591 | 0.1004 | 0.1011 | 0.0941 | 0.0763 | 0.0704 | 0.0666 | 0.0622 |

TABLE 44-continued

Polypropylene Run 10 Fluorescein 35 g/L-4 Layers 0-5 min

| | | | | | | | | |
|---|---|---|---|---|---|---|---|---|
| Orange | 591-610 | 0.0477 | 0.0609 | 0.0577 | 0.0443 | 0.0441 | 0.0397 | 0.0369 |
| Red | 610-760 | 0.0132 | 0.0590 | 0.0608 | 0.0382 | 0.0396 | 0.0282 | 0.0258 |
| total | (400-700) | 35.33 | 35.81 | 35.86 | 35.66 | 35.71 | 35.61 | 35.49 |

| Polypropylene Run 10 Fluorescein 35 g/L-4 Layers 0-5 min | | mW/cm2 at 5 cm | | | | | |
|---|---|---|---|---|---|---|---|
| | | 3.5 min | 4 min | 4.5 min | 5 min | J/cm2 | |
| Lamp | 400-518 | 35.10 | 34.95 | 34.88 | 34.86 | 10.53 | 98.7% |
| Fluoresc. | 519-760 | 0.37 | 0.31 | 0.30 | 0.29 | 0.13 | 1.3% |
| total | 400-760 | 35.47158 | 35.25517 | 35.18271 | 35.15384 | 10.66 | 100.0% |
| % fluorescence | | 1.0% | 0.9% | 0.9% | 0.8% | 0.01 | 1.3% |
| purple | (400)-450 | 20.3492 | 20.1362 | 20.0194 | 19.9225 | 6.23 | 58.4% |
| Blue | 450-500 | 14.6194 | 14.6803 | 14.7432 | 14.8173 | 4.26 | 39.9% |
| Green | 500-570 | 0.3818 | 0.3440 | 0.3258 | 0.3198 | 0.13 | 1.2% |
| Yellow | 570-591 | 0.0591 | 0.0486 | 0.0467 | 0.0454 | 0.02 | 0.2% |
| Orange | 591-610 | 0.0364 | 0.0289 | 0.0289 | 0.0273 | 0.01 | 0.1% |
| Red | 610-760 | 0.0271 | 0.0182 | 0.0197 | 0.0226 | 0.01 | 0.1% |
| total | (400-700) | 35.47 | 35.26 | 35.18 | 35.15 | 10.66 | 100.0% |

TABLE 45

Polypropylene Run 12 Eosin y 25 g/L-4 Layers 0-5 min

| Polypropylene Run 12 Eosin y 25 g/L-4 Layers 0-5 min | | mW/cm2 at 5 cm | | | | | | |
|---|---|---|---|---|---|---|---|---|
| | | 0 | 0.5 min | 1 min | 1.5 min | 2 min | 2.5 min | 3 min |
| Lamp | 400-518 | 20.35 | 20.29 | 20.27 | 20.23 | 20.19 | 20.17 | 20.12 |
| Fluoresc. | 519-760 | 0.84 | 0.81 | 0.80 | 0.79 | 0.78 | 0.78 | 0.77 |
| total | 400-760 | 21.1856 | 21.09802 | 21.06914 | 21.02316 | 20.96994 | 20.94642 | 20.8899 |
| % fluorescence | | 4.0% | 3.8% | 3.8% | 3.8% | 3.7% | 3.7% | 3.7% |
| purple | (400)-450 | 13.7608 | 13.4286 | 13.2875 | 13.1247 | 12.9928 | 12.8698 | 12.7363 |
| Blue | 450-500 | 6.5846 | 6.8630 | 6.9810 | 7.1075 | 7.1948 | 7.2987 | 7.3816 |
| Green | 500-570 | 0.1434 | 0.1414 | 0.1371 | 0.1356 | 0.1310 | 0.1287 | 0.1287 |
| Yellow | 570-591 | 0.2980 | 0.2976 | 0.2957 | 0.2925 | 0.2902 | 0.2867 | 0.2854 |
| Orange | 591-610 | 0.2576 | 0.2460 | 0.2432 | 0.2400 | 0.2387 | 0.2383 | 0.2366 |
| Red | 610-760 | 0.1509 | 0.1306 | 0.1338 | 0.1319 | 0.1314 | 0.1333 | 0.1302 |
| total | (400-700) | 21.20 | 21.11 | 21.08 | 21.03 | 20.98 | 20.96 | 20.90 |

| Polypropylene Run 12 Eosin y 25 g/L-4 Layers 0-5 min | | mW/cm2 at 5 cm | | | | | |
|---|---|---|---|---|---|---|---|
| | | 3.5 min | 4 min | 4.5 min | 5 min | J/cm2 | |
| Lamp | 400-518 | 20.13 | 20.09 | 20.11 | 20.09 | 6.06 | 96.2% |
| Fluoresc. | 519-760 | 0.77 | 0.76 | 0.76 | 0.76 | 0.24 | 3.7% |
| total | 400-760 | 20.89411 | 20.85018 | 20.8722 | 20.85232 | 6.29 | 100.0% |
| % fluorescence | | 3.7% | 3.6% | 3.7% | 3.7% | 0.04 | 3.7% |
| purple | (400)-450 | 12.6547 | 12.5548 | 12.4838 | 12.4130 | 3.90 | 61.9% |
| Blue | 450-500 | 7.4711 | 7.5354 | 7.6239 | 7.6759 | 2.16 | 34.3% |
| Green | 500-570 | 0.1258 | 0.1257 | 0.1261 | 0.1258 | 0.04 | 0.6% |
| Yellow | 570-591 | 0.2838 | 0.2835 | 0.2843 | 0.2841 | 0.09 | 1.4% |
| Orange | 591-610 | 0.2356 | 0.2336 | 0.2341 | 0.2328 | 0.07 | 1.1% |
| Red | 610-760 | 0.1320 | 0.1260 | 0.1290 | 0.1295 | 0.04 | 0.6% |
| total | (400-700) | 20.90 | 20.86 | 20.88 | 20.86 | 6.30 | 100.0% |

TABLE 46

Polypropylene Run 15B E/F/RB 20/5/5 (g/L)-4 Layers 0-5 min

| Polypropylene Run 15B E/F/RB 20/5/5 (g/L)-4 Layers 0-5 min | | mW/cm2 at 5 cm | | | | | | |
|---|---|---|---|---|---|---|---|---|
| | | 0 | 0.5 min | 1 min | 1.5 min | 2 min | 2.5 min | 3 min |
| Lamp | 400-518 | 25.41 | 25.50 | 25.59 | 25.65 | 25.72 | 25.76 | 25.80 |
| Fluoresc. | 519-760 | 0.83 | 0.78 | 0.76 | 0.74 | 0.73 | 0.72 | 0.71 |
| total | 400-760 | 26.23634 | 26.28132 | 26.34717 | 26.39618 | 26.44999 | 26.4881 | 26.5104 |
| % fluorescence | | 3.2% | 3.0% | 2.9% | 2.8% | 2.8% | 2.7% | 2.7% |
| purple | (400)-450 | 16.5085 | 16.3661 | 16.2357 | 16.1308 | 16.0312 | 15.9348 | 15.8525 |
| Blue | 450-500 | 8.8967 | 9.1325 | 9.3518 | 9.5209 | 9.6896 | 9.8291 | 9.9452 |
| Green | 500-570 | 0.0424 | 0.0335 | 0.0338 | 0.0317 | 0.0318 | 0.0339 | 0.0339 |
| Yellow | 570-591 | 0.2430 | 0.2265 | 0.2220 | 0.2187 | 0.2144 | 0.2158 | 0.2143 |
| Orange | 591-610 | 0.2914 | 0.2797 | 0.2711 | 0.2657 | 0.2593 | 0.2577 | 0.2525 |
| Red | 610-760 | 0.2676 | 0.2562 | 0.2455 | 0.2408 | 0.2358 | 0.2289 | 0.2237 |
| total | (400-700) | 26.25 | 26.29 | 26.36 | 26.41 | 26.46 | 26.50 | 26.52 |

| Polypropylene Run 15B E/F/RB 20/5/5 (g/L)-4 Layers 0-5 min | | mW/cm2 at 5 cm | | | | | |
|---|---|---|---|---|---|---|---|
| | | 3.5 min | 4 min | 4.5 min | 5 min | J/cm2 | |
| Lamp | 400-518 | 25.82 | 25.85 | 25.91 | 25.94 | 7.71 | 97.2% |
| Fluoresc. | 519-760 | 0.70 | 0.69 | 0.68 | 0.68 | 0.22 | 2.8% |
| total | 400-760 | 26.51969 | 26.5395 | 26.5943 | 26.62222 | 7.93 | 100.0% |
| % fluorescence | | 2.6% | 2.6% | 2.6% | 2.6% | 0.03 | 2.8% |
| purple | (400)-450 | 15.7523 | 15.7119 | 15.6652 | 15.6041 | 4.81 | 60.6% |
| Blue | 450-500 | 10.0682 | 10.1388 | 10.2448 | 10.3347 | 2.90 | 36.6% |
| Green | 500-570 | 0.0342 | 0.0351 | 0.0372 | 0.0380 | 0.01 | 0.1% |
| Yellow | 570-591 | 0.2133 | 0.2104 | 0.2097 | 0.2118 | 0.07 | 0.8% |
| Orange | 591-610 | 0.2497 | 0.2456 | 0.2409 | 0.2387 | 0.08 | 1.0% |
| Red | 610-760 | 0.2135 | 0.2088 | 0.2076 | 0.2058 | 0.07 | 0.9% |
| total | (400-700) | 26.53 | 26.55 | 26.61 | 26.63 | 7.93 | 100.0% |

TABLE 47

Polypropylene core with Polyethylene sheath, Fluorescein, 30 g/L-4 Layers 0-5 min

| Polypropylene core with Polyethylene sheath, Fluorescein, 30 g/L-4 Layers 0-5 min | | mW/cm2 at 5 cm | | | | | | |
|---|---|---|---|---|---|---|---|---|
| | | 0 | 0.5 min | 1 min | 1.5 min | 2 min | 2.5 min | 3 min |
| Lamp | 400-518 | 23.10 | 24.18 | 24.29 | 24.54 | 24.89 | 25.20 | 25.33 |
| Fluoresc. | 519-760 | 1.91 | 1.56 | 1.52 | 1.43 | 1.27 | 1.16 | 1.06 |
| total | 400-760 | 25.01102 | 25.73662 | 25.8135 | 25.97069 | 26.16178 | 26.35745 | 26.39481 |
| % fluorescence | | 7.6% | 6.0% | 5.9% | 5.5% | 4.9% | 4.4% | 4.0% |
| purple | (400)-450 | 14.4848 | 14.7578 | 14.8113 | 14.8620 | 14.9236 | 14.9942 | 14.9548 |
| Blue | 450-500 | 8.4257 | 9.2502 | 9.3024 | 9.5154 | 9.8149 | 10.0590 | 10.2412 |
| Green | 500-570 | 1.2588 | 1.0645 | 1.0456 | 0.9803 | 0.8771 | 0.8112 | 0.7264 |
| Yellow | 570-591 | 0.3698 | 0.3003 | 0.2976 | 0.2783 | 0.2503 | 0.2278 | 0.2113 |
| Orange | 591-610 | 0.2250 | 0.1784 | 0.1778 | 0.1635 | 0.1457 | 0.1334 | 0.1285 |
| Red | 610-760 | 0.2560 | 0.1919 | 0.1862 | 0.1777 | 0.1555 | 0.1368 | 0.1378 |
| total | (400-700) | 25.02 | 25.74 | 25.82 | 25.98 | 26.17 | 26.36 | 26.40 |

| Polypropylene core with Polyethylene sheath, Fluorescein, 30 g/L-4 Layers 0-5 min | | mW/cm2 at 5 cm | | | | | |
|---|---|---|---|---|---|---|---|
| | | 3.5 min | 4 min | 4.5 min | 5 min | J/cm2 | |
| Lamp | 400-518 | 25.54 | 25.68 | 25.76 | 25.83 | 7.46 | 95.1% |
| Fluoresc. | 519-760 | 0.99 | 0.96 | 0.88 | 0.84 | 0.38 | 4.9% |
| total | 400-760 | 26.52577 | 26.64275 | 26.64462 | 26.66904 | 7.84 | 100.0% |
| % fluorescence | | 3.7% | 3.6% | 3.3% | 3.1% | 0.05 | 4.9% |
| purple | (400)-450 | 14.9895 | 14.9871 | 14.9555 | 14.9339 | 4.46 | 56.9% |
| Blue | 450-500 | 10.4189 | 10.5712 | 10.6820 | 10.7803 | 2.95 | 37.6% |

TABLE 47-continued

Polypropylene core with Polyethylene sheath, Fluorescein, 30 g/L-4 Layers 0-5 min

| | | | | | | | |
|---|---|---|---|---|---|---|---|
| Green | 500-570 | 0.6795 | 0.6468 | 0.6059 | 0.5693 | 0.26 | 3.3% |
| Yellow | 570-591 | 0.1983 | 0.1879 | 0.1763 | 0.1669 | 0.07 | 1.0% |
| Orange | 591-610 | 0.1196 | 0.1159 | 0.1082 | 0.1014 | 0.04 | 0.6% |
| Red | 610-760 | 0.1247 | 0.1385 | 0.1210 | 0.1213 | 0.05 | 0.6% |
| total | (400-700) | 26.53 | 26.65 | 26.65 | 26.67 | 7.84 | 100.0% |

TABLE 48

Polypropylene core/Polyethylene sheath, E:F:RB, 20 g/:5 g/L:5 g/L-4 Layers 0-5 min

| Polypropylene core/Polyethylene sheath, E:F:RB, 20 g/:5 g/L:5 g/L-4 Layers 0-5 min | | mW/cm2 at 5 cm | | | | | |
|---|---|---|---|---|---|---|---|
| | | 0 | 0.5 min | 1 min | 1.5 min | 2 min | 2.5 min | 3 min |
| Lamp | 400-518 | 23.53 | 23.65 | 23.69 | 23.72 | 23.77 | 23.77 | 23.83 |
| Fluoresc. | 519-760 | 0.98 | 0.94 | 0.89 | 0.87 | 0.85 | 0.83 | 0.82 |
| total | 400-760 | 24.50132 | 24.58279 | 24.58891 | 24.59305 | 24.62182 | 24.6087 | 24.65408 |
| % fluorescence | | 4.0% | 3.8% | 3.6% | 3.5% | 3.4% | 3.4% | 3.3% |
| purple | (400)-450 | 15.7772 | 15.6065 | 15.4681 | 15.3450 | 15.1697 | 15.0644 | 15.0060 |
| Blue | 450-500 | 7.7480 | 8.0411 | 8.2265 | 8.3771 | 8.6030 | 8.7102 | 8.8288 |
| Green | 500-570 | 0.0396 | 0.0323 | 0.0291 | 0.0276 | 0.0286 | 0.0265 | 0.0275 |
| Yellow | 570-591 | 0.2661 | 0.2586 | 0.2495 | 0.2456 | 0.2394 | 0.2338 | 0.2327 |
| Orange | 591-610 | 0.3425 | 0.3369 | 0.3225 | 0.3156 | 0.3047 | 0.3008 | 0.2960 |
| Red | 610-760 | 0.3442 | 0.3234 | 0.3087 | 0.2973 | 0.2910 | 0.2873 | 0.2772 |
| total | (400-700) | 24.52 | 24.60 | 24.60 | 24.61 | 24.64 | 24.62 | 24.67 |

| Polypropylene core/Polyethylene sheath, E:F:RB, 20 g/:5 g/L:5 g/L-4 Layers 0-5 min | | mW/cm2 at 5 cm | | | | | |
|---|---|---|---|---|---|---|---|
| | | 3.5 min | 4 min | 4.5 min | 5 min | J/cm2 | |
| Lamp | 400-518 | 23.87 | 23.92 | 23.96 | 23.99 | 7.13 | 96.5% |
| Fluoresc. | 519-760 | 0.82 | 0.80 | 0.79 | 0.78 | 0.26 | 3.5% |
| total | 400-760 | 24.69701 | 24.72073 | 24.74822 | 24.7711 | 7.39 | 99.9% |
| % fluorescence | | 3.3% | 3.2% | 3.2% | 3.1% | 0.03 | 3.5% |
| purple | (400)-450 | 14.9231 | 14.8477 | 14.7970 | 14.7369 | 4.56 | 61.7% |
| Blue | 450-500 | 8.9500 | 9.0729 | 9.1644 | 9.2549 | 2.57 | 34.8% |
| Green | 500-570 | 0.0271 | 0.0281 | 0.0282 | 0.0282 | 0.01 | 0.1% |
| Yellow | 570-591 | 0.2335 | 0.2282 | 0.2260 | 0.2240 | 0.07 | 1.0% |
| Orange | 591-610 | 0.2944 | 0.2866 | 0.2829 | 0.2797 | 0.09 | 1.3% |
| Red | 610-760 | 0.2830 | 0.2709 | 0.2632 | 0.2605 | 0.09 | 1.2% |
| total | (400-700) | 24.71 | 24.73 | 24.76 | 24.78 | 7.39 | 100.0% |

TABLE 49

Royal Carolina Media, Eosin:Fluorescein, 1 layer

| RoyalCarolina Media, Eosin:Fluorescein, 1 layer | | mW/cm2 at 5 cm | | | | | |
|---|---|---|---|---|---|---|---|
| | | 0 | 0.5 min | 1 min | 1.5 min | 2 min | 2.5 min | 3 min |
| Lamp | 400-518 | 45.18 | 44.92 | 44.87 | 44.82 | 44.75 | 44.69 | 44.66 |
| Fluoresc. | 519-760 | 0.78 | 0.79 | 0.78 | 0.75 | 0.73 | 0.72 | 0.70 |
| total | 400-760 | 45.96064 | 45.70756 | 45.64751 | 45.57463 | 45.4783 | 45.41009 | 45.36403 |
| % fluorescence | | 1.7% | 1.7% | 1.7% | 1.7% | 1.6% | 1.6% | 1.5% |
| purple | (400)-450 | 27.0635 | 26.5869 | 26.4423 | 26.2921 | 26.1306 | 25.9930 | 25.8850 |
| Blue | 450-500 | 18.1148 | 18.3232 | 18.4223 | 18.5199 | 18.6103 | 18.6862 | 18.7644 |
| Green | 500-570 | 0.2912 | 0.2955 | 0.2929 | 0.2800 | 0.2687 | 0.2667 | 0.2642 |
| Yellow | 570-591 | 0.2904 | 0.2976 | 0.2912 | 0.2858 | 0.2791 | 0.2745 | 0.2699 |

TABLE 49-continued

| Royal Carolina Media, Eosin:Fluorescein, 1 layer | | | | | | | | |
|---|---|---|---|---|---|---|---|---|
| Orange | 591-610 | 0.1584 | 0.1609 | 0.1572 | 0.1555 | 0.1516 | 0.1508 | 0.1445 |
| Red | 610-760 | 0.0470 | 0.0485 | 0.0466 | 0.0461 | 0.0425 | 0.0436 | 0.0404 |
| total | (400-700) | 45.97 | 45.71 | 45.65 | 45.58 | 45.48 | 45.41 | 45.37 |

| RoyalCarolina Media, Eosin:Fluorescein, 1 layer | | mW/cm2 at 5 cm | | | | | |
|---|---|---|---|---|---|---|---|
| | | 3.5 min | 4 min | 4.5 min | 5 min | J/cm2 | |
| Lamp | 400-518 | 44.59 | 44.59 | 44.57 | 44.54 | 13.43 | 98.4% |
| Fluoresc. | 519-760 | 0.68 | 0.67 | 0.66 | 0.65 | 0.22 | 1.6% |
| total | 400-760 | 45.26928 | 45.2666 | 45.23608 | 45.19001 | 13.65 | 100.0% |
| % fluorescence | | 1.5% | 1.5% | 1.5% | 1.4% | 0.02 | 1.6% |
| purple | (400)-450 | 25.7933 | 25.7023 | 25.6407 | 25.5755 | 7.85 | 57.5% |
| Blue | 450-500 | 18.7845 | 18.8782 | 18.9181 | 18.9484 | 5.58 | 40.9% |
| Green | 500-570 | 0.2519 | 0.2550 | 0.2530 | 0.2491 | 0.08 | 0.6% |
| Yellow | 570-591 | 0.2593 | 0.2589 | 0.2526 | 0.2481 | 0.08 | 0.6% |
| Orange | 591-610 | 0.1426 | 0.1381 | 0.1355 | 0.1327 | 0.04 | 0.3% |
| Red | 610-760 | 0.0421 | 0.0382 | 0.0404 | 0.0403 | 0.01 | 0.1% |
| total | (400-700) | 45.27 | 45.27 | 45.24 | 45.19 | 13.65 | 100.0% |

Example 10

Fluorescence Emission of Re-Dipped Photoactivatable Fibers

A solution of Eosin Y in water was prepared at a concentration of 0.1 g/L, and two polypropylene fibers were dipped in the solution to dope them with chromophore. They were then examined for their fluorescence as seen on DAY 1 to determine how well they retain their fluorescence over time as well as if dipped in water how much chromophore is retained. From this experiment, it can be seen that the tips of the fibers retain fluorescence after 3 days.

Figure 8A:
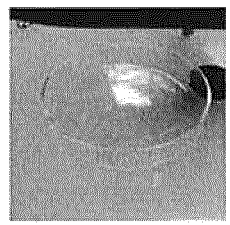
FIGS. 8A-8F illustrate pictures of the fluorescence emission of photoactivatable polypropylene fibers according to one embodiment of the present disclosure which were dipped in a solution of Eosin Y (0.1 g/L).
Figure 8B:
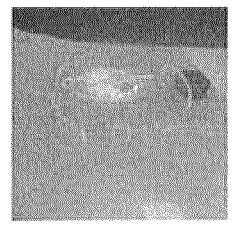
Figure 8C:
Figure 8D:
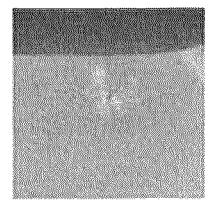
Figure 8E:
Figure 8F:
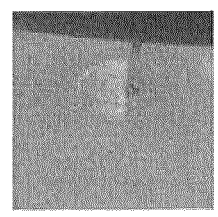

FIGS. 8A and 8B show the fluorescence emission under blue lamp after one day wherein the fibers were not emerged in water. FIGS. 8C and 8D show the fluorescence emission under blue lamp after three days wherein the fibers were not emerged in water. FIGS. 8E and 8F show the fluorescence emission under blue lamp after three days emerged in water.

Example 11

Qualitative Analysis of Dental Fiber Doping

Commercially available dental fibers were dipped into solutions of Eosin Y (300 g/L, 200 g/L, 100 g/L, 50 g/L, 10 g/L, 1 g/L, or 0.1 g/L) for 10 seconds. The fibers were taken out and observed for color, then put under a blue lamp and the fluorescence was observed qualitatively. The 300-100 g/L Eosin Y solutions showed little fluorescence, while the 50 g/L Eosin Y solution showed fluorescence. A significant increase in fluorescence was observed when the 10 g/L Eosin Y solution was used.

Dental fibers were dipped into solutions of fluorescein (50 g/L, 10 g/L, 1 g/L, 0.1 g/L) for 10 seconds. The fibers were then taken out and observed for color, then put under a blue lamp and the fluorescence was observed qualitatively. The 50 g/L fluorescein solution showed fluorescence.

Dental fibers were dipped into solutions of fluorescein: Eosin Y 1:1 (50 g/L, 10 g/L, 1 g/L, 0.1 g/L total chromophore) solution for 10 seconds again. The fibers were then taken out and observed for color, then put under a blue lamp and the fluorescence was observed qualitatively. The 50 g/L fluorescein:Eosin Y 1:1 solution showed little fluorescence. A significant increase in fluorescence was observed when the 10 g/L fluorescein:Eosin Y 1:1 solution was used.

FIGS. 9A-9P illustrate pictures of the fluorescence emission under blue lamp of fibers dipped in a solution of photoactivatable agents, i.e., commercial dental fibers in Eosin Y 50 g/L (FIGS. 9A-9B); commercial dental fibers in Eosin Y 0.1 g/L (FIGS. 9C-9D); commercial dental fibers in fluorescein 50 g/L (FIGS. 9E-19F), commercial dental fibers in fluorescein 0.1 g/L (FIGS. 9G-9H), commercial dental fibers in fluorescein:Eosin Y 50 g/L (FIG. 9I-9J), commercial dental fibers in fluorescein:Eosin Y 0.1 g/L (FIGS. 9K-9L), polypropylene fibers in fluorescein 50 g/L (FIGS. 9M-9N), polypropylene fibers in fluorescein 0.1 g/L (FIGS. 9O-9P).

Polypropylene fibers were dipped in solutions of fluorescein (50 g/L, 10 g/L, 1 g/L, 0.1 g/L total chromophore) for 10 seconds, then taken out and observed for color, then put under a blue lamp and the fluorescence was observed qualitatively. The 50 g/L fluorescein solution showed little fluorescence. An increase in fluorescence was observed when the 10 g/L fluorescein solution was used.

Example 12

Preparation of Photoactivatable Fabric

Figure 10:
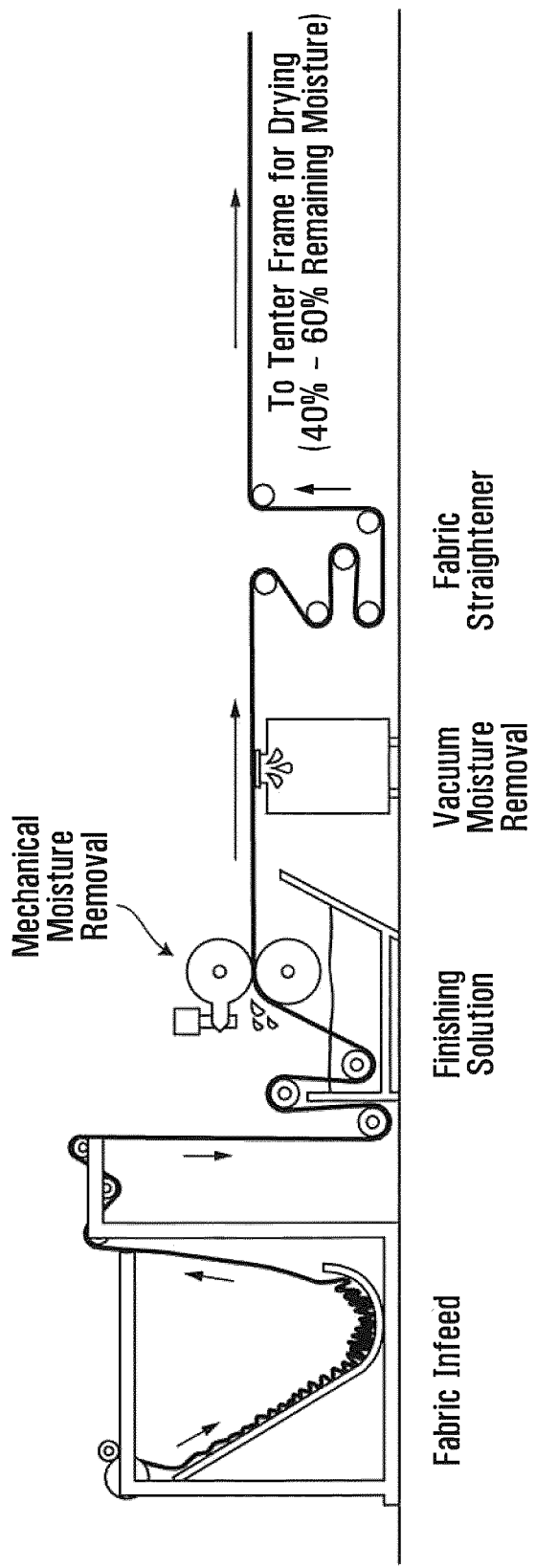
FIG. 10 illustrates a schematic representation of a process for the preparation of photoactivatable fabrics according to one embodiment of the present disclosure.

The polypropylene fiber used in the preparation of the photoactivatable fabric was acquired from Midwest Filtration (West Chester Township, Ohio, U.S.). The fabric tested was composed of polypropylene at densities ranging from 0.45 oz/yd$^2$ to 2.50 oz/yd$^2$. It was observed that the polypropylene fabric at a density of 2.00 oz/yd$^2$ absorbs a significant amount of chromophore, while blocking less light than higher thicknesses (data not shown). A piece of the fabric was dipped in a small chromophore bath without Lurol oil PP-3771 while another piece of the fabric was dipped in a small chromophore bath comprising Lurol oil PP-3771. The dipped fabrics were then roll dried and heated in an oven. The process for the preparation of photoactivatable fabric is illustrated in FIG. 10.

Example 13

Preparation of a Photoactivatable Article of Manufacture

Figure 11A:
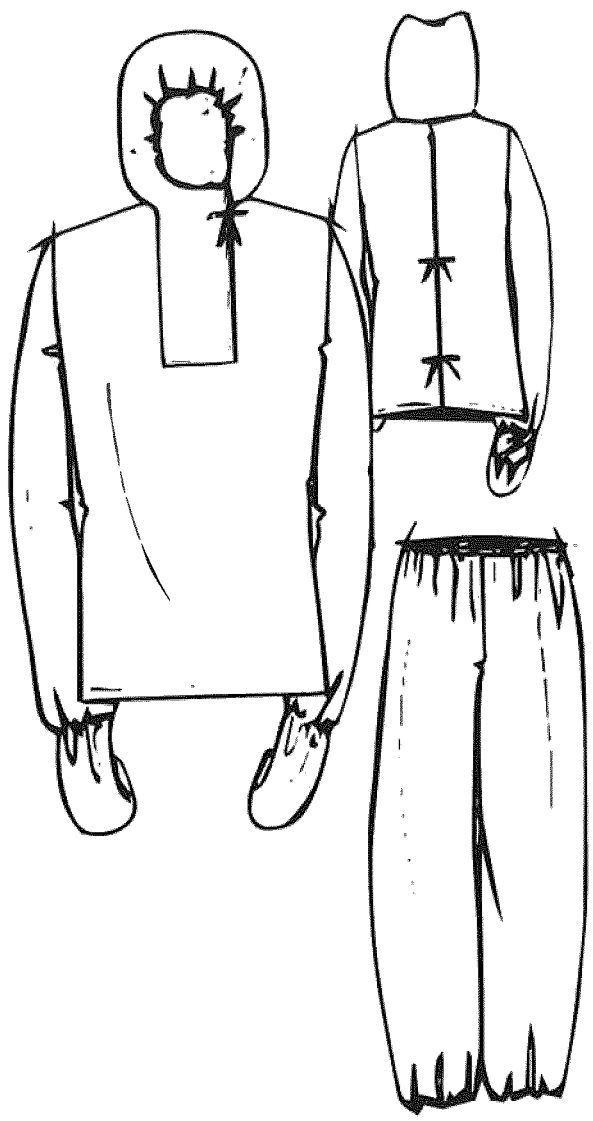
FIGS. 11A-11B.

An article of manufacture comprising a photoactivatable fabric is envisioned. In particular, the article of manufacture is a suit made of a fabric comprising fibers (FIG. 11A). In some instances, the fibers entering the composition of the fabric may be made of a virgin polymer, that is to say a polymer that does not comprise photoactivatable agent. In some other instances, the fibers entering into the composition of the fabric may be made of photoactivatable fibers which comprise photoactivatable agents. In the instances where the fabric comprises fibers made of virgin polymer, the fabric or the article of manufacture made with such fabric may be coated, dipped or sprayed with a photoactivatable agent composition so as to deposit photoactivatable agents onto the fabric and into the interstices created between the fibers of the fabric. A composition of lubricant may also be laid onto the fabric so as to facilitate the insertion of the photoactivatable agents into the interstices created between the fibers of the fabric. In this particular example the article of manufacture is a suit which is to be worn by a subject in need of phototherapy (FIG. 11A). The photoactivatable fibers that are preferred for entering into the fabrication of the suit comprise nylon and polyethylene which comprise one or more photoactivatable agent. The resulting article of manufacture (e.g., a suit-like garment) is then photoactivated under light while being worn by the subject in need of phototherapy.

A suit-like garment was prepared by associating two photoactivatable fabrics having the following composition:
(1) Photoactivatable fabric #1 was made from polypropylene fibers. The resulting fabric was dipped in the composition of 0.50 g/L Eosin Y+Luroil oil.
(2) Photoactivatable fabric #2 was made from polypropylene fibers. The resulting fabric was dipped in the composition of 0.25 g/L Eosin Y+0.25 g/L Fluorescein+Luroil oil.

Figure 11B:

The juxtaposed photoactivatable fabrics were tailored into the suit-like garment illustrated in FIG. 11B. The two fabrics may be joined, stitched, glued, attached, fused, sewed, or bonded or the like, and thereafter tailored accordingly.

Example 14

Cytokine and Growth Factor Modulations Using Photoactivatable Fabrics

The purpose of this experiment was to assess the effect of the photoactivatable fibers of the present disclosure on secretion of cytokines and growth factors. To this end, a blue lamp (129.53 mW/cm$^2$) was placed either on top or on the bottom of human dermal fibroblasts (passage #3 (70,000 cells/well) sample stage at 5 cm. Photoactivatable fabrics as identified in Table 50 below were wrapped around the custom made plastic frame (1-3 turn). Slides were filled with ~1-1.4 ml of PBS and were placed on the stage directly over the fibers. Illumination carried out from bottom to top. Cells were illuminated for 13-15 J/cm$^2$ for most of the fibers and media or for 5 J/cm$^2$. Cells were then incubated for 24 hours in normal media/IFNg and the supernatant was collected and stored at −80° C. Antibody array assay carried out on the collected supernatant and the expression level of cytokines and growth factors were analyzed and normalizing to IFNg stimulated cells. The results presented in Table 51 are based on at least 50% difference in the expression level compared to non-treated control only.

TABLE 50

Composition of photoactivatable fibers/fabrics

| Photoactivatable Fiber/Fabric | Composition |
|---|---|
| 36 | Fabric 1 - polypropylene fibers (blank - no photoactivatable agent) |
| 37 | Fabric 2: polypropylene fibers + Eosin Y |
| 38 | Fabric 3: polypropylene fibers + Eosin y and fluorescein |
| 39 | Fabric 1 + 1 (2 layers) |
| 40 | Fabric 2 + 3 (2 layers) |

TABLE 51

Biological effect of Photoactivatable fabrics

| Sample | | | | | | | |
|---|---|---|---|---|---|---|---|
| Fabric 1 (Blank) | | Fabric 2 (E) | | Fabric 3 (E/F) | | Fabric 2 + 3 (E + E/F) | |
| Photonic evaluation | | | | | | | |
| P = 10.11, B = 6.70, G = 0.04, Y = 0.00, O = 0.00, R = 0.00 | | P = 7.41, B = 4.37, G = 0.09, Y = 0.16, O = 0.11, R = 0.05 | | P = 6.69, B = 4.25, G = 0.13, Y = 0.15, O = 0.09, R = 0.03 | | P = 5.30, B = 2.86, G = 0.14, Y = 0.26, O = 0.20, R = 0.10 | |
| Dose | | | | | | | |
| 15 J/cm$^2$ | | 15 J/cm$^2$ | | 15 J/cm$^2$ | | 15 J/cm$^2$ | |
| Modulations | | | | | | | |
| ↓ | ↑ | ↓ | ↑ | ↓ | ↑ | ↓ | ↑ |
| Cytokines, Chemokines and Growth factors | — | — | — | IL-6, GM-CSF, MCP-2 | — | GM-SCF, IL-2, IL-13, GROα, MCP-2, MCP-3, ANG | G-SCF, I-309, IL-15, IL-7, MDC, TGFβ1, GROα, IGF-1 | ANG |

P = purple,
B = blue,
G = green,
Y = yellow,
O = orange,
R = red

The results represented above are from at least two independent experiments for each media.

The results suggest that the illumination of media 2 (Eosin) and media 3 (Eosin/Fluorescein) combined (layered) may have positive impacts on down regulation of 1-309, IL-15, IL-7, MDC, TGFβ1, GROα and IGF-1. These cytokines and chemokines are involved in conditions such as contact allergic dermatitis (1-309, IL-7), psoriasis (GROα, IL-15, IGF-1), atopic dermatitis (MDC), and scarring (TGFβ1). However, these pathologies are complex and usually modulation of more proteins would be preferable.

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented. Examples of changes, substitutions, and alterations are ascertainable by one skilled in the art and could be made without departing from the scope of the information disclosed herein. All references cited herein are incorporated by reference in their entirety and made part of this application.

What is claimed is:

1. A photoactivatable fiber, wherein the photoactivatable fiber comprises:
    at least one thermoplastic polymer selected from one or more of acrylonitrile butadiene styrene (ABS), polyether sulfone (PES), polyetherether ketone (PEEK), polyphenylene oxide (PPO), polybutylene, polyethylene terephthalate (PET), polybutylene terephthalate (PBT), polymethyl methacrylate polyester, and poly(methyl methacrylate) (PMMA), and
    at least one xanthene dye;
    wherein the at least one xanthene dye is compounded and extruded with the at least one thermoplastic polymer;
    wherein the at least one xanthene dye is present in the at least one thermoplastic polymer at a concentration of between about 10 g/L and about 100 g/L of the total volume of the at least one thermoplastic polymer; and
    wherein the photoactivatable fiber is responsive to actinic light to emit fluorescent light having a power density of between about 0.005 mW/cm$^2$ to about 8 mW/cm$^2$.

2. The photoactivatable fiber as defined in claim 1, wherein the at least one xanthene dye is uniformly dispersed throughout the photoactivatable fiber.

3. The photoactivatable fiber as defined in claim 1, wherein the at least one xanthene dye is non-uniformly dispersed throughout the photoactivatable fiber.

4. The photoactivatable fiber as defined in claim 1, wherein the at least one xanthene dye is layered on the surface of the photoactivatable fiber.

5. The photoactivatable fiber as defined in claim 4, wherein the photoactivatable fiber comprises at least one layer of the at least one xanthene dye on its surface.

6. The photoactivatable fiber as defined in claim 4, wherein the photoactivatable fiber comprises more than one layer of the at least one xanthene dye on its surface.

7. The photoactivatable fiber as defined in claim 1, wherein the at least one thermoplastic polymer is one or more of polybutylene terephthalate (PBT), and poly(methyl methacrylate) (PMMA).

8. The photoactivatable fiber as defined in claim 1, wherein the at least one xanthene dye is selected from the group consisting of Eosin Y, Eosin B, Erythrosine, Fluorescein, Rose Bengal and any mixture thereof.

9. The photoactivatable fiber as defined in claim 1, wherein the at least one xanthene dye is Eosin Y.

10. The photoactivatable fiber as defined in claim 1, wherein the at least one xanthene dye is responsive to actinic light to emit light having a wavelength of between about 400 nm and about 800 nm.

11. The photoactivatable fiber as defined in claim 1, the photoactivatable fiber having a linear mass density of between 400 Deniers and 480 Deniers.

12. The photoactivatable fiber as defined in claim 1, further comprising a lubricant.

13. A photoactivatable fabric comprising a plurality of photoactivatable fibers wherein the photoactivatable fibers comprise:
    i) at least one thermoplastic polymer selected from one or more of acrylonitrile butadiene styrene (ABS), polyether sulfone (PES), polyetherether ketone (PEEK), polyphenylene oxide (PPO), polybutylene, polyethylene terephthalate (PET), polybutylene terephthalate (PBT), polymethyl methacrylate polyester, and poly(methyl methacrylate) (PMMA), and
    ii) at least one xanthene dye, wherein the at least one xanthene dye is compounded and extruded into the photoactivatable fibers;
    wherein the at least one xanthene dye is present in the at least one thermoplastic polymer at a concentration of between about 10 g/L and about 100 g/L of the total volume of the at least one thermoplastic polymer; and
    wherein the photoactivatable fibers are responsive to actinic light to emit fluorescent light having a power density of between about 0.005 mW/cm$^2$ to about 8 mW/cm$^2$.

14. A method for effecting phototherapy on a subject, the method comprising:
    applying a photoactivatable fiber onto the subject, wherein the photoactivatable fiber comprises at least one thermoplastic polymer selected from one or more of acrylonitrile butadiene styrene (ABS), polyether sulfone (PES), polyetherether ketone (PEEK), polyphenylene oxide (PPO), polybutylene, polyethylene terephthalate (PET), polybutylene terephthalate (PBT), polymethyl methacrylate polyester, and poly(methyl methacrylate) (PMMA), and at least one xanthene dye; wherein the at least one xanthene dye is compounded and extruded with the at least one thermoplastic polymer;
    wherein the at least one xanthene dye is present in the at least one thermoplastic polymer at a concentration of between about 10 g/L and about 100 g/L of the total volume of the at least one thermoplastic polymer; and
    illuminating the photoactivatable fiber; wherein illumination of the photoactivatable fiber causes the photoactivatable fiber to emit fluorescent light having a power density of between about 0.005 mW/cm$^2$ to about 8 mW/cm$^2$.

* * * * *